(12) United States Patent
Kallewaard-Lelay et al.

(10) Patent No.: US 11,787,853 B2
(45) Date of Patent: Oct. 17, 2023

(54) NEUTRALIZING ANTI-INFLUENZA B ANTIBODIES AND USES THEREOF

(71) Applicants: MEDIMMUNE, LLC, Gaithersburg, MD (US); HUMABS BIOMED SA, Bellinzona (CH)

(72) Inventors: Nicole Kallewaard-Lelay, Gaithersburg, MD (US); Qing Zhu, Gaithersburg, MD (US); Ebony Benjamin, Gaithersburg, MD (US); Leslie Wachter, Gaithersburg, MD (US); Andy Yuan, Monmouth, NJ (US); Josephine Mary Mcauliffe, Gaithersburg, MD (US); Davide Corti, Bellinzona (CH); Antonio Lanzavecchia, Bellinzona (CH)

(73) Assignees: MEDIMMUNE, LLC, Gaithersburg, MD (US); HUMABS BIOMED SA, Bellinzona (CH)

( * ) Notice: Subject to any disclaimer, the term of this patent is extended or adjusted under 35 U.S.C. 154(b) by 7 days.

(21) Appl. No.: 17/499,495

(22) Filed: Oct. 12, 2021

(65) Prior Publication Data

US 2022/0025020 A1 Jan. 27, 2022

Related U.S. Application Data

(60) Division of application No. 16/676,974, filed on Nov. 7, 2019, now Pat. No. 11,174,304, which is a continuation of application No. 16/361,653, filed on Mar. 22, 2019, now Pat. No. 10,519,221, which is a division of application No. 15/325,603, filed as application No. PCT/US2015/040385 on Jul. 14, 2015, now Pat. No. 10,294,292.

(60) Provisional application No. 62/024,804, filed on Jul. 15, 2014.

(51) Int. Cl.
*C07K 16/10* (2006.01)
*A61P 31/16* (2006.01)
*G01N 33/569* (2006.01)
*A61K 39/00* (2006.01)

(52) U.S. Cl.
CPC ......... *C07K 16/1018* (2013.01); *A61P 31/16* (2018.01); *G01N 33/56983* (2013.01); *A61K 2039/505* (2013.01); *C07K 2317/21* (2013.01); *C07K 2317/33* (2013.01); *C07K 2317/34* (2013.01); *C07K 2317/515* (2013.01); *C07K 2317/56* (2013.01); *C07K 2317/565* (2013.01); *C07K 2317/732* (2013.01); *C07K 2317/76* (2013.01); *C07K 2317/92* (2013.01); *G01N 2333/11* (2013.01); *G01N 2469/10* (2013.01)

(58) Field of Classification Search
None
See application file for complete search history.

(56) References Cited

U.S. PATENT DOCUMENTS

| | | |
|---|---|---|
| 3,766,162 A | 10/1973 | Spector |
| 3,791,932 A | 2/1974 | Schuurs et al. |
| 3,817,837 A | 6/1974 | Rubenstein et al. |
| 4,179,337 A | 12/1979 | Davis et al. |
| 4,233,402 A | 11/1980 | Maggio et al. |
| 4,495,285 A | 1/1985 | Shimizu et al. |
| 4,609,546 A | 9/1986 | Hiratani |
| 4,676,980 A | 6/1987 | Segal et al. |
| 4,766,106 A | 8/1988 | Katre et al. |
| 4,831,175 A | 5/1989 | Gansow et al. |
| 5,595,721 A | 1/1997 | Kaminski et al. |
| 5,807,715 A | 9/1998 | Morrison et al. |
| 6,300,064 B1 | 10/2001 | Knappik et al. |
| 6,306,104 B1 | 10/2001 | Cunningham et al. |
| 8,101,553 B1 | 1/2012 | Kurosawa et al. |
| 8,871,207 B2 | 10/2014 | Lanzavecchia |
| 9,243,054 B2 | 1/2016 | Burioni et al. |
| 10,294,292 B2 * | 5/2019 | Kallewaard-Lelay ....... C07K 16/1018 |
| 10,442,854 B2 | 10/2019 | Kallewaard-Lelay et al. |
| 10,494,419 B2 | 12/2019 | Benjamin et al. |
| 10,519,221 B2 * | 12/2019 | Kallewaard-Lelay ....... C07K 16/1018 |
| 11,174,304 B2 * | 11/2021 | Kallewaard-Lelay ....... C07K 16/1018 |
| 2007/0219149 A1 | 9/2007 | Hasegawa et al. |
| 2010/0080813 A1 | 4/2010 | Lanzavecchia |
| 2011/0014187 A1 | 1/2011 | Burioni et al. |
| 2012/0128684 A1 | 5/2012 | Marasco et al. |

(Continued)

FOREIGN PATENT DOCUMENTS

| | | |
|---|---|---|
| CN | 1671741 A | 9/2005 |
| EP | 1167382 A1 | 1/2002 |

(Continued)

OTHER PUBLICATIONS

Dreyfus et al. Science. Sep. 14, 2012;337 (6100):13438 (Year: 2012).*

(Continued)

*Primary Examiner* — Shanon A. Foley
*Assistant Examiner* — Myron G Hill
(74) *Attorney, Agent, or Firm* — MEDLER FERRO WOODHOUSE & MILLS PLLC

(57) ABSTRACT

The invention relates to antibodies and antigen binding fragments thereof that are capable of binding to influenza B virus hemagglutinin (HA) and neutralizing influenza B virus in two phylogenetically distinct lineages. In one embodiment, the antibody or antigen binding fragment is capable of binding to influenza B virus hemagglutinin and neutralizing influenza B virus in Yamagata and Victoria lineages.

26 Claims, 11 Drawing Sheets

Specification includes a Sequence Listing.

(56) References Cited

U.S. PATENT DOCUMENTS

| | | |
|---|---|---|
| 2016/0257732 A1 | 9/2016 | Benjamin et al. |
| 2017/0218054 A1 | 8/2017 | Kallewaard-Lelay et al. |
| 2018/0155413 A1 | 6/2018 | Kallewaard-Lelay et al. |
| 2019/0015509 A1 | 1/2019 | Kallewaard-Lelay et al. |
| 2020/0109187 A1 | 4/2020 | Kallewaard-Lelay et al. |

FOREIGN PATENT DOCUMENTS

| | | |
|---|---|---|
| EP | 2919813 B1 | 10/2018 |
| RU | 2536956 C1 | 12/2014 |
| WO | 00/52031 A2 | 9/2000 |
| WO | 00/52473 A2 | 9/2000 |
| WO | 2004/007667 A2 | 1/2004 |
| WO | 2004/001007 A2 | 7/2004 |
| WO | 2005/007697 A1 | 1/2005 |
| WO | 2006/124269 A2 | 11/2006 |
| WO | 2007/045477 A2 | 4/2007 |
| WO | 2007/109742 A2 | 9/2007 |
| WO | 2007/117577 A2 | 10/2007 |
| WO | 2007/134327 A2 | 11/2007 |
| WO | 2008/028946 A2 | 3/2008 |
| WO | 2008/054606 A2 | 5/2008 |
| WO | 2008/066691 A2 | 6/2008 |
| WO | 2008/076379 A2 | 6/2008 |
| WO | 2008/084410 A2 | 7/2008 |
| WO | 2008/110937 A2 | 9/2008 |
| WO | 2009/115972 A1 | 9/2009 |
| WO | 2010/010466 A2 | 1/2010 |
| WO | 2010/010467 A2 | 1/2010 |
| WO | 2010/054007 A1 | 5/2010 |
| WO | 2012/082634 A1 | 6/2012 |
| WO | 2013/007770 A1 | 1/2013 |
| WO | 2013/011347 A1 | 1/2013 |
| WO | 2013/043729 A1 | 3/2013 |
| WO | 2013/044203 A2 | 3/2013 |
| WO | 2013/086052 A2 | 6/2013 |
| WO | 2013/132007 A1 | 9/2013 |
| WO | 2014/078268 A1 | 5/2014 |
| WO | 2014/158001 A1 | 10/2014 |
| WO | 2015/051010 A1 | 4/2015 |
| WO | 2016/011035 A2 | 1/2016 |
| WO | 2016/196470 A1 | 12/2016 |
| WO | 2017/123685 A1 | 7/2017 |
| WO | 2017/147248 A1 | 8/2017 |

OTHER PUBLICATIONS

Davies and Riechmann. "Affinity improvement of single antibody VH domains: residues in all three hypervariable regions affect antigen binding." Immunotechnology. 2:169-179 (1996).

Holt et al. "Domain antibodies: proteins for therapy." TRENDS Biotech. 21(11):484 (2003).

Centers for Disease Control and Prevention (CDC), "Antiviral Drugs for Seasonal Influenza: Additional Links and Resources", last reviewed Nov. 30, 2020, 2 pages.

Deyde, Varough M. et al., "Surveillance of Resistance to Adamantanes among Influenza A(H3N1) Viruses Isolated Worldwide," JID, 2007:196 (Jul. 15), pp. 249-257.

Duwe, Susanne, "Influenza viruses—antiviral therapy and resistance," GMS Infectious Diseases, 2017, vol. 5, pp. 1-10.

Fan, Gaowei et al., "Bispecific antibodies and their applications," Journal of Hematology & Oncology, vol. 8, No. 130, 2015, 14 pages.

Holliger, Philipp et al., "Diabodies: Small bivalent and bispecific antibody fragments," Proc. Natl. Acad. Sci. USA, vol. 90, Jul. 1993, pp. 6444-6448.

Lampejo, Temi, "Influenza and antiviral resistance: an overview", European Journal of Clinical Microbiology & Infectious Diseases, Feb. 13, 2020, 8 pages.

Abed et al., "A Review of Clinical Influenza A and B Infections with Reduced Susceptibility to Both Oseltamivir and Zanamivir," Open Forum Infectious Diseases 4(3): ofx105 (2017).

Ali et al., "Evaluation of MEDI8852, an Anti-Influenza A Monoclonal Antibody, in Treating Acute Uncomplicated Influenza," Antimicrobial Agents and Chemotherapy 62(11): e00694-18 (2018).

Pakula and Sauer, "Genetic Analysis of Protein and Function." Annu. Rev. Genet. 23:289-310 (1989).

PAn et al., "Weight-based Dosing in Medication Use: What Should We Know?" Patient Preference and Adherence 10:549-560 (2016).

Office Action in Chinese Application No. 201580038244.1 dated Jan. 17, 2020.

Office Action in Japanese Application No. 2017-561892 dated Jun. 2, 2020.

Non-final Office Action in U.S. Appl. No. 16/560,040 dated Apr. 16, 2020.

Office Action in U.S. Appl. No. 16/068,941 dated Feb. 5, 2020.

Bouvier, "The Future of Influenza Vaccines: A Historical and Clinical Perspective," Vaccines 6:58 (2018).

Deyev et al., "Modern Technologies for Creating Synthetic Antibodies for Clinical Application," Acta Naturae, 1. 32-50 (2009).

GENBANK Accession ID AAK94805.1, immunoglobulin light chain variable region, partial [Homo sapiens], published Dec. 31, 2001.

GENBANK Accession ID ACS95408.1, immunoglobulin heavy chain variable region, partial [Homo sapiens], published Dec. 31, 2001.

Ignatiev et al., Peculiarities of the Antigenic Structure of Hemagglutinin, Recognizable by Antibodies against Modern Viruses of Influenza A Subtypes H5 and H1 (2012).

Kallewaard et al., "Structure and Function Analysis of an Antibody Recognizing All Influenza A Subtypes," Cell 166: 596-608 (2016).

LIN et al., "Recent Changes Among Human Influenza Viruses," Virus Res., 103: 47-52 (2004).

Roit er al., Immunology [Textbook source], p. 49 (1991).

Office Action in U.S. Appl. No. 15/026,276, dated Apr. 17, 2019.

Office Action in U.S. Appl. No. 16/068,941, dated Oct. 21, 2019.

Benjamin et al., "A Broadly Neutralizing Human Monoclonal Antibody Directed against a Novel Conserved Epitope on the Influenza Virus H3 Hemagglutinin Globular Head," J Virol 88(12):6743-6750 (2014).

Biere et al., "Differentiation of Influenza B Virus Lineages Yamagata and Victoria by Real-Time PCR," J Clin Microbiol 48:1425-1427 (2010).

Chai et al., "A broadly protective therapeutic antibody against influenza B virus with two mechanisms of action," Nature Comm 8:14234 (2017).

Corti et al., "Heterosubtypic neutralizing antibodies are produced by individuals immunized with a seasonal influenza vaccine," J Clin Invest 120:1663-1673 (2010).

Corti et al., "A Neutralizing Antibody Selected from Plasma Cells That Binds to Group 1 and Group 2 Influenza A Hemagglutinins," Science 333(6044):850-856 (2011).

Corti et al., "Cross-neutralization of four paramyxoviruses by a human monoclonal antibody," Nature 501 (7467):439-443 (2013).

Corti et al., "Tackling influenza with broadly neutralizing antibodies," Curr Opin Virol 24:60-69 (2017).

Dreyfus et al., "Highly Conserved Protective Epitopes on Influenza B Viruses," Science 337(6100):1343-1348 (2012).

Ekiert et al., "Antibody recognition of a highly conserved influenza virus epitope: implications for universal prevention and therapy," Science 324(5924):246-251 (2009).

Ekiert et al., "A Highly Conserved Neutralizing Epitope on Group 2 Influenza A Viruses," Science 333(6044):843-850 (2011).

Ekiert et al., "Cross-neutralization of influenza A viruses mediated by a single antibody loop," Nature 489 (7417):526-532 (2012).

Friesen et al., "A common solution to group 2 influenza virus neutralization," Proc Natl Acad Sci USA 111(1):445-450 (2014).

Gerhard et al., "Prospects for Universal influenza Virus Vaccine," Emerg Infect Dis 12(4):569-574 (2006).

Gioia et al., "Cross-subtype immunity against Avian Infi uenza in Persons Recently Vaccinated for Influenza," Emerg Infect Dis 14(1):121-128 (2008).

Greenspan et al., "Defining epitopes: It's not as easy as it seems," Nature Biotechnol 17:936-937 (1999).

(56) References Cited

OTHER PUBLICATIONS

Hassantoufighi et al., "A practical influenza neutralization assay to simultaneously quantify hemagglutinin and neuraminidase-inhibiting antibody responses," Vaccine 28:790-797 (2010).
Kashyap et al., "Combinatorial antibody libraries from survivors of the Turkish H5N1 avian influenza outbreak reveal virus neutralization strategies," Proc Nail Acad Sci USA 105(16):5986-5991 (2008).
Kaverin et al., "Epitope Mapping of the Hemagglutinin Molecule of a Highly Pathogenic H5N1 Influenza Virus by Using Monoclonal Antibodies," J Virol 81(23):12911-12917 (2007).
Kozbor et al., "The production of monoclonal antibodies from human lymphocytes," Immunol Today 4(3):72-79 (1983).
Krause et al., "A Broadly Neutralizing Human Monoclonal Antibody That Recognizes a Conserved, Novel Epitope on the Globular Head of the Influenza H1N1 Virus Hemagglutinin," J Virol 85(20):10905-10908 (2011).
Lee et al., "Heterosubtypic antibody recognition of the influenza virus hemagglutinin receptor binding site enhanced by avidity," Proc Natl Acad Sci USA 109(42):17040-17045 (2012).
Li et al., "Pandemic H1N1 influenza vaccine induces a recall response in humans that favors broadly cross-reactive memory B cells," Proc Natl Acad Sci USA 109(23):9047-9052 (2012).
Nakamura et al., "An In Vivo Human-Plasmablast Enrichment Technique Allows Rapid Identification of Therapeutic Influenza A Antibodies," Cell Host Microbe 14:93-103 (2013).
Nguyen et al., "Heterosubtypic Immunity to Influenza A Virus infection Requires B Celis but Not CD8+ Cytotoxic T Lymphocytes," J Virol 183:368-376 (2001).
Okuno et al., "A Common Neutralizing Epitope Conserved between the Hemagglutinins of Influenza A Virus H1 and H2 Strains," J Virol 67(5):2552-2558 (1993).
Pappas et al., "Rapid development of broadly influenza neutralizing antibodies through redundant mutations," Nature 516(7531):418-422 (2014).
Paul et al., eds. Fundamental Immunology 3rd Edition (1993), pp. 292-295.
Prabhu et al., "Monoclonal Antibodies against the Fusion Peptide of Hemagglutinin Protect Mice from Lethal Influenza A Virus H5N1 Infection," J Virol 83(6):2553-2562 (2009).
Ren et al., "Epitope-focused vaccine design against influenza A and B viruses," Curr Opin Immunol 42:83-90 (2016).
Rowe et al., "Detection of Antibody to Avian Influenza A (H5N1) Virus in Human Serum by Using a Combination of Serologic Assays," J Clin Microbiol 37(4):937-943 (1999).
Rudikoff et al., "Single amino acid substitution altering antigen-binding specificity," Proc Natl Acad Sci USA 79(6):1979-1983 (1982).
Simmons et al., "Prophylactic and Therapeutic Efficacy of Human Monoclonal Antibodies against H5N1 Influenza," PLOS Med 4(5):e178 (2007).
Smirnov et al., "Prevention and treatment of bronchopneumonia in mice caused by mouse-adapted variant of avian H5N2 influenza A virus using monoclonal antibody against conserved epitope in the HA stem region," Arch Virol 145:1733-1741 (2000).
Sui et al., "Structural and functional bases for broad-spectrum neutralization of avian and human influenza A viruses," Nature Struct Mol Biol 16(3):265-273 (2009).
Temperton et al., "Longitudinally Profiling Neutralizing Antibody Response to SARS Coronavirus with Pseudotypes," Emerg Infect Dis 11(3):411-416 (2005).
Thompson et al., "Influenza-Associated Hospitalizations in the United States," JAMA 292:1333-1340 (2004).
Throsby et al., "Heterosubtypic Neutralizing Monoclonal Antibodies Cross-Protective against H5N1 and H1N1 Recovered from Human IgM+ Memory B Cells," PLOS One 3(12):e3942 (2008).
Traggiai et al., "An efficient method to make human monoclonal antibodies from memory B cells: potent neutralization of SARS coronavirus," Nature Med 10:871-875 (2004).
Vareckova et al., "HA2-specific monclonal antibodies as tools for diiferential recognition of influenza A virus antigenic subtypes," Virus Res 132(1-2):181-186 (2008).
Wagner et al., "Bispecific antibody generated with sortase and click chemistry has broad antiinfluenza activity," Proc Natl Acad Sci USA 111(47):16820-16825 (2014).
Wang, Qinghua et al., "Crystal Structure of Unliganded Influenza B Virus Hemagglutinin," J Virol 82(6):3011-3020 (2008).
Wang, Taia T. et al., "Broadly Protective Monoclooonal Antibodies against H3 Influenza Viruses following Sequential Immunization with Different Hemagglutinins," PLOS Pathog 6(2):e1000796 (2010).
Whittle et al., "Broadly neutralizing human antibody that recognizes the receptor-binding pocket of influenza virus hemagglutinin," Proc Natl Acad Sci USA 108(34):14216-14221 (2011).
Wilson et al., "Structure of the hemagglutinin membrane glycoprotein of influenza virus at 3 Å resolution," Nature 289:366-373 (1981).
Wrammert et al., "Rapid Cloning of High Affinity Human Monoclonal Antibodies Against Inlfuenza Virus," Nature 453(7195):667-671 (2008).
Wrammert et al., "Broadly cross-reactive antibodies dominate the human B cell response against 2009 pandemic H1N1 influenza virus infection," J Exp Med 208(1):181-193 (2011).
Xiang et al., "Framework Residues 71 and 93 of the Chimeric B72.3 Antibody are Major Determinants of the Conformation of Heavy-chain Hypervariable Loops," J Mol Biol 253:385-390 (1995).
Yasugi et al., "Human Monoclonal Antibodies Broadly Neutralizing against Influenza B Virus," PLOS Pathog 9(2):e1003150 (2013).
Yoshida et al., "Cross-Protective Potential of a Novel Monoclonal Antibody Directed against Antigenic Site B of the Hemagglutinin of Influenza A Viruses," PLOS Pathog 5(3):e1000350 (2009).
Zabetakis et al., "Contributions of the Complementarity Determining Regions to the Thermal Stability of a Single-Domain Antibody," PLoS ONE 8(10):e77678 (2013).
ZHOU et al., "Hospitalizations Associated With Influenza and Respiratory Syncytial Virus in the United States, 1993-2008," Clin Infect Dis 54(10):1427-1436.
Non-final Office Action issued in U.S. Appl. No. 15/026,276, dated Apr. 6, 2018.
Non-final Office Action issued in U.S. Appl. No. 15/026,276, dated Oct. 19, 2018.
Non-final Office Action issued in U.S. Appl. No. 15/325,603, dated Jun. 27, 2017.
Final Office Action issued in U.S. Appl. No. 15/325,603, dated Mar. 8, 2018.
Non-final Office Action issued in U.S. Appl. No. 15/325,603, dated Sep. 7, 2018.
Non-final Office Action issued in U.S. Appl. No. 15/577,799, dated Feb. 21, 2019.

* cited by examiner

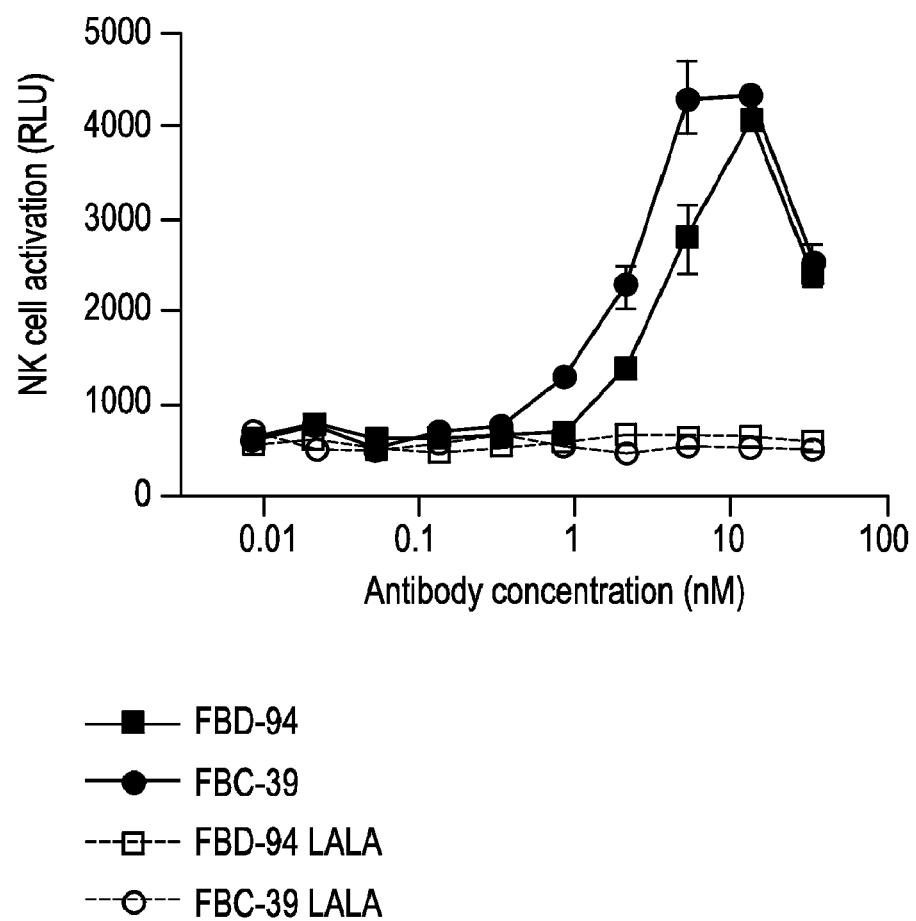

FIG. 5A

| Kabat | CDRH1 (31-35b) | CDRH2 (50-65) | |
|---|---|---|---|
| FBD-56 VH | EVQLVESGGHLVQPGRSLRLSCAASGFTFHDYAMNWVRQAPGKGLEWVSVIS--WDSGRIGYADSVKGRFTISRDNAKNSSYLQ | (SEQ.ID.NO.2) |
| FBD-94 VH | EVQLVESGGGLVQPGRSLRLSCAVSGFIFDYAINWVRQAPGKGLEWVSIIS--WDSGRIGYADSVRGRFTISRDNAKNSSFLQ | (SEQ.ID.NO.12) |
| FBC-39 VH | EVQLVSGGGLVRPGGSLRLSCAASGLSFNAWMSWVRQAPGKGLEWVGRIKSNTDGGTTDYAAPVKGRFSISRDDSKNMLFLH | (SEQ.ID.NO.22) |
| FBC-39 LSL VH | EVQLVESGGGLVRPGGSLRLSCAASGLSFNAWMSWVRQAPGKGLEWVGRIKSNTDGGTTDYAAPVKGRFTISRDDSKNTLYLQ | (SEQ.ID.NO.32) |
| FBC-39 FSL VH | EVQLVESGGGLVRPGGSLRLSCAASGESFNAWMSWVRQAPGKGLEWVGRIKSNTDGGTTDYAAPVKGRFTISRDDSKNTLYLQ | (SEQ.ID.NO.42) |
| FBC-39 LTL VH | EVQLVESGGGLVRPGGSLRLSCAASGLTFNAWMSWVRQAPGKGLEWVGRIKSNTDGGTTDYAAPVKGRFTISRDDSKNTLYLQ | (SEQ.ID.NO.52) |
| FBC-39 FTL VH | EVQLVESGGGLVRPGGSLRLSCAASGFTFNAWMSWVRQAPGKGLEWVGRIKSNTDGGTTDYAAPVKGRFTISRDDSKNTLYLQ | (SEQ.ID.NO.62) |
| FBC-39 FSS VH | EVQLVESGGGLVRPGGSLRLSCAASGESFSAWMSWVRQAPGKGLEWVGRIKSNTDGGTTDYAAPVKGRFTISRDDSKNTLYLQ | (SEQ.ID.NO.74) |
| FBC-39 LTS VH | EVQLVESGGGLVRPGGSLRLSCAASGLTFSAWMSWVRQAPGKGLEWVGRIKSNTDGGTTDYAAPVKGRFTISRDDSKNTLYLQ | (SEQ.ID.NO.90) |
| FBC-39 FTS VH | EVQLVESGGGLVRPGGSLRLSCAASGFTFSAWMSWVRQAPGKGLEWVGRIKSNTDGGTTDYAAPVKGRFTISRDDSKNTLYLQ | (SEQ.ID.NO.106) |

| | CDRH3 (95-102) | |
|---|---|---|
| FBD-56 VH | MNSLRPEDTALYYCVRDMLAYYSDNS--GKYNVYGMDVWGQGTTVTVSS | (SEQ.ID.NO.2) |
| FBD-94 VH | MNSLRPEDTAVYYCVKDMLAYYDGS--GTRYNLYGMDVWGQGTTVTVSS | (SEQ.ID.NO.12) |
| FBC-39 VH | MSSLRTEDTAVYYCATDGPYSDDFRSGYAARYRYFGMDVWGQGTTVTVSS | (SEQ.ID.NO.22) |
| FBC-39 LSL VH | MSSLKTEDTAVYYCTTDGPYSDDFRSGYAARYRYFGMDVWGQGTTVTVSS | (SEQ.ID.NO.32) |
| FBC-39 FSL VH | MSSLKTEDTAVYYCTTDGPYSDDFRSGYAARYRYFGMDVWGQGTTVTVSS | (SEQ.ID.NO.42) |
| FBC-39 LTL VH | MSSLKTEDTAVYYCTTDGPYSDDFRSGYAARYRYFGMDVWGQGTTVTVSS | (SEQ.ID.NO.52) |
| FBC-39 FTL VH | MSSLKTEDTAVYYCTTDGPYSDDFRSGYAARYRYFGMDVWGQGTTVTVSS | (SEQ.ID.NO.62) |
| FBC-39 FSS VH | MSSLKTEDTAVYYCTTDGPYSDDFRSGYAARYRYFGMDVWGQGTTVTVSS | (SEQ.ID.NO.74) |
| FBC-39 LTS VH | MSSLKTEDTAVYYCTTDGPYSDDFRSGYAARYRYFGMDVWGQGTTVTVSS | (SEQ.ID.NO.90) |
| FBC-39 FTS VH | MSSLKTEDTAVYYCTTDGPYSDDFRSGYAARYRYFGMDVWGQGTTVTVSS | (SEQ.ID.NO.106) |

FIG. 5B

|         | CDRL1 (24-34) | CDRL2 (50-56) | |
|---------|---|---|---|
| Kabat   | | | |
| FBD-56 VL | EIVLTQSPATLSLSPGERATLSCRASQSVSTFLAWYQQKPGQAPRLLMYDASNRATGIPARFSGSGSGTD | (SEQ.ID.NO.7) |
| FBD-94 VL | EIVLTQSPATLSLSPGERATLSCRASRSITTLAWYQQKPGQAPRLLIYDASNRATSVPARFSGSGSGTD | (SEQ.ID.NO.17) |
| FBC-39 VL | DIQMTQSPSSVSASVGDRVTITCRASQDISTWLAWYQQKPGKAPKLLIYAASSLQSGVPSRFSGSGSGTD | (SEQ.ID.NO.27) |
| FBC-39 LSL VL | DIQMTQSPSSVSASVGDRVTITCRASQDISTWLAWYQQKPGKAPKLLIYAASSLQSGVPSRFSGSGSGTD | (SEQ.ID.NO.37) |
| FBC-39 FSL VL | DIQMTQSPSSVSASVGDRVTITCRASQDISTWLAWYQQKPGKAPKLLIYAASSLQSGVPSRFSGSGSGTD | (SEQ.ID.NO.47) |
| FBC-39 LTL VL | DIQMTQSPSSVSASVGDRVTITCRASQDISTWLAWYQQKPGKAPKLLIYAASSLQSGVPSRFSGSGSGTD | (SEQ.ID.NO.57) |
| FBC-39 FTL VL | DIQMTQSPSSVSASVGDRVTITCRASQDISTWLAWYQQKPGKAPKLLIYAASSLQSGVPSRFSGSGSGTD | (SEQ.ID.NO.67) |
| FBC-39 FSS VL | DIQMTQSPSSVSASVGDRVTITCRASQDISTWLAWYQQKPGKAPKLLIYAASSLQSGVPSRFSGSGSGTD | (SEQ.ID.NO.82) |
| FBC-39 LTS VL | DIQMTQSPSSVSASVGDRVTITCRASQDISTWLAWYQQKPGKAPKLLIYAASSLQSGVPSRFSGSGSGTD | (SEQ.ID.NO.98) |
| FBC-39 FTS VL | DIQMTQSPSSVSASVGDRVTITCRASQDISTWLAWYQQKPGKAPKLLIYAASSLQSGVPSRFSGSGSGTD | (SEQ.ID.NO.114) |

|         | CDRL3 (89-97) | |
|---------|---|---|
| FBD-56 VL | FTLTISSLEPEDFAIYYCQQRSHWPPIFGQGTRLEIK | (SEQ.ID.NO.7) |
| FBD-94 VL | FTLTISSLEPDDFAIYYCQQRDHWPPIFGQGTRLEIK | (SEQ.ID.NO.17) |
| FBC-39 VL | FTLTISSLQPEDFATYYCQQANSFPPTFGQGTKLEIK | (SEQ.ID.NO.27) |
| FBC-39 LSL VL | FTLTISSLQPEDFATYYCQQANSFPPTFGQGTKLEIK | (SEQ.ID.NO.37) |
| FBC-39 FSL VL | FTLTISSLQPEDFATYYCQQANSFPPTFGQGTKLEIK | (SEQ.ID.NO.47) |
| FBC-39 LTL VL | FTLTISSLQPEDFATYYCQQANSFPPTFGQGTKLEIK | (SEQ.ID.NO.57) |
| FBC-39 FTL VL | FTLTISSLQPEDFATYYCQQANSFPPTFGQGTKLEIK | (SEQ.ID.NO.67) |
| FBC-39 FSS VL | FTLTISSLQPEDFATYYCQQANSFPPTFGQGTKLEIK | (SEQ.ID.NO.82) |
| FBC-39 LTS VL | FTLTISSLQPEDFATYYCQQANSFPPTFGQGTKLEIK | (SEQ.ID.NO.98) |
| FBC-39 FTS VL | FTLTISSLQPEDFATYYCQQANSFPPTFGQGTKLEIK | (SEQ.ID.NO.114) |

FIG. 5C

```
            CDRH1(27-38)                                           CDRH2(56-65)
IMGT
FBD-56  VH  EVQLVESGG-HLVQPGRSLRLSCAASGTTF----EDYAMNWVRQAPGKGLEWVSVISWD--SGRIGYADSVK-GRFTISRDNAKNSSYLQMNSLRPED  (SEQ.ID.NO.2)
FBD-94  VH  EVQLVESGG-GLVQPGRSLRLSCAVSGEIF----EDYAINWVRQAPGKGLEWVSIISWD--SGRIGYADSVR-GRFTISRDNAKNSSFLQMNSLRPED  (SEQ.ID.NO.12)
FBC-39  VH  EVQLVESGG-GLVKPGGSLRLSCAASGLSF----LNAWMSWVRQAPGKGLEWVGRIKSNTDGGTTDYAAPVKGRFSISRDDSKAMLFHMSSLRTPED   (SEQ.ID.NO.22)
FBC-39 LSL VH EVQLVESGG-GLVKPGGSLRLSCAASGLSF----LNAWMSWVRQAPGKGLEWVGRIKSNTDGGTTDYAAPVK-GRFTISRDDSKNTLYLQMSSLKTED (SEQ.ID.NO.32)
FBC-39 FSL VH EVQLVESGG-GLVKPGGSLRLSCAASGFSF----LNAWMSWVRQAPGKGLEWVGRIKSNTDGGTTDYAAPVK-GRFTISRDDSKNTLYLQMSSLKTED (SEQ.ID.NO.42)
FBC-39 LTL VH EVQLVESGG-GLVKPGGSLRLSCAASGLTF----LNAWMSWVRQAPGKGLEWVGRIKSNTDGGTTDYAAPVK-GRFTISRDDSKNTLYLQMSSLKTED (SEQ.ID.NO.52)
FBC-39 FTL VH EVQLVESGG-GLVKPGGSLRLSCAASGFTF----LNAWMSWVRQAPGKGLEWVGRIKSNTDGGTTDYAAPVK-GRFTISRDDSKNTLYLQMSSLKTED (SEQ.ID.NO.62)
FBC-39 FSS VH EVQLVESGG-GLVKPGGSLRLSCAASGFSF----SNAWMSWVRQAPGKGLEWVGRIKSNTDGGTTDYAAPVK-GRFTISRDDSKNTLYLQMSSLKTED (SEQ.ID.NO.74)
FBC-39 LTS VH EVQLVESGG-GLVKPGGSLRLSCAASGLTF----SNAWMSWVRQAPGKGLEWVGRIKSNTDGGTTDYAAPVK-GRFTISRDDSKNTLYLQMSSLKTED (SEQ.ID.NO.90)
FBC-39 FTS VH EVQLVESGG-GLVKPGGSLRLSCAASGFTF----SNAWMSWVRQAPGKGLEWVGRIKSNTDGGTTDYAAPVK-GRFTISRDDSKNTLYLQMSSLKTED (SEQ.ID.NO.106)

CDRH3(105-117)
FBD-56  VH  TALYYCVRDMLAYYSDNS--GKKYNVYGMDVWGQGTTVTVSS      (SEQ.ID.NO.2)
FBD-94  VH  TAVYYCVKDMLAYYYDGS--GIRYNLYGMDVWGQGTTVTVSS      (SEQ.ID.NO.12)
FBC-39  VH  TAVYYCATDGPYSDDFRSGYAARYRYFGMDVWGQGTTVTVSS      (SEQ.ID.NO.22)
FBC-39 LSL VH TAVYYCHTDGPYSDDFRSGYAARYRYFGMDVWGQGTTVTVSS     (SEQ.ID.NO.32)
FBC-39 FSL VH TAVYYCHTDGPYSDDFRSGYAARYRYFGMDVWGQGTTVTVSS     (SEQ.ID.NO.42)
FBC-39 LTL VH TAVYYCHTDGPYSDDFRSGYAARYRYFGMDVWGQGTTVTVSS     (SEQ.ID.NO.52)
FBC-39 FTL VH TAVYYCHTDGPYSDDFRSGYAARYRYFGMDVWGQGTTVTVSS     (SEQ.ID.NO.62)
FBC-39 FSS VH TAVYYCHTDGPYSDDFRSGYAARYRYFGMDVWGQGTTVTVSS     (SEQ.ID.NO.74)
FBC-39 LTS VH TAVYYCHTDGPYSDDFRSGYAARYRYFGMDVWGQGTTVTVSS     (SEQ.ID.NO.90)
FBC-39 FTS VH TAVYYCHTDGPYSDDFRSGYAARYRYFGMDVWGQGTTVTVSS     (SEQ.ID.NO.106)
```

FIG. 5D

|  | CDRL1 (27-38) | CDRL2 (56-65) | |
|---|---|---|---|
| IMGT | | | |
| FBD-56 VL | EIVLTQSPATLSLSPGERATLSCRASQSV------STFLAWYQQKPGQAPRLLMYDA---- | SNRATGIP-ARFSGSG- | (SEQ.ID.NO.7) |
| FBD-94 VL | EIVLTQSPATLSLSPGERATLSCRASRSI------TTFLAWYQQKPGQAPRLLIYDA---- | SNRAIGVP-ARFSGSG- | (SEQ.ID.NO.17) |
| FBC-39 VL | DIQMTQSPSSVSASVGDRVTITCRASQDI------STWLAWYQQKPGKAPKLLIYAA---- | SSLQSGVP-SRFSGSG- | (SEQ.ID.NO.27) |
| FBC-39 LSL VL | DIQMTQSPSSVSASVGDRVTITCRASQDI------STWLAWYQQKPGKAPKLLIYAA---- | SSLQSGVP-SRFSGSG- | (SEQ.ID.NO.37) |
| FBC-39 FSL VL | DIQMTQSPSSVSASVGDRVTITCRASQDI------STWLAWYQQKPGKAPKLLIYAA---- | SSLQSGVP-SRFSGSG- | (SEQ.ID.NO.47) |
| FBC-39 LTL VL | DIQMTQSPSSVSASVGDRVTITCRASQDI------STWLAWYQQKPGKAPKLLIYAA---- | SSLQSGVP-SRFSGSG- | (SEQ.ID.NO.57) |
| FBC-39 FTL VL | DIQMTQSPSSVSASVGDRVTITCRASQDI------STWLAWYQQKPGKAPKLLIYAA---- | SSLQSGVP-SRFSGSG- | (SEQ.ID.NO.67) |
| FBC-39 FSS VL | DIQMTQSPSSVSASVGDRVTITCRASQDI------STWLAWYQQKPGKAPKLLIYAA---- | SSLQSGVP-SRFSGSG- | (SEQ.ID.NO.82) |
| FBC-39 LTS VL | DIQMTQSPSSVSASVGDRVTITCRASQDI------STWLAWYQQKPGKAPKLLIYAA---- | SSLQSGVP-SRFSGSG- | (SEQ.ID.NO.98) |
| FBC-39 FTS VL | DIQMTQSPSSVSASVGDRVTITCRASQDI------STWLAWYQQKPGKAPKLLIYAA---- | SSLQSGVP-SRFSGSG- | (SEQ.ID.NO.114) |

|  | CDRL3 (105-117) | |
|---|---|---|
| FBD-56 VL | SGTDFTLTISSLEPEDEATYYCQQRSH----WPPIFGQGTRLEIK | (SEQ.ID.NO.7) |
| FBD-94 VL | SGTDFTLTINSLEPDDEATYYCQQRDH----WPPIFGQGTRLEIK | (SEQ.ID.NO.17) |
| FBC-39 VL | SGTDFTLTISSLQPEDFATYYCQQANS----FPPIFGQGTKLEIK | (SEQ.ID.NO.27) |
| FBC-39 LSL VL | SGTDFTLTISSLQPEDFATYYCQQANS----FPPIFGQGTKLEIK | (SEQ.ID.NO.37) |
| FBC-39 FSL VL | SGTDFTLTISSLQPEDFATYYCQQANS----FPPIFGQGTKLEIK | (SEQ.ID.NO.47) |
| FBC-39 LTL VL | SGTDFTLTISSLQPEDFATYYCQQANS----FPPIFGQGTKLEIK | (SEQ.ID.NO.57) |
| FBC-39 FTL VL | SGTDFTLTISSLQPEDFATYYCQQANS----FPPIFGQGTKLEIK | (SEQ.ID.NO.67) |
| FBC-39 FSS VL | SGTDFTLTISSLQPEDFATYYCQQANS----FPPIFGQGTKLEIK | (SEQ.ID.NO.82) |
| FBC-39 LTS VL | SGTDFTLTISSLQPEDFATYYCQQANS----FPPIFGQGTKLEIK | (SEQ.ID.NO.98) |
| FBC-39 FTS VL | SGTDFTLTISSLQPEDFATYYCQQANS----FPPIFGQGTKLEIK | (SEQ.ID.NO.114) |

FIG. 6

Glu Val Gln Leu Val Xaa$_1$ Ser Gly Gly Gly Leu Val Lys Pro Gly Gly Ser Leu Arg Leu

Ser Cys Ala Ala Ser Gly Xaa$_2$Xaa$_3$Phe Xaa$_4$ Asn Ala Trp Met Ser Trp Val Arg Gln Ala
<u>                              (HCDR1)</u>

Pro Gly Lys Gly Leu Glu Trp Val Gly Arg Ile Lys Ser Asn Thr Asp Gly Gly Thr Thr
                                      (HCDR2)

Asp Tyr Ala Ala Pro Val Lys Gly Arg Phe Xaa$_5$ Ile Ser Arg Asp Asp Ser Lys Asn Xaa$_6$

Leu Xaa$_7$ Leu Xaa$_8$ Met Xaa$_9$ Ser Leu Xaa$_{10}$Thr Glu Asp Thr Ala Val Tyr Tyr Cys Xaa$_{11}$Thr
(HCDR3)
Asp Gly Pro Tyr Ser Asp Asp Phe Arg Ser Gly Tyr Ala Ala Arg Tyr Arg Tyr Phe Gly

Met Asp Val Trp Gly Gln Gly Thr Thr Val Thr Val Ser Ser (SEQ ID NO: 71)

FIG. 7

Asp Ile Gln Met Thr Gln Ser Pro Ser Ser Val Ser Ala Ser Val Gly Asp Arg Val Thr

Ile Thr Cys <u>Arg Ala Ser Gln Asp Ile Ser Thr Trp Leu Ala</u> Trp Tyr Gln Gln Lys Pro
      (LCDR1)

Gly Lys Ala Pro Lys Leu Leu Ile Tyr <u>Ala Ala Ser Ser Leu Gln Ser</u> Gly Val Pro Ser
                      (LCDR2)

Arg Phe Ser Gly Ser Gly Ser Gly Thr Asp Phe Thr Leu Thr Ile Ser Ser Leu Gln Pro

Glu Asp Phe Ala Thr Tyr Xaa$_1$ Cys <u>Gln Gln Ala Asn Ser Phe Pro Pro Thr Phe Gly Gln
                              (LCDR3)

Gly Thr Lys Leu Glu Ile Lys (SEQ ID NO: 72)

FIG. 8

```
           1                  20                  40                  60                  80
           |                   |                   |                   |                   |
B/MY/04    DRICTGITSSNSPHVVKTATQGEVNVTGVIPLTTTPTKSHFANLKGTETRGKLCPKCLNCTDLDVALGRPKCTGNIPSARVSILHEVRPVTSG  (SEQ.ID.NO.155)
B/ELA/06   DRICTGITSSNSPHVVKTATQGEVNVTGVIPLTTTPTKSYFANLKGTRTRGKLCPDCLNCTDLDVALGRPMCVGTTPSAKASILHEVKPVTSG  (SEQ.ID.NO.156)
B/FLA/06 G141E DRICTGITSSNSPHVVKTATQGEVNVTGVIPLTTTPTKSYFANLKGTRTRGKLCPDCLNCTDLDVALGRPMCVGTTPSAKASILHEVRPVTSG  (SEQ.ID.NO.157)
B/JIN/03   DRICTGITSSNSPHVVKTATQGEVNVTGVIPLTTTPTKSYFANLKGTRTRGKLCPDCLNCTDLDVALGRPMCVGTTPSAKASILHEVRPVTSG  (SEQ.ID.NO.158)

100                 120                 140                 160                 180
                             |                   |                   |                   |                   |
B/MY/04    CFPIMHDRTKIRQLPNLLRGYEHIRLSTHNVINAENAPGGPYKIGTSGSCPNVTNGNGFFATMAWAVPKNDNNKTATNSLITEVPYICTEGED  (SEQ.ID.NO.155)
B/ELA/06   CFPIMHDRTKIRQLPNLLRGYENIRLSTQNVIDAEKAPGGPYRLGTSGSCPNATSKSGFFATMAWAVPK-DNNKNATNPLITVEVPYICTEGED  (SEQ.ID.NO.156)
B/FLA/06 G141E CFPIMHDRTKIRQLPNLLRGYENIRLSTQNVIDAEKAPGGPYRLGTSESCPNATSKSGFFATMAWAVPK-DNNKNATNPLITVEVPYICTEGED  (SEQ.ID.NO.157)
B/JIN/03   CFPIMHDRTKIRQLPNLLRGYENIRLSTQNVIDAENAPGGPYRLGTSRSCPNATSKSGFFATMAWAVPK-DNNKNATNPLITVEVPYICTEGED  (SEQ.ID.NO.158)
                                                       128           141    150
                            200                 220                 240                 260
                             |                   |                   |                   |
B/MY/04    QITVWGFHSDNEIQMAKLYGDSKPQKFTSSANGVTTHYVSQIGGFPNQTEEGLPQSGRIVVDYMVQKSGKTGTITYQRGILLPQKWCASGR  (SEQ.ID.NO.155)
B/ELA/06   QITVWGFHSDDKTQMKNLYGDSNPQKFTSSANGVTTHYVSQIGSFDQTEEGLPQSGRIVVDYMVQKPGKTGTIVQRGVLLPQKWCASGR  (SEQ.ID.NO.156)
B/FLA/06 G141E QITVWGFHSDDKTQMKNLYGDSNPQKFTSSANGVTTHYVSQIGSFDQTEEGLPQSGRIVVDYMVQKPGKTGTIVQRGVLLPQKWCASGR  (SEQ.ID.NO.157)
B/JIN/03   QITVWGFHSDNKTQMKNLYGDSNPQKFTSSANGVTTHYVSQIGGFPAQTEEGLPQSGRIVVDYMVQKPRKTGTIVQRGVLLPQKWCASGR  (SEQ.ID.NO.158)
                                                                    235

280                 300                 320                 340
                             |                   |                   |                   |
B/MY/04    SKVIKGSLPLIGEADCLHEKYGGLNKSKPYYTGEHAKAIGNCPIWVKTPLKLANGTKYRPPAKLLKER  (SEQ.ID.NO.155)
B/ELA/06   SKVIKGSLPLIGEADCLHEKYGGLNKSKPYYTGEHAKAIGNCPIWVKTPLKLANGTKYRPPAKLLKER  (SEQ.ID.NO.156)
B/FLA/06 G141E SKVIKGSLPLIGEADCLHEKYGGLNKSKPYYTGEHAKAIGNCPIWVKTPLKLANGTKYRPPAKLLKER  (SEQ.ID.NO.157)
B/JIN/03   SKVIKGSLPLIGEADCLHEKYGGLNKSKPYYTGEHAKAIGNCPIWVKTPLKLANGTKYRPPAKLLKER  (SEQ.ID.NO.158)
```

NEUTRALIZING ANTI-INFLUENZA B ANTIBODIES AND USES THEREOF

CROSS-REFERENCE TO RELATED APPLICATIONS

This application is a divisional of U.S. patent application Ser. No. 16/676,974, filed Nov. 7, 2019, which is a continuation of U.S. patent application Ser. No. 16/631,653, filed Mar. 22, 2019 and issued as U.S. Pat. No. 10,519,221, which is a divisional of U.S. patent application Ser. No. 15/325, 603, filed Jan. 11, 2017 and issued as U.S. Pat. No. 10,294, 292, which is a U.S. National Stage of International Application No. PCT/US2105/040385, filed on Jul. 14, 2015, said International Application No. PCT/US2015/040385 claims benefit under 35 U.S.C. § 119(e) of the U.S. Provisional Application No. 62/024,804, filed Jul. 15, 2014. Each of the above listed applications is incorporated by reference herein in its entirety for all purposes.

REFERENCE TO THE SEQUENCE LISTING

This application incorporates by reference a Sequence Listing submitted with this application as a text file entitled 0098_0031 US4_SL created on Oct. 8, 2021 and having a size of 89.2 kilobytes.

FIELD OF THE INVENTION

The invention relates to antibodies that have broad neutralizing activity against influenza B virus and to uses of such antibodies.

BACKGROUND TO THE INVENTION

Influenza viruses cause annual influenza epidemics and occasional pandemics, which pose a significant threat to public health worldwide. Seasonal influenza infection is associated with 200,000-500,000 deaths each year, particularly in young children, immunocompromised patients and the elderly. Mortality rates typically increase further during seasons with pandemic influenza outbreaks. There remains a significant unmet medical need for potent anti-viral therapeutics for preventing and treating influenza infections, particularly in under-served populations.

There are three types of influenza viruses: types A, B and C. The majority of influenza disease is caused by influenza A and B viruses (Thompson et al. (2004) JAMA. 292:1333-1340; and Zhou et al. (2012) Clin Infect. Dis. 54:1427-1436). The overall structure of influenza viruses A, B and C is similar, and includes a viral envelope which surrounds a central core. The viral envelope includes two surface glycoproteins, Hemagglutinin (HA) and neuraminidase (NA); HA mediates binding of the virus to target cells and entry into target cells, whereas NA is involved in the release of progeny virus from infected cells.

The HA protein is trimeric in structure and includes three identical copies of a single polypeptide precursor, HA0, which, upon proteolytic maturation, is cleaved into a pH-dependent, metastable intermediate containing a globular head (HA1) and stalk region (HA2) (Wilson et al. (1981) Nature. 289:366-373). The membrane distal globular head constitutes the majority of the HA1 structure and contains the sialic acid binding pocket for viral entry and major antigenic domains.

Influenza A viruses can be classified into subtypes based on genetic variations in hemagglutinin (HA) and neuraminidase (NA) genes. Currently, in seasonal epidemics, influenza A H1 and H3 HA subtypes are primarily associated with human disease, whereas viruses encoding H5, H7, H9 and H10 are associated with sporadic human outbreaks due to direct transmission from animals.

In contrast to influenza A viruses, influenza B viruses are not divided into subtypes based on the two surface glycoproteins and until the 1970s were classified as one homogenous group. Through the 1970s, the influenza B viruses started to diverge into two antigenically distinguishable lineages which were named the Victoria and Yamagata lineages after their first representatives, B/Victoria/2/87 and B/Yamagata/16/88, respectively. (Biere et al. (2010) J Clin Microbiol. 48(4):1425-7; doi: 10.1128/JCM.02116-09. Epub 2010 Jan. 27). Influenza B viruses are restricted to human infection, and both lineages contribute to annual epidemics. Although the morbidity caused by influenza B viruses is lower than that associated with influenza A H3N2, it is higher than that associated with influenza A H1N1 (Zhou et al. (2012) Clin Infect. Dis. 54:1427-1436).

Neutralizing antibodies elicited by influenza virus infection are normally targeted to the variable HA1 globular head to prevent viral receptor binding and are usually strain-specific. Broadly cross-reactive antibodies that neutralize one or more subtype or lineage are rare. Recently, a few human antibodies have been discovered that can neutralize multiple subtypes of influenza B viruses of both lineages (Dreyfus et al. (2012) Science. 337(6100):1343-8; and Yasugi et al. (2013) PLoS Path. 9(2):e1003150). Although these antibodies recognize many influenza B viruses, they have a limited breadth of coverage and potency, and do not neutralize any influenza A virus strains. To date, there are no available antibodies that broadly neutralize or inhibit all influenza B virus infections or attenuate diseases caused by influenza B virus. Therefore, there is a need to identify new antibodies that protect against multiple of influenza viruses.

SUMMARY OF THE INVENTION

The invention described herein provides an isolated antibody or an antigen binding fragment thereof that is capable of binding to influenza B virus hemagglutinin (HA) and neutralizing influenza B virus in two phylogenetically distinct lineages. In one embodiment, the antibody or antigen binding fragment thereof is capable of binding to influenza B virus hemagglutinin and neutralizing influenza B virus in both Yamagata and Victoria lineages. Yamagata lineages include, but are not limited to: B/AA/94 (ca B/Ann Arbor/ 2/94 (yamagata)); B/YSI/98 (ca B/Yamanashi/166/98 (yamagata)); B/JHB/99 (ca B/Johannesburg/5/99 (yamagata)); B/SC/99 (B/Sichuan/379/99 (yamagata)); B/FL/06 (B/Florida/4/2006 (yamagata)). Victoria lineages include, but are not limited to: B/BJ/97 (ca B/Beijing/243/97 (victoria)), B/HK/01 (B/Hong Kong/330/2001 (victoria)); B/MY/04 (B/Malaysia/2506/2004 (victoria)); B/BNE/08 (ca B/Brisbane/60/2008 (victoria)).

In another embodiment, the invention provides an isolated antibody or an antigen binding fragment thereof that is capable of binding to influenza B virus hemagglutinin and neutralizing influenza B virus in a pre-divergent strain. As used herein, the term "pre-divergent" refers to influenza B strains that were identified prior to the divergence of influenza B into Yamagata and Victoria lineages. Pre-divergent influenza B strains include, but are not limited to: B/Lee/40 (B/Lee/40); B/AA/66 (ca B/Ann Arbor/1/66); and B/HK/72 (B/Hong Kong/5/72).

In one embodiment, the antibody or antigen binding fragment binds influenza B virus with an $EC_{50}$ in the range of from about 1 µg/ml to about 50 µg/ml of antibody. In another embodiment, the antibody or antigen binding fragment has a neutralizing potency expressed as 50% inhibitory concentration ($IC_{50}$ µg/ml) in the range of from about 0.001 µg/ml to about 5 µg/ml of antibody for neutralization of influenza B virus in a microneutralization assay as described in Example 3. Other microneutralization assays are also described in Example 1.

In one embodiment, the antibody is capable of binding to influenza A virus hemagglutinin. Influenza A virus hemagglutinin includes subtype 1 and subtype 2 hemagglutinin. Influenza A virus group 1 subtypes include: H1, H2, H5, H6, H8, H9, H11, H12, H13, H16 and variants thereof. Influenza A virus group 2 subtype include: H3, H4, H7, H10, H14 and H15 and variants thereof. In one embodiment, the antibody is capable of binding to one or more influenza A virus group 1 subtypes. In another embodiment, the antibody is capable of binding to one or more influenza A virus group 2 subtypes. In one embodiment, the antibody is capable of binding to influenza A virus group 1 subtype H9. In one embodiment, the invention provides an isolated antibody or an antigen binding fragment thereof that is capable of binding to influenza B virus hemagglutinin (HA) and influenza A virus hemagglutinin (HA) and neutralizing at least one Yamagata lineage influenza B virus; at least one Victoria lineage influenza B virus; at least one influenza A virus subtype, or combinations thereof. In one embodiment, the invention provides an isolated antibody or an antigen binding fragment thereof that is capable of binding to influenza B virus hemagglutinin (HA) and one or more influenza A virus subtype 1 hemagglutinin (HA) and neutralizing at least one Yamagata lineage influenza B virus or at least one Victoria lineage influenza B virus and at least one influenza A virus subtype 1. In one embodiment, the invention provides an isolated antibody or an antigen binding fragment thereof that is capable of binding to influenza B virus hemagglutinin (HA) and influenza A virus subtype H9 hemagglutinin (HA) and neutralizing at least one Yamagata lineage influenza B virus; at least one Victoria lineage influenza B virus; influenza A virus subtype H9, or combinations thereof.

In one embodiment, the antibody or antigen binding fragment binds influenza A HA at an $EC_{50}$ in the range of from about 1 µg/ml to about 50 µg/ml of antibody. In another embodiment, the antibody or antigen binding fragment has an $IC_{50}$ in the range of from about 0.01 µg/ml to about 5 µg/ml of antibody for neutralization of influenza A virus in a microneutralization assay.

In one embodiment, an antibody or fragment thereof of the invention binds to the globular head region of HA and neutralizes infection of influenza B virus in two phylogenetically distinct lineages. In another embodiment, the antibody or antigen binding fragment thereof binds to the globular head region of HA and neutralizes infection of influenza B virus from both Yamagata and Victoria lineages. Antibodies of the invention, which are anti-Influenza B HA globular head binding antibodies, demonstrate a broader breath of coverage or better neutralizing activity against influenza B viruses compared to known anti-influenza B antibodies.

In one embodiment, the antibody or antigen binding fragment thereof includes a set of six CDRs: HCDR-1, HCDR-2, HCDR-3, LCDR-1, LCDR-2, LCDR-3, in which the set of six CDRs is selected from:

(a) HCDR-1 of SEQ ID NO.: 3, HCDR-2 of SEQ ID NO.: 4, HCDR-3 of SEQ ID NO.: 5, LCDR-1 of SEQ ID NO.: 8, LCDR-2 of SEQ ID NO.: 9 and LCDR-3 of SEQ ID NO.: 10;

(b) HCDR-1 of SEQ ID NO.: 13, HCDR-2 of SEQ ID NO.: 14, HCDR-3 of SEQ ID NO.: 15, LCDR-1 of SEQ ID NO.: 18, LCDR-2 of SEQ ID NO.: 19, LCDR-3 of SEQ ID NO.: 20;

(c) HCDR-1 of SEQ ID NO.: 23, HCDR-2 of SEQ ID NO.: 24, HCDR-3 of SEQ ID NO.: 25, LCDR-1 of SEQ ID NO.: 28, LCDR-2 of SEQ ID NO.: 29 and LCDR-3 of SEQ ID NO.: 30;

(d) HCDR-1 of SEQ ID NO.: 33, HCDR-2 of SEQ ID NO.: 34, HCDR-3 of SEQ ID NO.: 35, LCDR-1 of SEQ ID NO.: 38, LCDR-2 of SEQ ID NO.: 39 and LCDR-3 of SEQ ID NO.: 40;

(e) HCDR-1 of SEQ ID NO.: 43, HCDR-2 of SEQ ID NO.: 44, HCDR-3 of SEQ ID NO.: 45, LCDR-1 of SEQ ID NO.: 48, LCDR-2 of SEQ ID NO.: 49 and LCDR-3 of SEQ ID NO.: 50;

(f) HCDR-1 of SEQ ID NO.: 53, HCDR-2 of SEQ ID NO.: 54, HCDR-3 of SEQ ID NO.: 55, LCDR-1 of SEQ ID NO.: 58, LCDR-2 of SEQ ID NO.: 59 and LCDR-3 of SEQ ID NO.: 60;

(g) HCDR-1 of SEQ ID NO.: 63, HCDR-2 of SEQ ID NO.: 64, HCDR-3 of SEQ ID NO.: 65, LCDR-1 of SEQ ID NO.: 68, LCDR-2 of SEQ ID NO.: 69 and LCDR-3 of SEQ ID NO.: 70;

(h) HCDR-1 of SEQ ID NO.: 75, HCDR-2 of SEQ ID NO.: 76, HCDR-3 of SEQ ID NO.: 77, LCDR-1 of SEQ ID NO.: 83, LCDR-2 of SEQ ID NO.: 84 and LCDR-3 of SEQ ID NO.: 85;

(i) HCDR-1 of SEQ ID NO.: 91, HCDR-2 of SEQ ID NO.: 92, HCDR-3 of SEQ ID NO.: 93, LCDR-1 of SEQ ID NO.: 99, LCDR-2 of SEQ ID NO.: 100 and LCDR-3 of SEQ ID NO.: 101;

(j) HCDR-1 of SEQ ID NO.: 107, HCDR-2 of SEQ ID NO.: 108, HCDR-3 of SEQ ID NO.: 109, LCDR-1 of SEQ ID NO.: 115, LCDR-2 of SEQ ID NO.: 116 and LCDR-3 of SEQ ID NO.: 117;

(k) HCDR-1 of SEQ ID NO.: 121, HCDR-2 of SEQ ID NO.: 122, HCDR-3 of SEQ ID NO.: 123, LCDR-1 of SEQ ID NO.: 124, LCDR-2 of SEQ ID NO.: 125 and LCDR-3 of SEQ ID NO.: 126;

(l) HCDR-1 of SEQ ID NO.: 127, HCDR-2 of SEQ ID NO.: 128, HCDR-3 of SEQ ID NO.: 129, LCDR-1 of SEQ ID NO.: 130, LCDR-2 of SEQ ID NO.: 131 and LCDR-3 of SEQ ID NO.: 132;

(m) HCDR-1 of SEQ ID NO.: 133, HCDR-2 of SEQ ID NO.: 134, HCDR-3 of SEQ ID NO.: 135, LCDR-1 of SEQ ID NO.: 136, LCDR-2 of SEQ ID NO.: 137 and LCDR-3 of SEQ ID NO.: 138;

(n) HCDR-1 of SEQ ID NO.: 139, HCDR-2 of SEQ ID NO.: 140, HCDR-3 of SEQ ID NO.: 141, LCDR-1 of SEQ ID NO.: 142, LCDR-2 of SEQ ID NO.: 143 and LCDR-3 of SEQ ID NO.: 144;

(o) HCDR-1 of SEQ ID NO.: 145, HCDR-2 of SEQ ID NO.: 146, HCDR-3 of SEQ ID NO.: 147, LCDR-1 of SEQ ID NO.: 148, LCDR-2 of SEQ ID NO.: 149 and LCDR-3 of SEQ ID NO.: 150;

(p) HCDR-1 of SEQ ID NO.: 78, HCDR-2 of SEQ ID NO.: 79, HCDR-3 of SEQ ID NO.: 80, LCDR-1 of SEQ ID NO.: 86, LCDR-2 of SEQ ID NO.: 87 and LCDR-3 of SEQ ID NO.: 88;

(q) HCDR-1 of SEQ ID NO.: 94, HCDR-2 of SEQ ID NO.: 95, HCDR-3 of SEQ ID NO.: 96, LCDR-1 of SEQ ID NO.: 102, LCDR-2 of SEQ ID NO.: 103 and LCDR-3 of SEQ ID NO.: 104;

(r) HCDR-1 of SEQ ID NO.: 110, HCDR-2 of SEQ ID NO.: 111, HCDR-3 of SEQ ID NO.: 112, LCDR-1 of SEQ ID NO.: 118, LCDR-2 of SEQ ID NO.: 119 and LCDR-3 of SEQ ID NO.: 120; and (s) a set of six CDRS according to any one of (a) to (r) including one or more amino acid substitutions, deletions or insertions.

In another embodiment, antibody or antigen binding fragment thereof has a VH having at least 75%, 80%, 85%, 90%, 95% or 100% identity and/or a VL having at least 75%, 80%, 85%, 90%, 95% or 100% identity to a VH and/or VL, respectively, selected from:

(a) VH of SEQ ID NO.: 2 and VL of SEQ ID NO.: 7,
(b) VH of SEQ ID NO.: 12 and VL of SEQ ID NO.: 17,
(c) VH of SEQ ID NO.: 22 and VL of SEQ ID NO.: 27,
(d) VH of SEQ ID NO.: 32 and VL of SEQ ID NO.: 37,
(e) VH of SEQ ID NO.: 42 and VL of SEQ ID NO.: 47,
(f) VH of SEQ ID NO.: 52 and VL of SEQ ID NO.: 57,
(g) VH of SEQ ID NO.: 62 and VL of SEQ ID NO.: 67,
(h) VH of SEQ ID NO.: 74 and VL of SEQ ID NO.: 82,
(i) VH of SEQ ID NO.: 90 and VL of SEQ ID NO.: 98, and
(j) VH of SEQ ID NO.: 106 and VL of SEQ ID NO.: 114.

In a more particular embodiment, the antibody or antigen binding fragment thereof includes a VH and a VL selected from:

(a) VH of SEQ ID NO.: 2 and VL of SEQ ID NO.: 7,
(b) VH of SEQ ID NO.: 12 and VL of SEQ ID NO.: 17,
(c) VH of SEQ ID NO.: 22 and VL of SEQ ID NO.: 27,
(d) VH of SEQ ID NO.: 32 and VL of SEQ ID NO.: 37,
(e) VH of SEQ ID NO.: 42 and VL of SEQ ID NO.: 47,
(f) VH of SEQ ID NO.: 52 and VL of SEQ ID NO.: 57,
(g) VH of SEQ ID NO.: 62 and VL of SEQ ID NO.: 67,
(h) VH of SEQ ID NO.: 74 and VL of SEQ ID NO.: 82,
(i) VH of SEQ ID NO.: 90 and VL of SEQ ID NO.: 98, and
(j) VH of SEQ ID NO.: 106 and VL of SEQ ID NO.: 114.

In one embodiment, the invention provides an antibody or antigen binding fragment thereof that is capable of binding to influenza B virus hemagglutinin (HA) and neutralizing influenza B virus in two phylogenetically distinct lineages, wherein the antibody has a VH amino acid sequence of SEQ ID NO:71, wherein $Xaa_1$ of SEQ ID NO:71 is Val or Glu; $Xaa_2$ SEQ ID NO:71 is Leu or Phe; $Xaa_3$ SEQ ID NO:71 is Ser or Thr; $Xaa_4$ SEQ ID NO:71 is Leu or Ser; $Xaa_5$ SEQ ID NO:71 is Ser or Thr; $Xaa_6$ SEQ ID NO:71 is Met or Thr; $Xaa_7$ SEQ ID NO:71 is Phe or Tyr; $Xaa_8$ SEQ ID NO:71 is His or Gln; $Xaa_9$ SEQ ID NO:71 is Ser or Asn; $Xaa_{10}$ SEQ ID NO:71 is Arg or Lys; and $Xaa_{11}$ SEQ ID NO:71 is Ala or Thr; and an VL amino acid sequence of SEQ ID NO:72, wherein $Xaa_1$ of SEQ ID NO:72 is Phe or Tyr. In one embodiment, $Xaa_9$ of SEQ ID NO:71 is Ser. In another embodiment, $Xaa_4$ of SEQ ID NO:71 is Leu. In yet another embodiment, $Xaa_1$ of SEQ ID NO:71 is Glu; $Xaa_5$ of SEQ ID NO:71 is Thr; $Xaa_6$ of SEQ ID NO:71 is Thr; $Xaa_7$ of SEQ ID NO:71 is Tyr; $Xaa_8$ of SEQ ID NO:71 is Gln; $Xaa_{10}$ of SEQ ID NO:71 is Lys; $Xaa_{11}$ of SEQ ID NO:71 is Thr, or combinations thereof. In another embodiment, $Xaa_1$ of SEQ ID NO:71 is Glu, $Xaa_5$ of SEQ ID NO:71 is Thr; $Xaa_6$ of SEQ ID NO:71 is Thr; $Xaa_7$ of SEQ ID NO:71 is Tyr; $Xaa_8$ of SEQ ID NO:71 is Gln; $Xaa_9$ of SEQ ID NO:71 is Ser; $Xaa_{10}$ of SEQ ID NO:71 is Lys; and $Xaa_{11}$ of SEQ ID NO:71 is Thr.

In one embodiment, the antibody or antigen binding fragment thereof is selected from: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual-specific antibody, and a bispecific antibody. In one embodiment, the antibody or antigen binding fragment thereof includes an Fc region. In one embodiment, the antibody or antigen binding fragment thereof is an IgG1, IgG2 or IgG4 or fragment thereof.

In one embodiment, the invention provides an antibody to influenza B virus or an antigen binding fragment thereof that is capable of binding to influenza B virus and neutralizing at least one Yamagata lineage and at least one Victoria lineage of influenza B virus, wherein the antibody or antigen binding fragment thereof binds an epitope that is conserved among at least one Yamagata lineage, and at least one Victoria lineage of influenza B virus. In one embodiment, one or more contact residues of the epitope are located in a head region of influenza B HA. In one embodiment, the epitope includes one or more amino acids selected from: 128, 141, 150 and 235 of the sequence of the head region of HA as contact residues (Wang et al. (2008) J. Virol. 82(6):3011-20).

In another embodiment, the invention provides an antibody to influenza B virus or an antigen binding fragment thereof that is capable of binding to influenza B virus hemagglutinin and neutralizing influenza B virus in two phylogenetically distinct lineages that binds to the same epitope as or competes for binding to influenza B virus hemagglutinin with an antibody of the invention. In one embodiment, the antibody or antigen binding fragment binds to the same epitope or competes for binding to influenza A virus hemagglutinin with an antibody having an amino acid sequence selected from:

(a) VH of SEQ ID NO.: 2 and VL of SEQ ID NO.: 7,
(b) VH of SEQ ID NO.: 12 and VL of SEQ ID NO.: 17,
(c) VH of SEQ ID NO.: 22 and VL of SEQ ID NO.: 27,
(d) VH of SEQ ID NO.: 32 and VL of SEQ ID NO.: 37,
(e) VH of SEQ ID NO.: 42 and VL of SEQ ID NO.: 47,
(f) VH of SEQ ID NO.: 52 and VL of SEQ ID NO.: 57,
(g) VH of SEQ ID NO.: 62 and VL of SEQ ID NO.: 67,
(h) VH of SEQ ID NO.: 74 and VL of SEQ ID NO.: 82,
(i) VH of SEQ ID NO.: 90 and VL of SEQ ID NO.: 98, and
(j) VH of SEQ ID NO.: 106 and VL of SEQ ID NO.: 114.

The invention also provides an isolated nucleic acid encoding an antibody or antigen binding fragment thereof of the invention, as well as a vector that includes such an isolated nucleic acid and a host cell that includes such a nucleic acid or vector. In one embodiment, the vector is an expression vector. In another embodiment, the vector is a non-naturally occurring recombinant vector. In one embodiment, the vector is a plasmid. In one embodiment, the vector or plasmid includes a nucleotide sequence encoding an antibody molecule of the invention, or antigen binding fragment thereof, a heavy or light chain of an antibody molecule of the invention, a heavy or light chain variable domain of an antibody of the invention, or a portion thereof, or a heavy or light chain CDR, operably linked to one or more expression control elements (e.g., promoter, enhancer, transcription terminators, polyadenylation sites, etc.), a selectable marker gene, or combinations thereof. In one embodiment, the vector or plasmid includes at least one heterologous expression control element, selectable marker, or combinations thereof.

In one embodiment, the invention provides a method for manufacturing an antibody or antigen binding fragment thereof by culturing a host cell described herein under conditions suitable for expression of the antibody or fragment thereof. In one embodiment, the method includes isolating the antibody or antigen binding fragment thereof from the host cell culture. In one embodiment the host cell is isolated from tissues in which the cell is naturally found. For example, a host cell can be isolated from an organism and maintained ex vivo in a cell culture.

The invention also provides a composition that includes an antibody or antigen binding fragment thereof of the invention and a pharmaceutically acceptable carrier. In one embodiment, the composition includes an antibody or antigen binding fragment thereof of the invention and 25 mM His and 0.15M NaCl at pH 6.0

In one embodiment, the antibody or antigen binding fragment thereof of the invention is used in the prophylaxis or treatment of influenza B infection in a subject. In another embodiment, the antibody or antigen binding fragment thereof is used in the prophylaxis or treatment of influenza A and influenza B infection in a subject. In another embodiment, the antibody or antigen binding fragment thereof of the invention is used in the manufacture of a medicament for the prophylaxis or treatment of influenza B infection in a subject. In another embodiment, the antibody or antigen binding fragment thereof of the invention is used in the manufacture of a medicament for the prophylaxis or treatment of influenza A and influenza B infection in a subject.

In one embodiment, the invention provides a method for prophylaxis or treatment of influenza B infection in a subject, which includes administering an effective amount of an antibody or antigen binding fragment thereof of the invention to the subject. In another embodiment, the invention provides method for prophylaxis or treatment of influenza A and influenza B infection in a subject, which includes administering an effective amount of an antibody or antigen binding fragment thereof of the invention to the subject.

In one embodiment, the antibody or fragment thereof of the invention is used for in vitro diagnosis of influenza B infection in a subject. In another embodiment, the antibody or fragment thereof of the invention is used for in vitro diagnosis of influenza A infection in a subject. In yet another embodiment, the antibody or fragment thereof of the invention is used for in vitro diagnosis of influenza A infection and influenza B infection in a subject.

BRIEF DESCRIPTION OF THE FIGURES

FIG. 1 shows the antibody-dependent cellular cytotoxicity (ADCC) as measured by NK cell activation after incubation with B/HongKong/330/2001 (Victoria lineage) and a serial dilution of anti-HA antibodies FBD-94 and FBC-39, as well as variants that lack Fc-effector function (FBD-94 LALA and FBC-39 LALA).

FIG. 5A shows the CDRs (boxed) within the VH sequences of anti-influenza B antibodies FBD-56 (SEQ. ID. NO. 2), FBD-94 (SEQ. ID. NO. 12), FBC-39 (SEQ. ID. NO. 22), FBC-39 LSL (SEQ. ID. NO. 32), FBC-39 FSL (SEQ. ID. NO. 42), FBC-39 LTL (SEQ. ID. NO. 52), FBC-39 FTL (SEQ. ID. NO. 62), FBC-39 FSS (SEQ. ID. NO. 74), FBC-39 LTS (SEQ. ID. NO. 90), and FBC-39 FTS (SEQ. ID. NO. 106) using the Kabat numbering system. Modified amino acids within the VH sequences are bolded and underlined.

FIG. 5B shows the CDRs (boxed) within the VL sequences of anti-influenza B antibodies FBD-56 (SEQ. ID. NO. 7), FBD-94 (SEQ. ID. NO. 17), FBC-39 (SEQ. ID. NO. 27), FBC-39 LSL (SEQ. ID. NO. 37), FBC-39 FSL (SEQ. ID. NO. 47), FBC-39 LTL (SEQ. ID. NO. 57), FBC-39 FTL (SEQ. ID. NO. 67), FBC-39 FSS(SEQ. ID. NO. 82), FBC-39 LTS(SEQ. ID. NO. 98), and FBC-39 FTS (SEQ. ID. NO. 114) using the Kabat numbering system. Modified amino acids within the VH sequences are bolded and underlined.

FIG. 5C shows the CDRs (boxed) within the VH sequences of anti-influenza B antibodies FBD-56 (SEQ. ID. NO. 2), FBD-94 (SEQ. ID. NO. 12), FBC-39 (SEQ. ID. NO. 22), FBC-39 LSL (SEQ. ID. NO. 32), FBC-39 FSL (SEQ. ID. NO. 42), FBC-39 LTL (SEQ. ID. NO. 52), FBC-39 FTL (SEQ. ID. NO. 62), FBC-39 FSS (SEQ. ID. NO. 74), FBC-39 LTS (SEQ. ID. NO. 90), and FBC-39 FTS (SEQ. ID. NO. 106) using the IMGT numbering system. Modified amino acids within the VH sequences are bolded and underlined.

FIG. 5D shows the CDRs (boxed) within the VL sequences of anti-influenza B antibodies FBD-56 (SEQ. ID. NO. 7), FBD-94 (SEQ. ID. NO. 17), FBC-39 (SEQ. ID. NO. 27), FBC-39 LSL (SEQ. ID. NO. 37), FBC-39 FSL (SEQ. ID. NO. 47), FBC-39 LTL (SEQ. ID. NO. 57), FBC-39 FTL (SEQ. ID. NO. 67), FBC-39 FSS (SEQ. ID. NO. 82), FBC-39 LTS (SEQ. ID. NO. 90), and FBC-39 FTS (SEQ. ID. NO. 106) using the IMGT numbering system. Modified amino acids within the VL sequences are bolded and underlined.

FIG. 6 shows the heavy chain amino acid sequence of a genericized anti-influenza B antibody (SEQ ID NO:71), based on the heavy chain amino acid sequence of FBC-39 (SEQ ID NO:22), wherein $Xaa_1$ can be Val or Glu; $Xaa_2$ can be Leu or Phe; $Xaa_3$ can be Thr or Ser; $Xaa_4$ can be Ser or Leu; $Xaa_5$ can be Thr or Ser; $Xaa_6$ can be Thr or Met; $Xaa_7$ can be Tyr or Phe; $Xaa_8$ can be Gln or His; $Xaa_9$ can be Asn or Ser; $Xaa_{10}$ can be Lys or Arg; and $Xaa_{11}$ can be Thr or Ala.

FIG. 7 shows the light chain amino acid sequence of a genericized anti-influenza B antibody (SEQ ID NO:72), based on the light chain amino acid sequence of FBC-39 (SEQ ID NO:27), wherein $Xaa_1$ can be Phe or Tyr.

FIG. 8 shows the alignment of the HA1 proteins from the viruses used in the monoclonal antibody resistant mutant (MARM) isolation: B/MY/04 (SEQ. ID. NO. 155), B/FLA/06 (SEQ. ID. NO. 156), B/FLA/06 G141E (SEQ. ID. NO. 157), and B/JIN/03 (SEQ. ID. NO. 158). Amino acid positions found to be contact residues through MARM selection are boxed.

DETAILED DESCRIPTION

Introduction

Figure 2A:
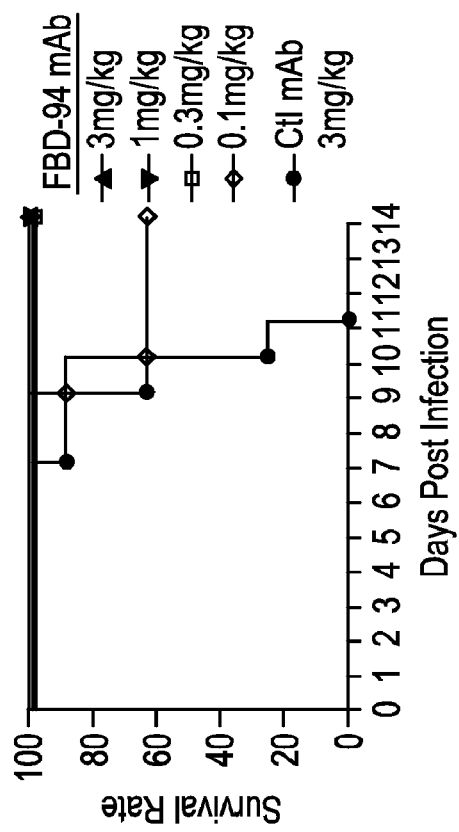
FIG. 2A shows the percentage of surviving animals that were administered with different concentrations of FBC-39 and a non-relevant control antibody 4 hours before infection with a lethal dose of B/Sichuan/379/99 (Yamagata) influenza virus.
Figure 2C:
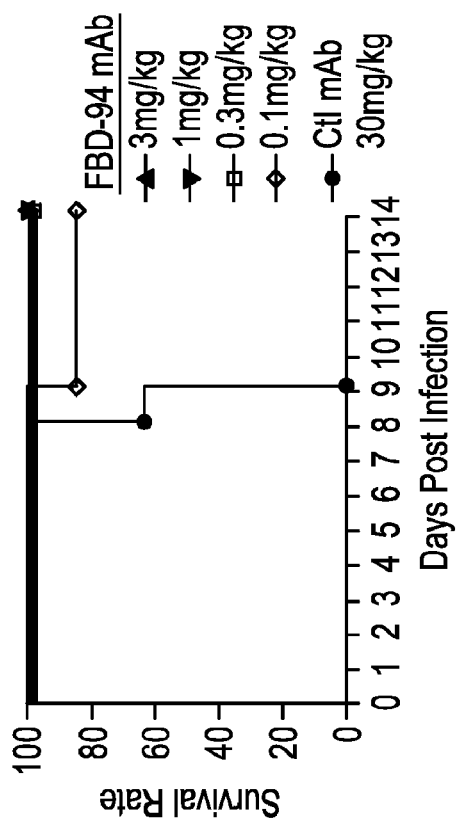
FIG. 2C shows the percentage of surviving animals that were administered with different concentrations of FBC-39 and a non-relevant control antibody 4 hours before infection with a lethal dose of B/Hong Kong/330/2001 (Victoria) influenza virus.
Figure 2B:
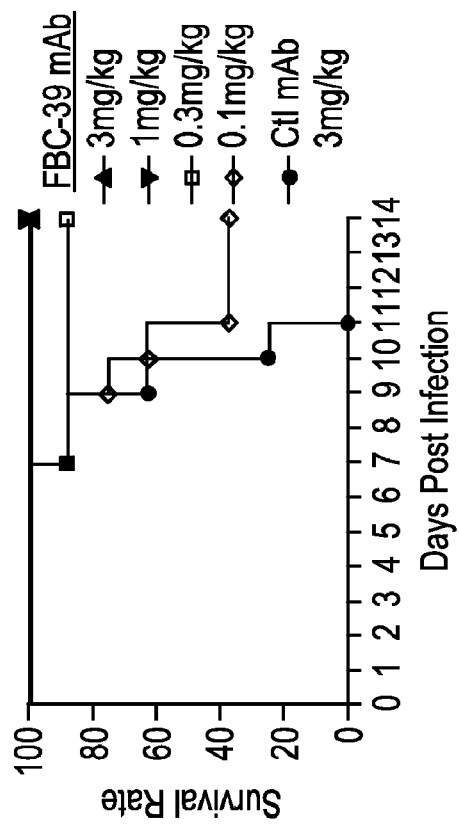
FIG. 2B shows the percentage of surviving animals that were administered with different concentrations of FBD-94 and a non-relevant control antibody 4 hours before infection with a lethal dose of B/Sichuan/379/99 (Yamagata) influenza virus.
Figure 2D:
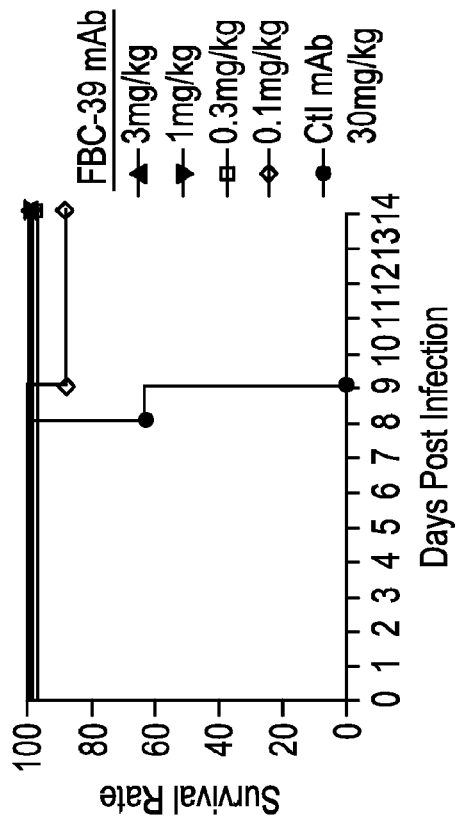
FIG. 2D shows the percentage of surviving animals that were administered with different concentrations of FBD-94 and a non-relevant control antibody 4 hours before infection with a lethal dose of B/Hong Kong/330/2001 (Victoria) influenza virus.
Figure 3A:
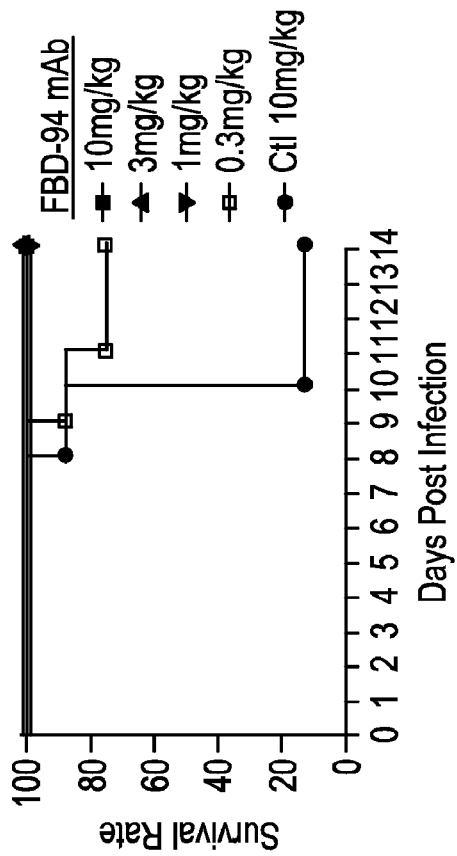
FIG. 3A shows the percentage of surviving animals that were infected with a lethal dose of B/Sichuan/379/99 (Yamagata) and treated on day 2 post-infection with different doses of FBC-39, or a non-relevant control antibody.
Figure 3C:
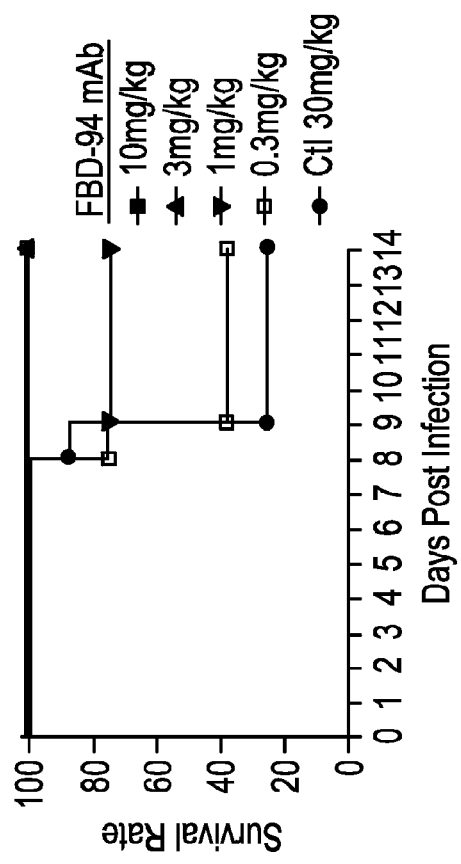
FIG. 3C shows the percentage of surviving animals that were infected with a lethal dose of B/Hong Kong/330/2001 (Victoria) and treated on day 2 post-infection with different doses of FBC-39, or a non-relevant control antibody.
Figure 3B:
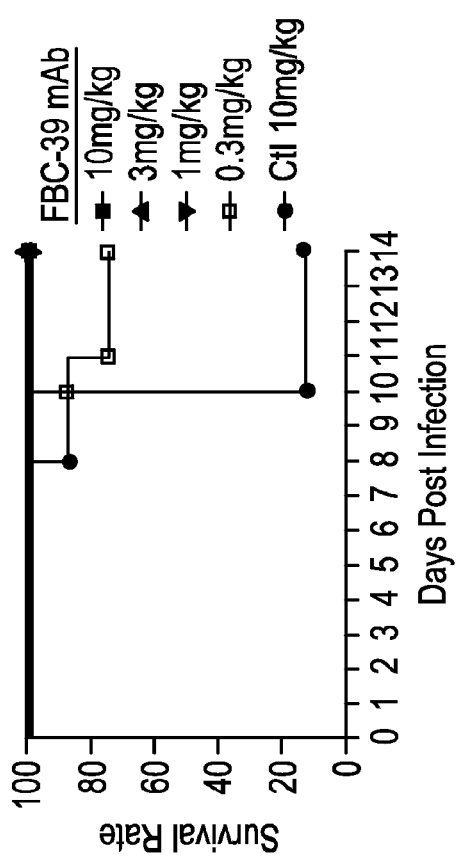
FIG. 3B shows the percentage of surviving animals that were infected with a lethal dose of B/Sichuan/379/99 (Yamagata) and treated on day 2 post-infection with different doses of FBD-94, or a non-relevant control antibody.
Figure 3D:
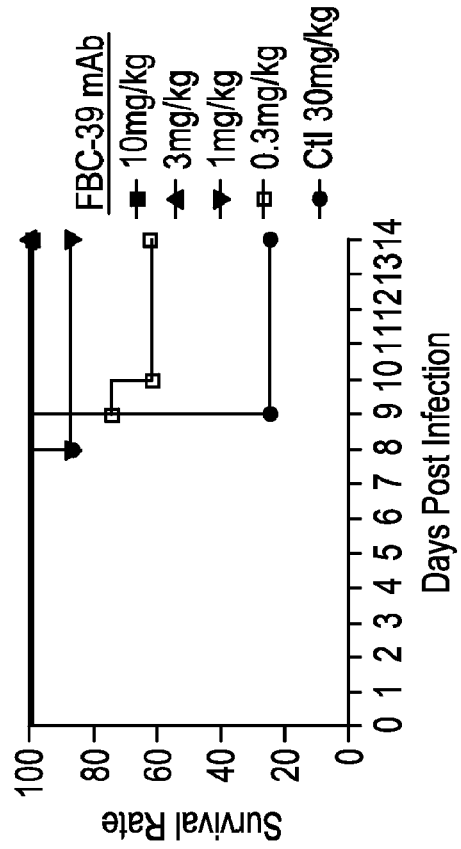
FIG. 3D shows the percentage of surviving animals that were infected with a lethal dose of B/Hong Kong/330/2001 (Victoria) and treated on day 2 post-infection with different doses of FBD-94, or a non-relevant control antibody.
Figure 4A:
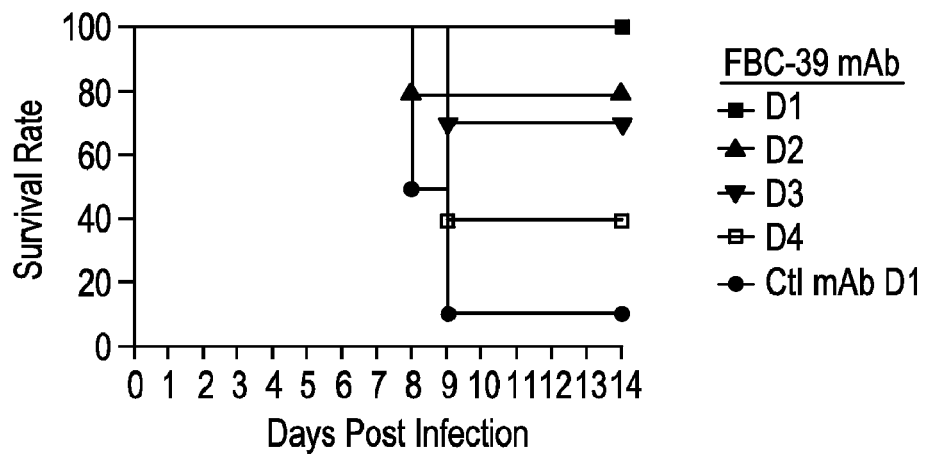
FIG. 4A shows the percentage of surviving animals that were infected with a lethal dose of B/Hong Kong/330/2001 (Victoria) and treated at 1, 2, 3, or 4 days post-infection with 3 mg/kg of FBC-39, or a non-relevant control antibody.
Figure 4B:
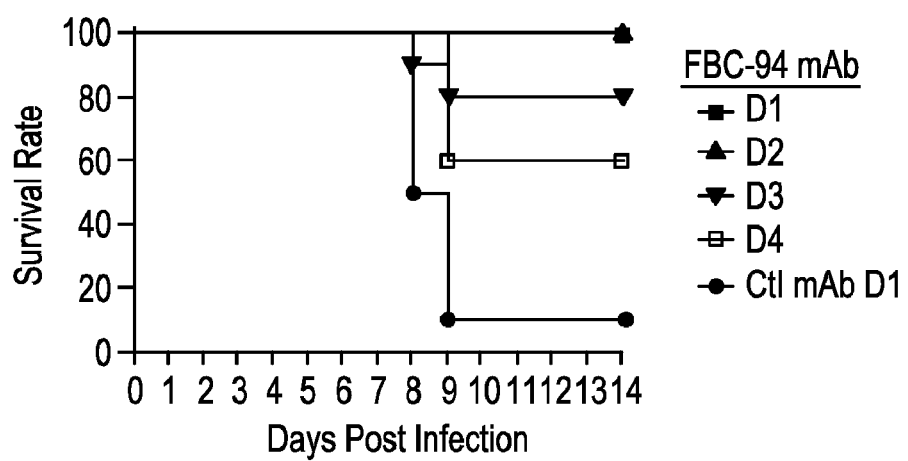
FIG. 4B shows the percentage of surviving animals that were infected with a lethal dose of B/Hong Kong/330/2001 (Victoria) and treated at 1, 2, 3, or 4 days post-infection with 3 mg/kg of FBD-94, or a non-relevant control antibody.

The present invention provides antibodies, including human forms, as well as antigen binding fragments, derivatives/conjugates and compositions thereof that bind to influenza B virus hemagglutinin (HA) and neutralize influenza B virus in two phylogenetically distinct lineages as described herein. In one embodiment, the antibodies or antigen binding fragments thereof bind to influenza B virus hemagglutinin (HA) and neutralize influenza B virus in both Yamagata and Victoria lineages as described herein; such anti-influenza B antibodies and fragments thereof are referred to herein as antibodies of the invention. In another embodiment, the antibodies or antigen binding fragments thereof bind influenza B virus hemagglutinin (HA) and influenza A virus hemagglutinin (HA) and neutralize at least one Yamagata lineage influenza B virus; at least one Victoria lineage influenza B virus; at least one influenza A virus subtype, or combinations thereof. Such anti-influenza B antibodies and fragments thereof are also referred to herein as antibodies of the invention.

As used herein, the term "neutralize" refers to the ability of an antibody, or antigen binding fragment thereof, to bind to an infectious agent, such as influenza A and/or B virus, and reduce the biological activity, for example, virulence, of the infectious agent. In one embodiment, the antibody or antigen binding fragment thereof of the invention immunospecifically binds at least one specified epitope or antigenic determinant of the influenza A virus; influenza B virus, or combinations thereof. In a more particular embodiment, the antibody or antigen binding fragment thereof of the invention immunospecifically binds at least one specified epitope or antigenic determinant of influenza B virus hemagglutinin (HA). In another more particular embodiment, the antibody or binding fragment thereof of the invention immunospecifically binds at least one specified epitope or antigenic determinant of the Influenza B virus HA globular head.

An antibody can neutralize the activity of an infectious agent, such as influenza A and/or influenza B virus at various points during the lifecycle of the virus. For example, an antibody may interfere with viral attachment to a target cell by interfering with the interaction of the virus and one or more cell surface receptors. Alternately, an antibody may interfere with one or more post-attachment interactions of the virus with its receptors, for example, by interfering with viral internalization by receptor-mediated endocytosis.

As used herein, the terms "antibody" and "antibodies", also known as immunoglobulins, encompass monoclonal antibodies (including full-length monoclonal antibodies), human antibodies, humanized antibodies, camelid antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)).

Human antibodies are usually heterotetrameric glycoproteins of about 150,000 daltons, which include two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains (CH). Each light chain has a variable domain at one end (VL) and a constant domain (CL) at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK.

The antibodies of the invention include full length or intact antibody, antibody fragments, including antigen binding fragments, native sequence antibody or amino acid variants, human, humanized, post-translationally modified, chimeric or fusion antibodies, immunoconjugates, and functional fragments thereof. The antibodies can be modified in the Fc region to provide desired effector functions or serum half-life. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity (CDC), or by recruiting nonspecific cytotoxic cells that express one or more effector ligands that recognize bound antibody on the influenza A and/or influenza B virus and subsequently cause phagocytosis of the cell in antibody dependent cell-mediated phagocytosis (ADCP), or some other mechanism. Alternatively, where it is desirable to eliminate or reduce effector function, so as to minimize side effects or therapeutic complications, certain other Fc regions may be used. Methods for enhancing as well as reducing or eliminating Fc-effector function are described herein. Additionally, the Fc region of the antibodies of the invention can be modified to increase the binding affinity for FcRn and thus increase serum half-life. Alternatively, the Fc region can be conjugated to PEG or albumin to increase the serum half-life, or some other conjugation that results in the desired effect.

In one embodiment, the antibodies are useful for diagnosing, preventing, treating and/or alleviating one or more symptoms of influenza B virus infection in a mammal. In another embodiment, the antibodies are useful for diagnosing, preventing, treating and/or alleviating one or more symptoms of influenza A and influenza B virus infection in an animal. As used herein the term "animal" refers to mammals including, but not limited to, humans, non-human primates, dogs, cats, horses, rabbits, mice, and rats; and non-mammalian species, including, but not limited to, avian species such as chickens, turkeys, ducks, and quail.

The invention provides a composition that includes an antibody of the invention and a carrier. For the purposes of preventing or treating influenza B virus infection, compositions can be administered to the patient in need of such treatment. In one embodiment, the composition can be administered to a patient for preventing or treating influenza A virus infection; influenza B virus infection; and combinations thereof. The invention also provides formulations that include an antibody of the invention and a carrier. In one embodiment, the formulation is a therapeutic formulation that includes a pharmaceutically acceptable carrier.

In certain embodiments, the invention provides methods useful for preventing or treating influenza B infection in a mammal, including administering a therapeutically effective amount of the antibody to the mammal. In other embodiments, the invention provides methods useful for preventing or treating influenza A infection; influenza B infection; and combinations thereof in a mammal, including administering a therapeutically effective amount of the antibody to the mammal. The antibody therapeutic compositions can be administered short term (acutely), chronically, or intermittently as directed by physician.

In certain embodiments, the invention also provides articles of manufacture that include at least an antibody of the invention, such as sterile dosage forms and kits. Kits can be provided which contain the antibodies for detection and quantitation of influenza virus in vitro, e.g. in an ELISA or a Western blot. Such antibody useful for detection may be provided with a label such as a fluorescent or radiolabel.

Terminology

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show (2002) 2nd ed. CRC Press; The Dictionary of Cell and Molecular Biology, 3rd ed. (1999) Academic Press; and the Oxford Dictionary Of Biochemistry And Molecular Biology, Revised (2000) Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Anti-Influenza B Virus Antibodies

In certain embodiments, the antibodies are isolated and/or purified and/or pyrogen free antibodies. The term "purified" as used herein, refers to other molecules, e.g., polypeptide, nucleic acid molecule that have been identified and separated and/or recovered from a component of its natural environment. Thus, in one embodiment the antibodies of the invention are purified antibodies wherein they have been separated from one or more components of their natural environment. The term "isolated antibody" as used herein refers to an antibody which is substantially free of other antibody molecules having different antigenic specificities (e.g., an isolated antibody that specifically binds to influenza B virus that is substantially free of antibodies that specifically bind antigens other than those of the influenza B virus HA antibody). Thus, in one embodiment, the antibodies of the invention are isolated antibodies that have been separated from antibodies with a different specificity. Typically, an isolated antibody is a monoclonal antibody. Moreover, an isolated antibody of the invention may be substantially free of one or more other cellular materials and/or chemicals and is herein referred to an isolated and purified antibody. In one embodiment of the invention, a combination of "isolated" monoclonal antibodies relates to antibodies having different specificities and being combined in a well-defined composition. Methods of production and purification/isolation of antibodies are described below in more detail.

The isolated antibodies of the present invention include antibody amino acid sequences disclosed herein encoded by any suitable polynucleotide, or any isolated or formulated antibody.

The antibodies of the invention immunospecifically bind at least one specified epitope specific to the influenza B virus HA protein. The term "epitope" as used herein refers to a protein determinant capable of binding to an antibody. Epitopes usually include chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

In one embodiment, the antibody or antigen binding fragment thereof binds to an epitope present on at least two phylogenetically distinct influenza B lineages. In a more particular embodiment, the antibody or antigen binding fragment thereof binds to an epitope present in at least one influenza B Yamagata strain and at least one influenza B Victoria strain. In one embodiment, the antibody or antigen binding fragment thereof binds to an epitope that is present in influenza B virus of both Yamagata lineage and Victoria lineage. In one embodiment, the antibody or antigen binding fragment thereof binds to an epitope that is conserved among influenza B of both Yamagata lineage and Victoria lineage.

In one embodiment, the antibody or antigen binding fragment thereof binds to at least one influenza B Yamagata strain and at least one influenza B Victoria strain with a half maximal effective concentration ($EC_{50}$) of between about 1 ng/ml and about 500 ng/ml, or between about 1 ng/ml and about 250 ng/ml, or between about 1 ng/ml and about 50 ng/ml, or less than about 500 ng/ml, 250 ng/ml, 100 ng/ml, 50 ng/ml, 40 ng/ml, 30 ng/ml, 20 ng/ml, or 15 µg/ml. In another embodiment, the antibody or antigen binding fragment thereof binds to influenza B virus of Yamagata and Victoria lineage with an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml, 100 ng/ml, 50 ng/ml, 40 ng/ml, 30 ng/ml, 20 ng/ml, or 15 µg/ml. In one embodiment, the antibody or antigen binding fragment thereof binds to an epitope present in influenza B virus of both Yamagata lineage and Victoria lineage with an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml, 100 ng/ml, 50 ng/ml, 40 ng/ml, 30 ng/ml, 20 ng/ml, or 15 µg/ml.

In one embodiment, the antibody or antigen binding fragment thereof binds to: an epitope present on influenza B Yamagata lineage at an $EC_{50}$ of between about 1 ng/ml and about 100 ng/ml, 1 ng/ml and about 50 ng/ml, or between about 1 ng/ml and about 25 ng/ml, or less than about 50 ng/ml or 25 ng/ml; and an epitope present on influenza B Victoria lineage at an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml, 100 ng/ml or 50 ng/ml.

In another embodiment, the antibody or antigen binding fragment thereof binds to: an epitope present on influenza B Yamagata lineage at an $EC_{50}$ of between about 1 ng/ml and about 100 ng/ml, 1 ng/ml and about 50 ng/ml, or between about 1 ng/ml and about 25 ng/ml, or less than about 50 ng/ml or 25 ng/ml; an epitope present on influenza B Victoria lineage at an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml or 100 ng/ml; and an epitope on influenza A HA with an $EC_{50}$ of between about 1 µg/ml and about 50 µg/ml, or less than about 50 µg/ml, 25 µg/ml, 15 µg/ml or 10 µg/ml. In another embodiment, the antibody or antigen binding fragment thereof binds to: an epitope present on influenza B Yamagata lineage at an $EC_{50}$ of between about 1 ng/ml and about 100 ng/ml, 1 ng/ml and about 50 ng/ml, or between about 1 ng/ml and about 25 ng/ml, or less than about 50 ng/ml or 25 ng/ml; an epitope present on influenza B Victoria lineage at an $EC_{50}$ of between about 1 ng/ml and about 500 ng/ml, or between about 1 ng/ml and about 250 ng/ml, or between about 1 ng/ml and about 50 ng/ml, or less than about 500 ng/ml, 250 ng/ml or 100 ng/ml; and an epitope on influenza A H9 HA with an $EC_{50}$ of between about 1 µg/ml and about 50 µg/ml, or less than about 50 µg/ml, 25 µg/ml, 15 µg/ml or 10 µg/ml.

In one embodiment, the antibody or antigen binding fragment thereof recognizes an epitope that is either a linear epitope, or continuous epitope. In another embodiment, the antibody or antigen binding fragment thereof recognizes a non-linear or conformational epitope. In one embodiment, the epitope is located on the hemagglutinin (HA) glycoprotein of influenza B. In a more particular embodiment, the epitope is located on the head region of the HA glycoprotein of influenza B. In one embodiment, the epitope includes one or more amino acids at positions 128, 141, 150 or 235 in the head region of influenza B HA as contact residues, which are numbered according to the H3 numbering system as described in Wang et al. (2008) J. Virol. 82(6):3011-20. In one embodiment, the epitope includes amino acid 128 of the sequence of the head region of influenza B HA as a contact residue. In another embodiment, the epitope includes amino acids 141, 150 and 235 of the sequence of the head region of influenza B HA as contact residues.

The epitope or epitopes recognized by the antibody or antigen binding fragment thereof of the invention may have a number of uses. For example, the epitope in purified or synthetic form can be used to raise immune responses (i.e., as a vaccine, or for the production of antibodies for other uses) or for screening sera for antibodies that immunoreact with the epitope. In one embodiment, an epitope recognized by the antibody or antigen binding fragment thereof of the invention, or an antigen having such an epitope may be used as a vaccine for raising an immune response. In another embodiment, the antibodies and antigen binding fragments of the invention can be used to monitor the quality of vaccines, for example, by determining whether the antigen in a vaccine contains the correct immunogenic epitope in the correct conformation.

Variable Regions

As used herein, the term "parent antibody" refers to an antibody which is encoded by an amino acid sequence used for the preparation of a variant or derivative, defined herein. The parent polypeptide may include a native antibody sequence (i.e., a naturally occurring, including a naturally occurring allelic variant) or an antibody sequence with pre-existing amino acid sequence modifications (such as other insertions, deletions and/or substitutions) of a naturally occurring sequence. The parent antibody may be a humanized antibody or a human antibody. In one embodiment, antibodies of the invention are variants of a parent antibody. As used herein, the term "variant" refers to an antibody that differs in amino acid sequence from a "parent" antibody amino acid sequence by virtue of addition, deletion and/or substitution of one or more amino acid residue(s) in the parent antibody sequence.

The antigen-binding portion of an antibody includes one or more fragments of an antibody that retain the ability to specifically bind to an antigen. It has been shown that the antigen-binding function of an antibody can be performed by fragments of a full-length antibody. Examples of antigen binding fragments encompassed within the term "antigen-binding portion" of an antibody include (i) a Fab fragment, a monovalent fragment that includes the VL, VH, CL and CH1 domains; (ii) a F(ab')2 fragment, a bivalent fragment that includes two Fab fragments linked by a disulfide bridge at the hinge region; (iii) a Fd fragment that includes the VH and CH1 domains; (iv) a Fv fragment that includes the VL and VH domains of a single arm of an antibody, (v) a dAb fragment (Ward et al. (1989) Nature. 341:544-546), which includes a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science. 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies of the invention include at least one antigen binding domain, which include a VH and a VL domain described herein. Exemplary VH and VL domains are shown in Table 1, below.

TABLE 1

VH and VL domains

|  | VH (DNA) SEQ ID NO: | VL (DNA) SEQ ID NO: | VH (AA) SEQ ID NO: | VL (AA) SEQ ID NO: |
|---|---|---|---|---|
| FBD-56 | 1 | 6 | 2 | 7 |
| FBD-94 | 11 | 16 | 12 | 17 |
| FBC-39 | 21 | 26 | 22 | 27 |
| FBC-39 LSL | 31 | 36 | 32 | 37 |
| FBC-39 FSL | 41 | 46 | 42 | 47 |
| FBC-39 LTL | 51 | 56 | 52 | 57 |
| FBC-39 FTL | 61 | 66 | 62 | 67 |
| FBC-39-FSS | 73 | 81 | 74 | 82 |
| FBC-39-LTS | 89 | 97 | 90 | 98 |
| FBC-39-FTS | 105 | 113 | 106 | 114 |

In certain embodiments, the purified antibodies include a VH and/or VL that has a given percent identify to at least one of the VH and/or VL sequences disclosed herein. As used herein, the term "percent (%) sequence identity", also including "homology" is defined as the percentage of amino acid residues or nucleotides in a candidate sequence that are identical with the amino acid residues or nucleotides in the reference sequences, such as parent antibody sequence, after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman (1981) Ads App. Math. 2:482, by means of the local homology algorithm of Neddleman and Wunsch (1970) J. Mol. Biol. 48:443, by means of the similarity search method of Pearson and Lipman (1988) Proc. Natl Acad. Sci. USA 85:2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

Antibodies of the invention may include a VH amino acid sequence having at least 65%, 70%, 75%, 80%, 85%, 90%, 95% or 100% identity to the VH amino acid sequences described herein. In another embodiment, antibodies of the invention may have a VH amino acid sequence having at least, 90%, 91%, 92%, 93%, 94%, 95%, 96%, 97%, 98%, 99% or 100% identity to the amino acid sequence of the VH amino acid sequences described herein.

Antibodies of the invention may include a VL amino acid sequence having at least 65%, 70%, 75%, 80%, 85%, 90%, 95% or 100% identity to the VL amino acid sequences described herein. In another embodiment, antibodies of the invention may have a VL amino acid sequence having at least, 90%, 91%, 92%, 93%, 94%, 95%, 96%, 97%, 98%, 99% or 100% identity to the VL amino acid sequences described herein.

Complementarity Determining Regions (CDRs)

While the variable domain (VH and VL) includes the antigen-binding region; the variability is not evenly distributed through the variable domains of antibodies. It is concentrated in segments called Complementarity Determining Regions (CDRs), both in the light chain (VL or VK) and the heavy chain (VH) variable domains. The more highly conserved portions of the variable domains are called the framework regions (FR). The variable domains of native heavy and light chains each include four FR, largely adopting a β-sheet configuration, connected by three CDRs, which form loops connecting, and in some cases forming part of, the β-sheet structure. The CDRs in each chain are held together in close proximity by the FR and, with the CDRs from the other chain, contribute to the formation of the antigen-binding site of antibodies. The three CDRs of the heavy chain are designated HCDR-1, HCDR-2, and HCDR-3, and the three CDRs of the light chain are designated LCDR-1, LCDR-2, and LCDR-3.

In one embodiment, the amino acids in the variable domain, complementarity determining region (CDRs) and framework regions (FR) of an antibody can be identified following Kabat et al. (1991) Sequences of Proteins of Immunological Interest, 5th Ed. Public Health Service, National Institutes of Health, Bethesda, Md. Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g. residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues often requires the insertion of "spacer" residues in the numbering system. In addition, the identity of certain individual residues at any given Kabat site number may vary from antibody chain to antibody chain due to interspecies or allelic divergence.

According to the Kabat et al. numbering system, HCDR-1 begins at approximately amino acid 31 (i.e., approximately 9 residues after the first cysteine residue), includes approximately 5-7 amino acids, and ends at the next tyrosine residue. HCDR-2 begins at the fifteenth residue after the end of CDR-H1, includes approximately 16-19 amino acids, and ends at the next arginine or lysine residue. HCDR-3 begins at approximately the thirty third amino acid residue after the end of HCDR-2; includes 3-25 amino acids; and ends at the sequence W-G-X-G, where X is any amino acid. LCDR-1 begins at approximately residue 24 (i.e., following a cysteine residue); includes approximately 10-17 residues; and ends at the next tyrosine residue. LCDR-2 begins at approximately the sixteenth residue after the end of LCDR-1 and includes approximately 7 residues. LCDR-3 begins at approximately the thirty third residue after the end of LCDR-2; includes approximately 7-11 residues and ends at the sequence F-G-X-G, where X is any amino acid. Note that CDRs vary considerably from antibody to antibody (and by definition will not exhibit homology with the Kabat consensus sequences). CDR heavy chain and light chain sequences of antibodies of the invention, numbered using the Kabat system are shown in Tables 2 and 3, below.

TABLE 2

HCDR-1-3, as identified by Kabat et al.

|  | HCDR-1 SEQ ID NO: | HCDR-2 SEQ ID NO: | HCDR-3 SEQ ID NO: |
|---|---|---|---|
| FBD-56 | 3 | 4 | 5 |
| FBD-94 | 13 | 14 | 15 |
| FBC-39 | 23 | 24 | 25 |
| FBC-39 LSL | 33 | 34 | 35 |
| FBC-39 FSL | 43 | 44 | 45 |
| FBC-39 LTL | 53 | 54 | 55 |
| FBC-39 FTL | 63 | 64 | 65 |
| FBC-39-FSS | 75 | 76 | 77 |

TABLE 2-continued

HCDR-1-3, as identified by Kabat et al.

|  | HCDR-1 SEQ ID NO: | HCDR-2 SEQ ID NO: | HCDR-3 SEQ ID NO: |
|---|---|---|---|
| FBC-39-LTS | 91 | 92 | 93 |
| FBC-39-FTS | 107 | 108 | 109 |

TABLE 3

LCDR-1-3, as identified by Kabat et al.

|  | LCDR-1 SEQ ID NO: | LCDR-2 SEQ ID NO: | LCDR-3 SEQ ID NO: |
|---|---|---|---|
| FBD-56 | 8 | 9 | 10 |
| FBD-94 | 18 | 19 | 20 |
| FBC-39 | 28 | 29 | 30 |
| FBC-39 LSL | 38 | 39 | 40 |
| FBC-39 FSL | 48 | 49 | 50 |
| FBC-39 LTL | 58 | 59 | 60 |
| FBC-39 FTL | 68 | 69 | 70 |
| FBC-39-FSS | 83 | 84 | 85 |
| FBC-39-LTS | 99 | 100 | 101 |
| FBC-39-FTS | 115 | 116 | 117 |

Although the Kabat numbering scheme is widely used, it has some shortcomings. First, since the numbering scheme was developed from sequence data, in the absence of structural information, the position at which insertions occur in LCDR-1 and HCDR-1 does not always match the structural insertion position. Thus, topologically equivalent residues in these loops may not receive the same number. Second, the numbering system is rigid, allowing only for a limited number of insertions. If there are more residues than the allotted numbering system for insertions, there is no standard way of numbering them.

In another embodiment, the amino acids in the variable domain, complementarity determining regions (CDRs) and framework regions (FR) of an antibody can be identified using the Immunogenetics (IMGT) database (http://imgt.cines.fr). Lefranc et al. (2003) Dev Comp Immunol. 27(1):55-77. The IMGT database was developed using sequence information for immunoglobulins (IgGs), T-cell receptors (TcR) and Major Histocompatibility Complex (MHC) molecules and unifies numbering across antibody lambda and kappa light chains, heavy chains and T-cell receptor chains and avoids the use of insertion codes for all but uncommonly long insertions. IMGT also takes into account and combines the definition of the framework (FR) and complementarity determining regions (CDR) from Kabat et al., the characterization of the hypervariable loops from Chothia et al., as well as structural data from X-ray diffraction studies. CDR heavy chain and light chain sequences for antibodies of the invention, numbered using the IMGT system, are shown in Tables 4 and 5, below. FIGS. 5A and C provide an alignment of the FBD-56 VH (SEQ. ID. NO. 2), FBD-94 VH (SEQ. ID. NO. 12) and FBC-39 VH (SEQ. ID. NO. 22) sequences showing the CDR sequences as identified by Kabat, and IMGT, respectively. FIGS. 5B and D provide an alignment of the FBD-56 VL (SEQ. ID. NO. 7), FBD-94 VL (SEQ. ID. NO. 17) and FBC-39 VL (SEQ. ID. NO. 27) sequences showing the CDR sequences as identified by Kabat and IMGT, respectively.

TABLE 4

HCDR-1-3, as identified by IMGT

|  | HCDR-1 SEQ ID NO: | HCDR-2 SEQ ID NO: | HCDR-3 SEQ ID NO: |
|---|---|---|---|
| FBC-39 | 121 | 122 | 123 |
| FBC-39 LSL | 127 | 128 | 129 |
| FBC-39 FSL | 133 | 134 | 135 |
| FBC-39 LTL | 139 | 140 | 141 |
| FBC-39 FTL | 145 | 146 | 147 |
| FBC-39-FSS | 78 | 79 | 80 |
| FBC-39-LTS | 94 | 95 | 96 |
| FBC-39-FTS | 110 | 111 | 112 |

TABLE 5

LCDR-1-3, as identified by IMGT

|  | LCDR-1 SEQ ID NO: | LCDR-2 SEQ ID NO: | LCDR-3 SEQ ID NO: |
|---|---|---|---|
| FBC-39 | 124 | 125 | 126 |
| FBC-39 LSL | 130 | 131 | 132 |
| FBC-39 FSL | 136 | 137 | 138 |
| FBC-39 LTL | 142 | 143 | 144 |
| FBC-39 FTL | 148 | 149 | 150 |
| FBC-39-FSS | 86 | 87 | 88 |
| FBC-39-LTS | 102 | 103 | 104 |
| FBC-39-FTS | 118 | 119 | 120 |

The present invention encompasses neutralizing anti-influenza B antibodies that include amino acids in a sequence that is at least 75%, 80%, 85%, 90%, 95% or 100% identical to an amino acid sequence of a VH of SEQ ID NO.: 2; SEQ ID NO.: 12; SEQ ID NO.: 22; SEQ ID NO.: 32; SEQ ID NO.: 42; SEQ ID NO.: 52; SEQ ID NO.: 62; SEQ ID NO.: 74; SEQ ID NO.: 90; or SEQ ID NO.: 106; and/or at least 75%, 80%, 85%, 90%, 95% or 100% identical to an amino acid sequence of a VL of SEQ ID NO.: 7; SEQ ID NO.: 17; SEQ ID NO.: 27; SEQ ID NO.: 37; SEQ ID NO.: 47; SEQ ID NO.: 57; SEQ ID NO.: 67; SEQ ID NO.: 82; SEQ ID NO.: 98; or SEQ ID NO.: 114. In another embodiment, the present invention encompasses neutralizing anti-influenza B antibodies that include amino acids in a sequence that is at least 95%, 96%, 97%, 98%, 99% or 100% identical to an amino acid sequence of a VH of SEQ ID NO.: 2; SEQ ID NO.: 12; SEQ ID NO.: 22; SEQ ID NO.: 32; SEQ ID NO.: 42; SEQ ID NO.: 52; SEQ ID NO.: 62; SEQ ID NO.: 74; SEQ ID NO.: 90; or SEQ ID NO.: 106; and/or at least 95%, 96%, 97%, 98%, 99% or 100% identical to an amino acid sequence of a VL of SEQ ID NO.: 7; SEQ ID NO.: 17; SEQ ID NO.: 27; SEQ ID NO.: 37; SEQ ID NO.: 47; SEQ ID NO.: 57; SEQ ID NO.: 67; SEQ ID NO.: 82; SEQ ID NO.: 98; or SEQ ID NO.: 114.

In another embodiment, invention provides antibodies and antigen binding fragments thereof that include a set of six CDRs: HCDR-1, HCDR-2, HCDR-3, LCDR-1, LCDR-2, LCDR-3, wherein CDRs are selected from the HCDRs and LCDRs shown in Tables 2 through 5. In another embodiment, the invention provides antibodies and antigen binding fragments thereof that include a set of six CDRs: HCDR-1, HCDR-2, HCDR-3, LCDR-1, LCDR-2, LCDR-3, wherein CDRs include amino acids in a sequence that is at least 75%, 80%, 85%, 90%, 95% or 100% identical to an amino acid sequence of the HCDRs and LCDRs shown in Tables 2 through 5. In another embodiment, the invention provides antibodies and antigen binding fragments thereof that include a set of six CDRs: HCDR-1, HCDR-2, HCDR- 3, LCDR-1, LCDR-2, LCDR-3, wherein CDRs include amino acids in a sequence that is at least 95%, 96%, 97%, 98%, 99% or 100% identical to an amino acid sequence of the HCDRs and LCDRs shown in Tables 2 through 5.

Framework Regions

The variable domains of the heavy and light chains each include four framework regions (FR1, FR2, FR3, FR4), which are the more highly conserved portions of the variable domains. The four FRs of the heavy chain are designated FR-H1, FR-H2, FR-H3 and FR-H4, and the four FRs of the light chain are designated FR-L1, FR-L2, FR-L3 and FR-L4.

In one embodiment, the Kabat numbering system can be used to identify the framework regions. According to Kabat et al., FR-H1 begins at position 1 and ends at approximately amino acid 30, FR-H2 is approximately from amino acid 36 to 49, FR-H3 is approximately from amino acid 66 to 94 and FR-H4 is approximately amino acid 103 to 113. FR-L1 begins at amino acid 1 and ends at approximately amino acid 23, FR-L2 is approximately from amino acid 35 to 49, FR-L3 is approximately from amino acid 57 to 88 and FR-L4 is approximately from amino acid 98 to 107. In certain embodiments the framework regions may contain substitutions according to the Kabat numbering system, e.g., insertion at 106A in FR-L1. In addition to naturally occurring substitutions, one or more alterations (e.g., substitutions) of FR residues may also be introduced in an antibody of the invention, provided it retains neutralizing ability. In certain embodiments, these result in an improvement or optimization in the binding affinity of the antibody for influenza B virus HA. Examples of framework region residues to modify include those which non-covalently bind antigen directly (Amit et al. (1986) Science. 233:747-753); interact with/effect the conformation of a CDR (Chothia et al. (1987) J. Mol. Biol. 196:901-917); and/or participate in the VL-VH interface (U.S. Pat. No. 5,225,539). In other embodiments, the framework regions can be identified using the numbering system of IMGT.

In another embodiment the FR may include one or more amino acid changes for the purposes of "germlining". For example, the amino acid sequences of selected antibody heavy and light chains can be compared to germline heavy and light chain amino acid sequences; where certain framework residues of the selected VL and/or VH chains differ from the germline configuration (e.g., as a result of somatic mutation of the immunoglobulin), it may be desirable to "back-mutate" the altered framework residues of the selected antibodies to the germline configuration (i.e., change the framework amino acid sequences of the selected antibodies so that they are the same as the germline framework amino acid sequences), for example, to reduce the chance of immunogenicity. Such "back-mutation" (or "germlining") of framework residues can be accomplished by standard molecular biology methods for introducing specific mutations (e.g., site-directed mutagenesis; PCR-mediated mutagenesis, and the like).

FIG. 6 shows the amino acid sequence of the VH domain of a genericized anti-influenza B antibody (SEQ ID NO:71) in which non-germline residues in FBC-39 (SEQ ID NO: 22) are designated as $Xaa_{1-11}$. In one embodiment, one or more of the non-germline ($Xaa_{1-11}$) residues are "back-mutated" to germline. In one embodiment, $Xaa_1$ of SEQ ID NO: 71 is Val or Glu; $Xaa_2$ of SEQ ID NO: 71 is Leu or Phe; $Xaa_3$ of SEQ ID NO: 71 is Ser or Thr; $Xaa_4$ of SEQ ID NO: 71 is Leu or Ser; $Xaa_5$ of SEQ ID NO: 71 is Ser or Thr; $Xaa_6$ of SEQ ID NO: 71 is Met or Thr; $Xaa_7$ of SEQ ID NO: 71 is Phe or Tyr; $Xaa_8$ of SEQ ID NO: 71 is His or Gln; $Xaa_9$ of SEQ ID NO: 71 is Ser or Asn; $Xaa_{10}$ of SEQ ID NO: 71 is Arg or Lys; and $Xaa_{11}$ of SEQ ID NO: 71 is Ala or Thr. In another embodiment, $Xaa_1$ of SEQ ID NO:71 is Glu, $Xaa_5$ of SEQ ID NO:71 is Thr; $Xaa_6$ of SEQ ID NO:71 is Thr; $Xaa_7$ of SEQ ID NO:71 is Tyr; $Xaa_8$ of SEQ ID NO:71 is Thr; $Xaa_{10}$ of SEQ ID NO:71 is Lys; $Xaa_{11}$ of SEQ ID NO:71 is Thr, or combinations thereof. In a more particular embodiment, $Xaa_9$ of SEQ ID NO:71 is Ser. In yet another embodiment, $Xaa_4$ of SEQ ID NO:71 is Leu.

FIG. 7 shows an amino acid sequence of the VL domain of a genericized anti-influenza B antibody (SEQ ID NO:72), in which non-germline residues in FBC-39 (SEQ ID NO: 27) are represented by $Xaa_1$. In one embodiment, the non-germline residue ($Xaa_1$) is "back-mutated" to germline. In one embodiment, $Xaa_1$ of SEQ ID NO:72 is Phe or Tyr. In a more particular embodiment, $Xaa_1$ of SEQ ID NO:72 is Tyr.

Nucleotide Sequences Encoding Antibodies of the Invention

In addition to the amino acid sequences described above, the invention further provides nucleotide sequences corresponding to the amino acid sequences and encoding the human antibodies of the invention. In one embodiment, the invention provides polynucleotides that include a nucleotide sequence encoding an antibody described herein or fragments thereof. These include, but are not limited to, nucleotide sequences that code for the above referenced amino acid sequences. Thus, the present invention also provides polynucleotide sequences encoding VH and VL framework regions including CDRs and FRs of antibodies described herein as well as expression vectors for their efficient expression in cells (e.g. mammalian cells). Methods of making the antibodies using polynucleotides are described below in more detail.

The invention also encompasses polynucleotides that hybridize under stringent or lower stringency hybridization conditions, e.g., as defined herein, to polynucleotides that encode an antibody of the invention described herein. The term "stringency" as used herein refers to experimental conditions (e.g. temperature and salt concentration) of a hybridization experiment to denote the degree of homology between the probe and the filter bound nucleic acid; the higher the stringency, the higher percent homology between the probe and filter bound nucleic acid.

Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 65° C., or any other stringent hybridization conditions known to those skilled in the art (see, for example, Ausubel et al., eds. (1989) Current Protocols in Molecular Biology, vol. 1, Green Publishing Associates, Inc. and John Wiley and Sons, Inc., NY at pages 6.3.1 to 6.3.6 and 2.10.3).

Substantially identical sequences may be polymorphic sequences, i.e., alternative sequences or alleles in a population. An allelic difference may be as small as one base pair. Substantially identical sequences may also include mutagenized sequences, including sequences having silent mutations. A mutation may include one or more residue changes, a deletion of one or more residues, or an insertion of one or more additional residues.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al. (1994) BioTechniques. 17:242), which, briefly, involves the synthesis of overlapping oligonucleotides containing portions of the sequence encoding the antibody, annealing and ligating of those oligonucleotides, and then amplification of the ligated oligonucleotides by PCR.

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, in one embodiment polyA+RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual, 2d Ed., Cold Spring Harbor Laboratory, Cold Spring Harbor, N.Y. and Ausubel et al. eds. (1998) Current Protocols in Molecular Biology, John Wiley & Sons, NY), to generate antibodies having a different amino acid sequence, for example to create amino acid substitutions, deletions, and/or insertions.

Binding Characteristics

As described above, the antibodies or antigen binding fragments of the invention immunospecifically bind at least one specified epitope or antigenic determinant of influenza B virus HA protein, peptide, subunit, fragment, portion or any combination thereof either exclusively or preferentially with respect to other polypeptides. In a specific embodiment, the epitope or antigenic determinant of influenza B virus HA protein is the globular head. The term "epitope" or "antigenic determinant" as used herein refers to a protein determinant capable of binding to an antibody. In one embodiment, the term "binding" herein relates to specific binding. These protein determinants or epitopes usually include chemically active surface groupings of molecules such as amino acids or sugar side chains and usually have a specific three dimensional structural characteristics, as well as specific charge characteristics. Conformational and non-conformational epitopes are distinguished in that the binding to the former but not the latter is lost in the presence of denaturing solvents. The term "discontinuous epitope" as used herein, refers to a conformational epitope on a protein antigen which is formed from at least two separate regions in the primary sequence of the protein.

The interactions between antigens and antibodies are the same as for other non-covalent protein-protein interactions. In general, four types of binding interactions exist between antigens and antibodies: (i) hydrogen bonds, (ii) dispersion forces, (iii) electrostatic forces between Lewis acids and Lewis bases, and (iv) hydrophobic interactions. Hydrophobic interactions are a major driving force for the antibody-antigen interaction, and are based on repulsion of water by non-polar groups rather than attraction of molecules (Tanford, (1978) Science. 200:1012-8). However, certain physical forces also contribute to antigen-antibody binding, for example, the fit or complimentary of epitope shapes with different antibody binding sites. Moreover, other materials and antigens may cross-react with an antibody, thereby competing for available free antibody.

Measurement of the affinity constant and specificity of binding between antigen and antibody can assist in determining the efficacy of prophylactic, therapeutic, diagnostic and research methods using the antibodies of the invention. "Binding affinity" generally refers to the strength of the sum total of the noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the equilibrium dissociation constant (Kd), which is calculated as the ratio $k_{off}/k_{on}$. See, e.g., Chen et al. (1999) J. Mol Biol. 293:865-881. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

One method for determining binding affinity includes measuring the disassociation constant "Kd" by a radiolabeled antigen binding assay (RIA) performed with the Fab version of an antibody of interest and its antigen as described by Chen et al. (1999) J. Mol Biol. 293:865-881. Alternately, the Kd value may be measured by using surface plasmon resonance assays using a BIAcore™-2000 or a BIAcore™-3000 (BIAcore, Inc., Piscataway, N.J.). If the on-rate exceeds $10^6$ $M^{-1}$ $S^{-1}$ by the surface plasmon resonance assay, then the on-rate can be determined by using a fluorescent quenching technique that measures the increase or decrease in fluorescence emission intensity in the presence of increasing concentrations of antigen. An "on-rate" or "rate of association" or "association rate" or "$k_{on}$" can also be determined with the same surface plasmon resonance technique described above.

Methods and reagents suitable for determination of binding characteristics of an antibody of the present invention, or an altered/mutant derivative thereof, are known in the art and/or are commercially available (U.S. Pat. Nos. 6,849,425; 6,632,926; 6,294,391; 6,143,574). Moreover, equipment and software designed for such kinetic analyses are commercially available (e.g. Biacore® A100, and Biacore® 2000 instruments; Biacore International AB, Uppsala, Sweden).

In one embodiment, antibodies of the present invention, including antigen binding fragments or variants thereof, may also be described or specified in terms of their binding affinity for influenza A virus polypeptides; influenza B virus polypeptides; or a combination thereof. Typically, antibodies with high affinity have Kd of less than $10^{-7}$ M. In one embodiment, antibodies or antigen binding fragments thereof bind influenza A polypeptides; influenza B polypeptides; fragments or variants thereof; or a combination thereof, with a dissociation constant or Kd of less than or equal to $5\times10^{-7}$ M, $10^{-7}$ M, $5\times10^{-8}$ M, $10^{-6}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$M, $10^{-13}$M, $5\times10^{-14}$ M, $10^{-14}$ M, $5 \times 10^{-15}$ M or $10^{-15}$ M. In a more particular embodiment, antibodies or antigen binding fragments thereof bind influenza A polypeptides; influenza B polypeptides, fragments or variants thereof; or combinations thereof, with a dissociation constant or Kd of less than or equal to $5 \times 10^{-10}$ M, $10^{-10}$ M, $5 \times 10^{-11}$ M, $10^{-11}$ M, $5 \times 10^{-12}$ M or $10^{-12}$ M. The invention encompasses antibodies that bind influenza A polypeptides; influenza B polypeptides; or a combination thereof, with a dissociation constant or Kd that is within a range between any of the individual recited values.

In another embodiment, antibodies or antigen binding fragments thereof of the invention bind influenza A polypeptides; influenza B polypeptides; fragments or variants thereof; or combinations thereof, with an off rate ($k_{off}$) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$, $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$. In a more particular embodiment, antibodies or antigen binding fragments thereof of the invention bind influenza A polypeptides or fragments or variants thereof with an off rate ($k_{off}$) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$. The invention also encompasses antibodies that bind influenza A polypeptides; influenza B polypeptides; or combinations thereof, with an off rate ($k_{off}$) that is within a range between any of the individual recited values.

In another embodiment, antibodies or antigen binding fragments thereof of the invention bind influenza A polypeptides; influenza B polypeptides; fragments or variants thereof; or combinations thereof, with an on rate ($k_{on}$) of greater than or equal to $10^3$ M$^{-1}$ sec$^{-1}$, $5 \times 10^3$ M$^{-1}$ sec$^{-1}$, $10^4$ M$^{-1}$ sec$^{-1}$, $5 \times 10^4$ M$^{-1}$ sec$^{-1}$, $10^5$ M$^{-1}$ sec$^{-1}$, $5 \times 10^5$ M$^{-1}$ sec$^{-1}$, $10^6$ M$^{-1}$ sec-1, $5 \times 10^6$ M$^{-1}$ sec$^{-1}$, $10^7$ M$^{-1}$ sec-1, or $5 \times 10^7$ M$^{-1}$ sec$^{-1}$. In a more particular embodiment, antibodies or antigen binding fragments thereof of the invention bind influenza A polypeptides; influenza B polypeptides; fragments or variants thereof; or combinations thereof, with an on rate ($k_{on}$) greater than or equal to $10^5$ M$^{-1}$ sec$^{-1}$, $5 \times 10^5$ M$^{-1}$ sec$^{-1}$, $10^6$ M$^{-1}$ sec-1, $5 \times 10^6$ M$^{-1}$ sec$^{-1}$, $10^7$ M$^{-1}$ sec$^{-1}$ or $5 \times 10^7$ M$^{-1}$ sec$^{-1}$. The invention encompasses antibodies that bind influenza A polypeptides; influenza B polypeptides; or combinations thereof, with on rate ($k_{on}$) that is within a range between any of the individual recited values.

In one embodiment, a binding assay may be performed either as a direct binding assay or as a competition-binding assay. Binding can be detected using standard ELISA or standard Flow Cytometry assays. In a direct binding assay, a candidate antibody is tested for binding to its cognate antigen. Competition-binding assay, on the other hand, assess the ability of a candidate antibody to compete with a known antibody or other compound that binds to a particular antigen, for example, influenza B virus HA. In general any method that permits the binding of an antibody with the influenza B virus HA that can be detected is encompassed with the scope of the present invention for detecting and measuring the binding characteristics of the antibodies. One of skill in the art will recognize these well-known methods and for this reason are not provided in detail here. These methods are also utilized to screen a panel of antibodies for those providing the desired characteristics.

In one embodiment, an antibody of the invention immunospecifically binds to influenza B virus HA and is capable of neutralizing influenza B virus infection. In one embodiment, an antibody of the invention immunospecifically binds to at least one Yamagata lineage influenza B virus and at least one Victoria lineage influenza B virus. In another embodiment, an antibody of the invention immunospecifically binds Yamagata lineage and Victoria lineage influenza B virus.

In another embodiment, an antibody of the invention immunospecifically binds to influenza B virus HA and influenza A virus HA and is capable of neutralizing influenza B virus and influenza A virus infection. In one embodiment, an antibody of the invention immunospecifically binds to at least one Yamagata lineage influenza B virus; at least one Victoria lineage influenza B virus and at least one influenza A virus subtype.

The hemagglutinin subtypes of influenza A viruses fall into two major phylogenetic groupings, identified as group 1, which includes subtypes H1, H2, H5, H6, H8, H9, H11, H12, H13, H16 and H17 and group 2, which includes subtypes H3, H4, H7, H10, H14, and H15. In one embodiment, an antibody or antigen binding fragment according to the invention is capable of binding to and/or neutralizing one or more influenza A virus group 1 subtypes selected from H8, H9, H11, H12, H13, H16 and H17 and variants thereof. In another embodiment, an antibody or antigen binding fragment according to the invention is capable of binding to and/or neutralizing one or more influenza A virus group 2 subtypes selected from H4, H10, H14 and H15 and variants thereof. In one embodiment, the antibody of the invention binds to influenza A virus group 1 subtype H9. In one embodiment, the antibody of the invention binds to and neutralizes influenza A virus group 1 subtype H9.

In one embodiment, the antibody of the invention immunospecifically binds to influenza B virus HA and is capable of neutralizing influenza B virus infection. In another embodiment, the antibody of the invention immunospecifically binds to influenza A and influenza B virus HA and is capable of neutralizing influenza A and influenza B virus infection. Neutralization assays can be performed as described herein in the Examples section or using other methods known in the art. The term "inhibitory concentration 50%" (abbreviated as "IC$_{50}$") represents the concentration of an inhibitor (e.g., an antibody of the invention) that is required for 50% neutralization of influenza A and/or influenza B virus. It will be understood by one of ordinary skill in the art that a lower IC$_{50}$ value corresponds to a more potent inhibitor.

In one embodiment, an antibody or antigen binding fragment thereof according to the invention has an IC$_{50}$ for neutralizing influenza B virus in the range of from about 0.001 μg/ml to about 5 μg/ml, or in the range of from about 0.001 μg/ml to about 1 μg/ml of antibody, or less than 5 μg/ml, less than 2 μg/ml, less than 1 μg/ml, less than 0.5 μg/ml, less than 0.1 μg/ml, less than 0.05 μg/ml or less than 0.01 μg/ml in a microneutralization assay.

In one embodiment, an antibody or antigen binding fragment thereof according to the invention has an IC$_{50}$ for neutralizing influenza B virus in the range of from about 0.001 μg/ml to about 5 μg/ml, or in the range of from about 0.001 μg/ml to about 1 μg/ml of antibody, or less than 5 μg/ml, less than 2 μg/ml, less than 1 μg/ml, less than 0.5 μg/ml, less than 0.1 μg/ml, less than 0.05 μg/ml or less than 0.01 μg/ml in a microneutralization assay; and an IC$_{50}$ for neutralizing influenza A virus in the range of from about 0.1 μg/ml to about 5 μg/ml, or in the range of from about 0.1 μg/ml to about 2 μg/ml of antibody, or less than 5 μg/ml, less than 2 μg/ml, less than 1 μg/ml, or less than 0.5 μg/ml for neutralization of influenza A virus in a microneutralization assay.

In one embodiment, an antibody or antigen binding fragment thereof according to the invention has an IC$_{50}$ for neutralizing influenza B virus in the range of from about 0.001 µg/ml to about 50 µg/ml, or in the range of from about 0.001 µg/ml to about 5 µg/ml of antibody, or in the range of from about 0.001 µg/ml to about 1 µg/ml of antibody, or less than 10 µg/ml, less than 5 µg/ml, less than 1 µg/ml, less than 0.5 µg/ml, less than 0.1 µg/ml, less than 0.05 µg/ml or less than 0.01 µg/ml in a microneutralization assay; and an $IC_{50}$ for neutralizing influenza A virus in the range of from about 0.01 µg/ml to about 50 µg/ml, or in the range of from about 0.05 µg/ml to about 5 µg/ml of antibody, or in the range of from about 0.1 µg/ml to about 2 µg/ml of antibody, or less than 50 µg/ml, less than 25 µg/ml, less than 10 µg/ml, less than 5 µg/ml, or less than 2 µg/ml for neutralization of influenza A virus in a microneutralization assay.

In certain embodiments, the antibodies of the invention may induce cell death. An antibody which "induces cell death" is one which causes a viable cell to become nonviable. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue (see, Moore et al. (1995) Cytotechnology 17:1-11), 7AAD or other methods well known in the art can be assessed relative to untreated cells.

In a specific embodiment, the antibodies of the invention may induce cell death via apoptosis. An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. In one embodiment, the antibody which induces apoptosis is one which results in about 2 to 50 fold, in one embodiment about 5 to 50 fold, and in one embodiment about 10 to 50 fold, induction of annexin binding relative to untreated cell in an annexin binding assay.

In another specific embodiment, the antibodies of the invention may induce cell death via antibody-dependent cellular cytotoxicity (ADCC) and/or complement-dependent cell-mediated cytotoxicity (CDC) and/or antibody dependent cell-mediated phagocytosis (ADCP). Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (Greenwood et al. (1993) Eur. J. Immunol. 23(5):1098-104; Morgan et al. (1995) Immunology. 86(2):319-324; Clark, M. (1997) Chemical Immunology. 65:88-110) and that a sugar chain in the Cγ2 domain (Clark, M. (1997) Chemical Immunology. 65:88-110) is also important.

To assess ADCC activity of an antibody of interest, an in vitro ADCC assay can be used, such as that described in U.S. Pat. No. 5,500,362. The assay may also be performed using a commercially available kit, e.g. CytoTox 96® (Promega). Useful effector cells for such assays include, but are not limited to peripheral blood mononuclear cells (PBMC), Natural Killer (NK) cells, and NK cell lines. NK cell lines expressing a transgenic Fc receptor (e.g. CD16) and associated signaling polypeptide (e.g. $FC_{\varepsilon}RI$-γ) may also serve as effector cells (WO 2006/023148). In one embodiment, the NK cell line includes CD16 and has luciferase under the NFAT promoter and can be used to measure NK cell activation, rather than cell lysis or cell death. A similar technology is sold by Promega, which uses Jurkat cells instead of NK cells (Promega ADCC reporter bioassay #G7010). For example, the ability of any particular antibody to mediate lysis by complement activation and/or ADCC can be assayed. The cells of interest are grown and labeled in vitro; the antibody is added to the cell culture in combination with immune cells which may be activated by the antigen antibody complexes; i.e., effector cells involved in the ADCC response. The antibody can also be tested for complement activation. In either case, cytolysis is detected by the release of label from the lysed cells. The extent of cell lysis may also be determined by detecting the release of cytoplasmic proteins (e.g. LDH) into the supernatant. In fact, antibodies can be screened using the patient's own serum as a source of complement and/or immune cells. Antibodies that are capable of mediating human ADCC in the in vitro test can then be used therapeutically in that particular patient. ADCC activity of the molecule of interest may also be assessed in vivo, e.g., in an animal model such as that disclosed in Clynes et al. (1998) Proc. Natl. Acad. Sci. USA 95:652-656. Moreover, techniques for modulating (i.e., increasing or decreasing) the level of ADCC, and optionally CDC activity, of an antibody are well-known in the art (e.g., U.S. Pat. Nos. 5,624,821; 6,194,551; 7,317, 091). Antibodies of the present invention may be capable or may have been modified to have the ability of inducing ADCC and/or CDC. Assays to determine ADCC function can be practiced using human effector cells to assess human ADCC function. Such assays may also include those intended to screen for antibodies that induce, mediate, enhance, block cell death by necrotic and/or apoptotic mechanisms. Such methods including assays utilizing viable dyes, methods of detecting and analyzing caspases, and assays measuring DNA breaks can be used to assess the apoptotic activity of cells cultured in vitro with an antibody of interest.

Production of Antibodies

The following describes exemplary techniques for the production of the antibodies useful in the present invention.

Monoclonal Antibodies

Monoclonal antibodies can be prepared using a wide variety of techniques known in the art including the use of hybridoma (Kohler et al. (1975) Nature. 256:495; Harlow et al. (1988) Antibodies: A Laboratory Manual, (Cold Spring Harbor Laboratory Press, 2nd ed.); Hammerling et al. (1981) in: Monoclonal Antibodies and T-Cell Hybridomas 563-681 (Elsevier, N.Y.), recombinant, and phage display technologies, or a combination thereof. The term "monoclonal antibody" as used herein refers to an antibody obtained from a population of substantially homogeneous or isolated antibodies, e.g., the individual antibodies that make up the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against the same determinant on the antigen. In addition to their specificity, monoclonal antibodies are advantageous in that they may be synthesized uncontaminated by other antibodies. The modifier "monoclonal" is not to be construed as requiring production of the antibody by any particular method. Following is a description of representative methods for producing monoclonal antibodies which is not intended to be limiting and may be used to produce, for example, monoclonal mammalian, chimeric, humanized, human, domain, diabodies, vaccibodies, linear and multispecific antibodies.

Hybridoma Techniques

Methods for producing and screening for specific antibodies using hybridoma technology are routine and well known in the art. In the hybridoma method, mice or other appropriate host animals, such as hamster, are immunized as described above to elicit lymphocytes that produce or are capable of producing antibodies that will specifically bind to the antigen used for immunization. Alternatively, lymphocytes may be immunized in vitro. After immunization, lymphocytes are isolated and then fused with a myeloma cell line using a suitable fusing agent or fusion partner, such as polyethylene glycol, to form a hybridoma cell (Goding (1986) Monoclonal Antibodies: Principles and Practice, pp. 59-103 (Academic Press)). In certain embodiments, the selected myeloma cells are those that fuse efficiently, support stable high-level production of antibody by the selected antibody-producing cells, and are sensitive to a selective medium that selects against the unfused parental cells. In one aspect, the myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor (1984) J. Immunol. 133:3001; and Brodeur et al. (1987) Monoclonal Antibody Production Techniques and Applications, pp. 51-63 (Marcel Dekker, Inc., New York). Once hybridoma cells that produce antibodies of the desired specificity, affinity, and/or activity are identified, the clones may be subcloned by limiting dilution procedures and grown by standard methods (Goding, Supra). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the sub-clones are suitably separated from the culture medium, ascites fluid, or serum by conventional antibody purification procedures such as, for example, affinity chromatography (e.g., using protein A or protein G-Sepharose) or ion-exchange chromatography, affinity tags, hydroxylapatite chromatography, gel electrophoresis, dialysis, etc. Exemplary purification methods are described in more detail below.

Recombinant DNA Techniques

Methods for producing and screening for specific antibodies using recombinant DNA technology are routine and well known in the art (e.g. U.S. Pat. No. 4,816,567). DNA encoding the monoclonal antibodies may be readily isolated and/or sequenced using conventional procedures (e.g., by using oligonucleotide probes that are capable of binding specifically to genes encoding the heavy and light chains of murine antibodies). Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al. (1993) Curr. Opinion in Immunol. 5:256-262 and Pluckthun (1992) Immunol. Revs. 130:151-188. As described below, for antibodies generated by phage display and humanization of antibodies, DNA or genetic material for recombinant antibodies can be obtained from source(s) other than hybridomas to generate antibodies of the invention.

Recombinant expression of an antibody or variant thereof generally requires construction of an expression vector containing a polynucleotide that encodes the antibody. The invention, thus, provides replicable vectors that include a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. Human cell lines developed by immortalizing human lymphocytes can be used to recombinantly produce monoclonal antibodies. The human cell line PER.C6®. (Crucell, Netherlands) can be used to recombinantly produce monoclonal antibodies.

Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681, etc.), plants cells (US20080066200), and chicken cells (WO2008142124).

In certain embodiments, antibodies of the invention are expressed in a cell line with stable expression of the antibody. Stable expression can be used for long-term, high-yield production of recombinant proteins. For example, cell lines which stably express the antibody molecule may be generated. Host cells can be transformed with an appropriately engineered vector that include expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Methods for producing stable cell lines with a high yield are well known in the art and reagents are generally available commercially.

In certain embodiments, antibodies of the invention are expressed in a cell line with transient expression of the antibody. Transient transfection is a process in which the nucleic acid introduced into a cell does not integrate into the genome or chromosomal DNA of that cell. It is in fact maintained as an extra-chromosomal element, e.g. as an episome, in the cell. Transcription processes of the nucleic acid of the episome are not affected and a protein encoded by the nucleic acid of the episome is produced.

The cell line, either stable or transiently transfected, is maintained in cell culture medium and conditions well known in the art resulting in the expression and production of monoclonal antibodies. In certain embodiments, the mammalian cell culture media is based on commercially available media formulations, including, for example, DMEM or Ham's F12. In other embodiments, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

In one embodiment, the cell lines are maintained using a fed batch method. As used herein, "fed batch method," refers to a method by which a cell culture is supplied with additional nutrients after first being incubated with a basal medium. For example, a fed batch method may include adding supplemental media according to a determined feeding schedule within a given time period. Thus, a "fed batch cell culture" refers to a cell culture wherein the cells, typically mammalian, and culture medium are supplied to the culturing vessel initially and additional culture nutrients are fed, continuously or in discrete increments, to the culture during culturing, with or without periodic cell and/or product harvest before termination of culture.

The cell culture medium used and the nutrients contained therein are known to one of skill in the art. In one embodiment, the cell culture medium includes a basal medium and at least one hydrolysate, e.g., soy-based hydrolysate, a yeast-based hydrolysate, or a combination of the two types of hydrolysates resulting in a modified basal medium. In another embodiment, the additional nutrients may include only a basal medium, such as a concentrated basal medium, or may include only hydrolysates, or concentrated hydrolysates. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used in the invention include BME Basal Medium (Gibco-Invitrogen, see also Eagle, H (1965) Proc. Soc. Exp. Biol. Med. 89, 36); Dulbecco's Modified Eagle Medium (DMEM, powder) (Gibco-Invitrogen (#31600); see also Dulbecco and Freeman (1959) Virology. 8:396; Smith et al. (1960) Virology. 12:185. Tissue Culture Standards Committee, In Vitro 6:2, 93); CMRL 1066 Medium (Gibco-Invitrogen (#11530); see also Parker et al. (1957) Special Publications, N.Y. Academy of Sciences, 5:303).

The basal medium may be serum-free, meaning that the medium contains no serum (e.g., fetal bovine serum (FBS), horse serum, goat serum, or any other animal-derived serum known to one skilled in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. In certain embodiments, the cell culture medium contains a modified basal cell medium, and at least one of the following nutrients, an iron source, a recombinant growth factor; a buffer; a surfactant; an osmolarity regulator; an energy source; and non-animal hydrolysates. In addition, the modified basal cell medium may optionally contain amino acids, vitamins, or a combination of both amino acids and vitamins. In another embodiment, the modified basal medium further contains glutamine, e.g, L-glutamine, and/or methotrexate.

Antibody production can be conducted in large quantity by a bioreactor process using fed-batch, batch, perfusion or continuous feed bioreactor methods known in the art. Large-scale bioreactors have at least 1000 liters of capacity, in one embodiment about 1,000 to 100,000 liters of capacity. These bioreactors may use agitator impellers to distribute oxygen and nutrients. Small scale bioreactors refers generally to cell culturing in no more than approximately 100 liters in volumetric capacity, and can range from about 1 liter to about 100 liters. Alternatively, single-use bioreactors (SUB) may be used for either large-scale or small-scale culturing.

Temperature, pH, agitation, aeration and inoculum density will vary depending upon the host cells used and the recombinant protein to be expressed. For example, a recombinant protein cell culture may be maintained at a temperature between 30° C. and 45° C. The pH of the culture medium may be monitored during the culture process such that the pH stays at an optimum level, which may be for certain host cells, within a pH range of 6.0 to 8.0. An impeller driven mixing may be used for such culture methods for agitation. The rotational speed of the impeller may be approximately 50 to 200 cm/sec tip speed, but other airlift or other mixing/aeration systems known in the art may be used, depending on the type of host cell being cultured. Sufficient aeration is provided to maintain a dissolved oxygen concentration of approximately 20% to 80% air saturation in the culture, again, depending upon the selected host cell being cultured. Alternatively, a bioreactor may sparge air or oxygen directly into the culture medium. Other methods of oxygen supply exist, including bubble-free aeration systems employing hollow fiber membrane aerators.

Phage Display Techniques

Monoclonal antibodies or antibody fragments can be isolated from antibody phage libraries generated using the techniques described in McCafferty et al. (1990) Nature. 348:552-554; Clackson et al. (1991) Nature. 352:624-628 and Marks et al. (1991) J. Mol. Biol. 222:581-597. In such methods antibodies can be isolated by screening a recombinant combinatorial antibody library. In one embodiment a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612), examples of methods and reagents particularly amenable for use in generating and screening antibody display libraries can be found in, for example, U.S. Pat. Nos. 6,248,516; 6,545,142; 6,291,158; 6,291,159; 6,291,160; 6,291,161; 6,680,192; 5,969,108; 6,172,197; 6,806,079; 5,885,793; 6,521,404; 6,544,731; 6,555,313; 6,593,081; 6,582,915; 7,195,866. Thus, these techniques are viable alternatives to traditional monoclonal antibody hybridoma techniques for generation and isolation of monoclonal antibodies.

In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein.

As described in the above references, after phage selection, the antibody coding regions from the phage can be isolated and used to generate whole antibodies, including human antibodies, humanized antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al. (1992) BioTechniques. 12(6): 864-869; and Better et al. (1988) Science. 240:1041-1043.

Examples of techniques which can be used to produce single-chain Fvs and antibodies include those described in U.S. Pat. Nos. 4,946,778 and 5,258,498. Thus, techniques described above and those well known in the art can be used to generate recombinant antibodies wherein the binding domain, e.g. ScFv, was isolated from a phage display library.

Antibody Purification and Isolation

Once an antibody molecule has been produced by recombinant or hybridoma expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences (referred to herein as "tags") to facilitate purification.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al. (1992) Bio/Technology. 10:163-167 describe a procedure for isolating antibodies which are secreted into the periplasmic space of *E. coli*. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc domain that is present in the antibody and will be understood by one of skill in the art. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody includes a $CH_3$ domain, the Bakerbond ABX resin (J.T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture that includes the antibody of interest and contaminants may be subjected to low pH hydrophobic interaction chromatography using an elution buffer at a pH between about 2.5-4.5, and performed at low salt concentrations (e.g., from about 0-0.25 M salt).

Thus, in certain embodiments is provided antibodies of the invention that are substantially purified/isolated. In one embodiment, these isolated/purified recombinantly expressed antibodies may be administered to a patient to mediate a prophylactic or therapeutic effect. A prophylactic is a medication or a treatment designed and used to prevent a disease, disorder or infection from occurring. A therapeutic is concerned specifically with the treatment of a particular disease, disorder or infection. A therapeutic dose is the amount needed to treat a particular disease, disorder or infection. In another embodiment these isolated/purified antibodies may be used to diagnose influenza virus infection, for example, influenza B virus infection, or, in other embodiments, influenza A and influenza B virus infection.

Human Antibodies

Human antibodies can be generated using methods well known in the art. Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient.

Human antibodies can be derived by in vitro methods. Suitable examples include but are not limited to phage display (MedImmune (formerly CAT), Morphosys, Dyax, Biosite/Medarex, Xoma, Symphogen, Alexion (formerly Proliferon), Affimed) ribosome display (MedImmune (formerly CAT)), yeast display, and the like. The phage display technology (See e.g., U.S. Pat. No. 5,969,108) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson and Chiswell (1993) Current Opinion in Structural Biology. 3:564-571. Several sources of V-gene segments can be used for phage display. Clackson et al. (1991) Nature. 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991) J. Mol. Biol. 222:581-597, or Griffith et al. (1993) EMBO J. 12:725-734. See, also, U.S. Pat. Nos. 5,565,332 and 5,573,905.

As discussed above, human antibodies may also be generated by in vitro activated B cells (see U.S. Pat. Nos. 5,567,610 and 5,229,275).

Immunoglobulin genes undergo various modifications during maturation of the immune response, including recombination between V, D and J gene segments, isotype switching, and hypermutation in the variable regions. Recombination and somatic hypermutation are the foundation for generation of antibody diversity and affinity maturation, but they can also generate sequence liabilities that may make commercial production of such immunoglobulins as therapeutic agents difficult or increase the immunogenicity risk of the antibody. In general, mutations in CDR regions are likely to contribute to improved affinity and function, while mutations in framework regions may increase the risk of immunogenicity. This risk can be reduced by reverting framework mutations to germline while ensuring that activity of the antibody is not adversely impacted. The diversification processes may also generate some structural liabilities or these structural liabilities may exist within germline sequences contributing to the heavy and light chain variable domains. Regardless of the source, it may be desirable to remove potential structural liabilities that may result in instability, aggregation, heterogeneity of product, or increased immunogenicity. Examples of undesirable liabilities include unpaired cysteines (which may lead to disulfide bond scrambling, or variable sulfhydryl adduct formation), N-linked glycosylation sites (resulting in heterogeneity of structure and activity), as well as deamidation (e.g. NG, NS), isomerization (DG), oxidation (exposed methionine), and hydrolysis (DP) sites.

Accordingly, in order to reduce the risk of immunogenicity and improve pharmaceutical properties, it may be desirable to revert a framework sequence to germline, revert a CDR to germline, and/or remove a structural liability.

Thus, in one embodiment, where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques.

Antibody Fragments

In certain embodiments, the present antibodies are antibody fragments or antibodies that include these fragments. The antibody fragment includes a portion of the full length antibody, which generally is the antigen binding or variable region thereof. Examples of antibody fragments include Fab, Fab', F(ab')$_2$, Fd and Fv fragments, diabodies; linear antibodies (U.S. Pat. No. 5,641,870) and single-chain antibody molecules.

Traditionally, these fragments were derived via proteolytic digestion of intact antibodies using techniques well known in the art. However, these fragments can now be produced directly by recombinant host cells. Fab, Fv and scFv antibody fragments can all be expressed in and secreted from E. coli, thus allowing the facile production of large amounts of these fragments. In one embodiment, the antibody fragments can be isolated from the antibody phage libraries discussed above. Alternatively, Fab'-SH fragments can also be directly recovered from E. coli and chemically coupled to form F(ab')$_2$ fragments (Carter et al. (1992) Bio/Technology. 10:163-167). According to another approach, F(ab')2 fragments can be isolated directly from recombinant host cell culture. Other techniques for the production of antibody fragments will be apparent to the skilled practitioner. In other embodiments, the antibody of choice is a single-chain Fv fragment (scFv). In certain embodiments, the antibody is not a Fab fragment. Fv and scFv are the only species with intact combining sites that are devoid of constant regions; thus, they are suitable for reduced nonspecific binding during in vivo use. scFv fusion proteins may be constructed to yield fusion of an effector protein at either the amino or the carboxy terminus of an scFv.

In certain embodiments, the present antibodies are domain antibodies, e.g., antibodies containing the small functional binding units of antibodies, corresponding to the variable regions of the heavy (VH) or light (VL) chains of human antibodies. Examples of domain antibodies include, but are not limited to, those of Domantis (see, for example, WO04/058821; WO04/081026; WO04/003019; WO03/002609; U.S. Pat. Nos. 6,291,158; 6,582,915; 6,696,245; and 6,593,081).

In certain embodiments of the invention, the present antibodies are linear antibodies. Linear antibodies include a pair of tandem Fd segments (VH-CH1-VH-CH1) which form a pair of antigen-binding regions. See, Zapata et al. (1995) Protein Eng. 8(10):1057-1062.

Other Amino Acid Sequence Modifications

In addition to the above described human, humanized and/or chimeric antibodies, the present invention also encompasses further modifications and, their variants and fragments thereof, of the antibodies of the invention including one or more amino acid residues and/or polypeptide substitutions, additions and/or deletions in the variable light (VL) domain and/or variable heavy (VH) domain and/or Fc region and post translational modifications. Included in these modifications are antibody conjugates wherein an antibody has been covalently attached to a moiety. Moieties suitable for attachment to the antibodies include but are not limited to, proteins, peptides, drugs, labels, and cytotoxins. These changes to the antibodies may be made to alter or fine tune the characteristics (biochemical, binding and/or functional) of the antibodies as is appropriate for treatment and/or diagnosis of influenza virus infection. Methods for forming conjugates, making amino acid and/or polypeptide changes and post-translational modifications are well known in the art, some of which are detailed below.

Amino acid changes to the antibodies necessarily results in sequences that are less than 100% identical to the above identified antibody sequences or parent antibody sequence. In certain embodiments, in this context, the antibodies many have about 25% to about 95% sequence identity to the amino acid sequence of either the heavy or light chain variable domain of an antibody as described herein. Thus, in one embodiment a modified antibody may have an amino acid sequence having at least 25%, 35%, 45%, 55%, 65%, 75%, 80%, 85%, 90%, 95%, 96%, 97%, 98% or 99% amino acid sequence identity or similarity with the amino acid sequence of either the heavy or light chain variable domain of an antibody as described herein. In another embodiment, an altered antibody may have an amino acid sequence having at least 25%, 35%, 45%, 55%, 65%, 75%, 80%, 85%, 90%, 95%, 96%, 97%, 98% or 99% amino acid sequence identity or similarity with the amino acid sequence of the heavy or light chain CDR-1, CDR-2, or CDR-3 of an antibody as described herein. In another embodiment, an altered antibody may have an amino acid sequence having at least 25%, 35%, 45%, 55%, 65%, 75%, 80%, 85%, 90%, 95%, 96%, 97%, 98% or 99% amino acid sequence identity or similarity with the amino acid sequence of the heavy or light chain FR1, FR2, FR3 or FR4 of an antibody as described herein.

In certain embodiments, altered antibodies are generated by one or more amino acid alterations (e.g., substitutions, deletion and/or additions) introduced in one or more of the variable regions of the antibody. In another embodiment, the amino acid alterations are introduced in the framework regions. One or more alterations of framework region residues may result in an improvement in the binding affinity of the antibody for the antigen. This may be especially true when these changes are made to humanized antibodies wherein the framework region may be from a different species than the CDR regions. Examples of framework region residues to modify include those which non-covalently bind antigen directly (Amit et al. (1986) Science. 233:747-753); interact with/effect the conformation of a CDR (Chothia et al. (1987) J. Mol. Biol. 196:901-917); and/or participate in the VL-VH interface (U.S. Pat. Nos. 5,225,539 and 6,548,640). In one embodiment, from about one to about five framework residues may be altered. Sometimes, this may be sufficient to yield an antibody mutant suitable for use in preclinical trials, even where none of the hypervariable region residues have been altered. Normally, however, an altered antibody will include additional hypervariable region alteration(s).

One useful procedure for generating altered antibodies is called "alanine scanning mutagenesis" (Cunningham and Wells (1989) Science. 244:1081-1085). In this method, one or more of the hypervariable region residue(s) are replaced by alanine or polyalanine residue(s) to alter the interaction of the amino acids with the target antigen. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way are screened for their biological activity as described herein.

In certain embodiments the substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display (Hawkins et al. (1992) J. Mol. Biol. 254:889-896 and Lowman et al. (1991) Biochemistry. 30(45):10832-10837)). Briefly, several hypervariable region sites (e.g., 6-7 sites) are mutated to generate all possible amino acid substitutions at each site. The antibody mutants thus generated are displayed in a monovalent fashion from filamentous phage particles as fusions to the gene III product of M13 packaged within each particle. The phage-displayed mutants are then screened for their biological activity (e.g., binding affinity) as herein disclosed.

Mutations in antibody sequences may include substitutions, deletions, including internal deletions, additions, including additions yielding fusion proteins, or conservative substitutions of amino acid residues within and/or adjacent to the amino acid sequence, but that result in a "silent" change, in that the change produces a functionally-equivalent antibody. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for a member of another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, fluoro-amino acids, designer amino acids such as β-methyl amino acids, Cα-methyl amino acids, Nα-methyl amino acids, and amino acid analogs in general.

In another embodiment, any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Variant Fc Regions

It is known that variants of the Fc region (e.g., amino acid substitutions and/or additions and/or deletions) enhance or diminish effector function of the antibody (See e.g., U.S. Pat. Nos. 5,624,821; 5,885,573; 6,538,124; 7,317,091; 5,648,260; 6,538,124; WO 03/074679; WO 04/029207; WO 04/099249; WO 99/58572; US Publication No. 2006/0134105; 2004/0132101; 2006/0008883) and may alter the pharmacokinetic properties (e.g. half-life) of the antibody (see, U.S. Pat. Nos. 6,277,375 and 7,083,784). Thus, in certain embodiments, the antibodies of the invention include an altered Fc region (also referred to herein as "variant Fc region") in which one or more alterations have been made in the Fc region in order to change functional and/or pharmacokinetic properties of the antibodies. Such alterations may result in a decrease or increase of C1q binding and complement dependent cytotoxicity (CDC) or of FcγR binding, for IgG, and antibody-dependent cellular cytotoxicity (ADCC), or antibody dependent cell-mediated phagocytosis (ADCP). The present invention encompasses the antibodies described herein with variant Fc regions wherein changes have been made to fine tune the effector function, enhancing or diminishing, providing a desired effector function. Accordingly, the antibodies of the invention include a variant Fc region (i.e., Fc regions that have been altered as discussed below). Antibodies of the invention having a variant Fc region are also referred to here as "Fc variant antibodies." As used herein native refers to the unmodified parental sequence and the antibody with a native Fc region is herein referred to as a "native Fc antibody". Fc variant antibodies can be generated by numerous methods well known to one skilled in the art. Non-limiting examples include, isolating antibody coding regions (e.g., from hybridoma) and making one or more desired substitutions in the Fc region of the isolated antibody coding region. Alternatively, the antigen-binding portion (e.g., variable regions) of an antibody may be sub-cloned into a vector encoding a variant Fc region. In one embodiment, the variant Fc region exhibits a similar level of inducing effector function as compared to the native Fc region. In another embodiment, the variant Fc region exhibits a higher induction of effector function as compared to the native Fc. Some specific embodiments of variant Fc regions are detailed infra. Methods for measuring effector function are well known in the art.

The effector function of an antibody is modified through changes in the Fc region, including but not limited to, amino acid substitutions, amino acid additions, amino acid deletions and changes in post-translational modifications to Fc amino acids (e.g. glycosylation). The methods described below may be used to fine tune the effector function of a present antibody, a ratio of the binding properties of the Fc region for the FcR (e.g., affinity and specificity), resulting in a therapeutic antibody with the desired properties.

It is understood that the Fc region, as used herein, includes the polypeptides that make up the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc includes immunoglobulin domains Cgamma2 and Cgamma3 (Cγ2 and Cγ3) and the hinge between Cgamma1 (Cγ1) and Cgamma2 (Cγ2).

Although the boundaries of the Fc region may vary, the human IgG heavy chain Fc region is can be defined to include residues C226 or P230 to its carboxyl-terminus, wherein the numbering is according to the EU index as set forth in Kabat. Fc may refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist.

In one embodiment, Fc variant antibodies exhibit altered binding affinity for one or more Fc receptors including, but not limited to, FcRn, FcγRI (CD64) including isoforms FcγRIA, FcγRIB, and FcγRIC, FcγRII (CD32 including isoforms FcγRIIA, FcγRIIB, and FcγRIIC), and FcγRIII (CD16, including isoforms FcγRIIIA and FcγRIIIB) as compared to an native Fc antibody.

In one embodiment, an Fc variant antibody has enhanced binding to one or more Fc ligand relative to a native Fc antibody. In another embodiment, the Fc variant antibody exhibits increased or decreased affinity for an Fc ligand that is at least 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, and up to 25 fold, or up to 50 fold, or up to 75 fold, or up to 100 fold, or up to 200 fold, or is between 2 fold and 10 fold, or between 5 fold and 50 fold, or between 25 fold and 100 fold, or between 75 fold and 200 fold, or between 100 and 200 fold, more or less than a native Fc antibody. In another embodiment, Fc variant antibodies exhibit affinities for an Fc ligand that are at least 90%, at least 80%, at least 70%, at least 60%, at least 50%, at least 40%, at least 30%, at least 20%, at least 10%, or at least 5% more or less than an native Fc antibody. In certain embodiments, an Fc variant antibody has increased affinity for an Fc ligand. In other embodiments, an Fc variant antibody has decreased affinity for an Fc ligand.

In a specific embodiment, an Fc variant antibody has enhanced binding to the Fc receptor FcγRIIIA. In another specific embodiment, an Fc variant antibody has enhanced binding to the Fc receptor FcγRIIB. In a further specific embodiment, an Fc variant antibody has enhanced binding to both the Fc receptors FcγRIIIA and FcγRIIB. In certain embodiments, Fc variant antibodies that have enhanced binding to FcγRIIIA do not have a concomitant increase in binding the FcγRIIB receptor as compared to a native Fc antibody.

In a specific embodiment, an Fc variant antibody has reduced binding to the Fc receptor FcγRIIIA. In a further specific embodiment, an Fc variant antibody has reduced binding to the Fc receptor FcγRIIB. In still another specific embodiment, an Fc variant antibody exhibiting altered affinity for FcγRIIIA and/or FcγRIIB has enhanced binding to the Fc receptor FcRn. In yet another specific embodiment, an Fc variant antibody exhibiting altered affinity for FcγRIIIA and/or FcγRIIB has altered binding to C1q relative to a native Fc antibody.

In one embodiment, Fc variant antibodies exhibit affinities for FcγRIIIA receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or up to 50 fold, or up to 60 fold, or up to 70 fold, or up to 80 fold, or up to 90 fold, or up to 100 fold, or up to 200 fold, or are between 2 fold and 10 fold, or between 5 fold and 50 fold, or between 25 fold and 100 fold, or between 75 fold and 200 fold, or between 100 and 200 fold, more or less than an native Fc antibody. In another embodiment, Fc variant antibodies exhibit affinities for FcγRIIIA that are at least 90%, at least 80%, at least 70%, at least 60%, at least 50%, at least 40%, at least 30%, at least 20%, at least 10%, or at least 5% more or less than an native Fc antibody.

In one embodiment, Fc variant antibodies exhibit affinities for FcγRIIB receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or up to 50 fold, or up to 60 fold, or up to 70 fold, or up to 80 fold, or up to 90 fold, or up to 100 fold, or up to 200 fold, or are between 2 fold and 10 fold, or between 5 fold and 50 fold, or between 25 fold and 100 fold, or between 75 fold and 200 fold, or between 100 and 200 fold, more or less than an native Fc antibody. In another embodiment, Fc variant antibodies exhibit affinities for FcγRIIB that are at least 90%, at least 80%, at least 70%, at least 60%, at least 50%, at least 40%, at least 30%, at least 20%, at least 10%, or at least 5% more or less than an native Fc antibody.

In one embodiment, Fc variant antibodies exhibit increased or decreased affinities to C1q relative to a native Fc antibody. In another embodiment, Fc variant antibodies exhibit affinities for C1q receptor that are at least 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or up to 50 fold, or up to 60 fold, or up to 70 fold, or up to 80 fold, or up to 90 fold, or up to 100 fold, or up to 200 fold, or are between 2 fold and 10 fold, or between 5 fold and 50 fold, or between 25 fold and 100 fold, or between 75 fold and 200 fold, or between 100 and 200 fold, more or less than an native Fc antibody. In another embodiment, Fc variant antibodies exhibit affinities for C1q that are at least 90%, at least 80%, at least 70%, at least 60%, at least 50%, at least 40%, at least 30%, at least 20%, at least 10%, or at least 5% more or less than an native Fc antibody. In still another specific embodiment, an Fc variant antibody exhibiting altered affinity for Ciq has enhanced binding to the Fc receptor FcRn. In yet another specific embodiment, an Fc variant antibody exhibiting altered affinity for C1q has altered binding to FcγRIIIA and/or FcγRIIB relative to a native Fc antibody.

It is well known in the art that antibodies are capable of directing the attack and destruction through multiple processes collectively known in the art as antibody effector functions. One of these processes, known as "antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing cells and subsequently kill the cells with cytotoxins. Specific high-affinity IgG antibodies directed to the surface of cells "arm" the cytotoxic cells and are required for such killing. Lysis of the cell is extracellular, requires direct cell-to-cell contact, and does not involve complement.

Another process encompassed by the term effector function is complement dependent cytotoxicity (hereinafter referred to as "CDC") which refers to a biochemical event of cell destruction by the complement system. The complement system is a complex system of proteins found in normal blood plasma that combines with antibodies to destroy pathogenic bacteria and other foreign cells.

Still another process encompassed by the term effector function is antibody dependent cell-mediated phagocytosis (ADCP) which refers to a cell-mediated reaction wherein nonspecific cytotoxic cells that express one or more effector ligands recognize bound antibody on a cell and subsequently cause phagocytosis of the cell.

It is contemplated that Fc variant antibodies are characterized by in vitro functional assays for determining one or more FcγR mediated effector cell functions. In certain embodiments, Fc variant antibodies have similar binding properties and effector cell functions in in vivo models (such as those described and disclosed herein) as those in in vitro based assays. However, the present invention does not exclude Fc variant antibodies that do not exhibit the desired phenotype in in vitro based assays but do exhibit the desired phenotype in vivo.

In certain embodiments, an antibody having an Fc variant has enhanced cytotoxicity or phagocytosis activity (e.g., ADCC, CDC and ADCP) relative to an antibody with a native Fc region. In a specific embodiment, an Fc variant antibody has cytotoxicity or phagocytosis activity that is at least 2 fold, or at least 3 fold, or at least 5 fold or at least 10 fold or at least 50 fold or at least 100 fold, or up to 50 fold, or up to 75 fold, or up to 100 fold, or up to 200 fold, or is between 2 fold and 10 fold, or between 5 fold and 50 fold, or between 25 fold and 100 fold, or between 75 fold and 200 fold, or between 100 and 200 fold, greater than that of a native Fc antibody. Alternatively, an Fc variant antibody has reduced cytotoxicity or phagocytosis activity relative to a native Fc antibody. In a specific embodiment, an Fc variant antibody has cytotoxicity or phagocytosis activity that is at least 2 fold, or at least 3 fold, or at least 5 fold or at least 10 fold or at least 50 fold or at least 100 fold, or up to 50 fold, or up to 75 fold, or up to 100 fold, or up to 200 fold, or is between 2 fold and 10 fold, or between 5 fold and 50 fold, or between 25 fold and 100 fold, or between 75 fold and 200 fold, or between 100 and 200 fold, lower than that of a native Fc antibody.

In certain embodiments, Fc variant antibodies exhibit decreased ADCC activities as compared to a native Fc antibody. In another embodiment, Fc variant antibodies exhibit ADCC activities that are at least 2 fold, or at least 3 fold, or at least 5 fold or at least 10 fold or at least 50 fold or at least 100 fold, or up to 50 fold, or up to 75 fold, or up to 100 fold, or up to 200 fold, or is between 2 fold and 10 fold, or between 5 fold and 50 fold, or between 25 fold and 100 fold, or between 75 fold and 200 fold, or between 100 and 200 fold, less than that of a native Fc antibody. In still another embodiment, Fc variant antibodies exhibit ADCC activities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500%, relative to a native Fc antibody. In certain embodiments, Fc variant antibodies have no detectable ADCC activity. In specific embodiments, the reduction and/or ablatement of ADCC activity may be attributed to the reduced affinity Fc variant antibodies exhibit for Fc ligands and/or receptors.

In an alternative embodiment, Fc variant antibodies exhibit increased ADCC activities as compared to a native Fc antibody. In another embodiment, Fc variant antibodies exhibit ADCC activities that are at least 2 fold, or at least 3 fold, or at least 5 fold or at least 10 fold or at least 50 fold or at least 100 fold greater than that of a native Fc antibody. In still another embodiment, Fc variant antibodies exhibit ADCC activities that are increased by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a native Fc antibody. In specific embodiments, the increased ADCC activity may be attributed to the increased affinity Fc variant antibodies exhibit for Fc ligands and/or receptors.

In a specific embodiment, an Fc variant antibody has enhanced binding to the Fc receptor FcγRIIIA and has enhanced ADCC activity relative to a native Fc antibody. In other embodiments, the Fc variant antibody has both enhanced ADCC activity and enhanced serum half-life relative to a native Fc antibody. In another specific embodiment, an Fc variant antibody has reduced binding to the Fc receptor FcγRIIIA and has reduced ADCC activity relative to a native Fc antibody. In other embodiments, the Fc variant antibody has both reduced ADCC activity and enhanced serum half-life relative to a native Fc antibody.

In certain embodiments, the cytotoxicity is mediated by CDC wherein the Fc variant antibody has either enhanced or decreased CDC activity relative to a native Fc antibody. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al. (1996) J. Immunol. Methods, 202:163, may be performed.

In one embodiment, antibodies of the invention exhibit increased CDC activity as compared to a native Fc antibody. In another embodiment, Fc variant antibodies exhibit CDC activity that is at least 2 fold, or at least 3 fold, or at least 5 fold or at least 10 fold or at least 50 fold or at least 100 fold, or up to 50 fold, or up to 75 fold, or up to 100 fold, or up to 200 fold, or is between 2 fold and 10 fold, or between 5 fold and 50 fold, or between 25 fold and 100 fold, or between 75 fold and 200 fold, or between 100 and 200 fold more than that of an native Fc antibody. In still another embodiment, Fc variant antibodies exhibit CDC activity that is increased by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a native Fc antibody. In specific embodiments, the increase of CDC activity may be attributed to the increased affinity Fc variant antibodies exhibit for C1q.

Antibodies of the invention may exhibit increased CDC activity as compared to a native Fc antibody by virtue of COMPLEGENT® Technology (Kyowa Hakko Kirin Co., Ltd.), which enhances one of the major mechanisms of action of an antibody, CDC. With an approach called isotype chimerism, in which portions of IgG3, an antibody's isotype, are introduced into corresponding regions of IgG1, the standard isotype for therapeutic antibodies, COMPLEGENT® Technology significantly enhances CDC activity beyond that of either IgG1 or IgG3, while retaining the desirable features of IgG1, such as ADCC, PK profile and Protein A binding. In addition, it can be used together with POTELLIGENT® Technology, creating an even superior therapeutic Mab (ACCRETAMAB®) with enhanced ADCC and CDC activities Fc variant antibody of the invention may have enhanced ADCC activity and enhanced serum half-life relative to a native Fc antibody.

Fc variant antibody of the invention may CDC activity and enhanced serum half-life relative to a native Fc antibody.

Fc variant antibody of the invention may have enhanced ADCC activity, enhanced CDC activity and enhanced serum half-life relative to a native Fc antibody.

The serum half-life of proteins having Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The increase in half-life allows for the reduction in amount of drug given to a patient as well as reducing the frequency of administration. To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Alternatively, antibodies of the invention with increased half-lives may be generated by modifying amino acid residues identified as involved in the interaction between the Fc and the FcRn receptor (see, for examples, U.S. Pat. Nos. 6,821,505 and 7,083,784; and WO 09/058492). In addition, the half-life of antibodies of the invention may be increase by conjugation to PEG or Albumin by techniques widely utilized in the art. In some embodiments antibodies having Fc variant regions of the invention have an increased half-life of about 5%, about 10%, about 15%, about 20%, about 25%, about 30%, about 35%, about 40%, about 45%, about 50%, about 60%, about 65%, about 70%, about 80%, about 85%, about 90%, about 95%, about 100%, about 125%, about 150% or more as compared to an antibody having a native Fc region. In some embodiments antibodies having Fc variant regions have an increased half-life of about 2 fold, about 3 fold, about 4 fold, about 5 fold, about 10 fold, about 20 fold, about 50 fold or more, or up to about 10 fold, about 20 fold, or about 50 fold, or between 2 fold and 10 fold, or between 5 fold and 25 fold, or between 15 fold and 50 fold, as compared to an antibody with a native Fc region.

In one embodiment, the present invention provides Fc variants, wherein the Fc region includes a modification (e.g., amino acid substitutions, amino acid insertions, amino acid deletions) at one or more positions selected from 221, 225, 228, 234, 235, 236, 237, 238, 239, 240, 241, 243, 244, 245, 247, 250, 251, 252, 254, 255, 256, 257, 262, 263, 264, 265, 266, 267, 268, 269, 279, 280, 284, 292, 296, 297, 298, 299, 305, 308, 313, 316, 318, 320, 322, 325, 326, 327, 328, 329, 330, 331, 332, 333, 334, 339, 341, 343, 370, 373, 378, 392, 416, 419, 421, 428, 433, 434, 435, 436, 440, and 443 as numbered by the EU index as set forth in Kabat. Optionally, the Fc region may include a modification at additional and/or alternative positions known to one skilled in the art (see, e.g., U.S. Pat. Nos. 5,624,821; 6,277,375; 6,737,056; 7,083,784; 7,317,091; 7,217,797; 7,276,585; 7,355,008; 2002/0147311; 2004/0002587; 2005/0215768; 2007/0135620; 2007/0224188; 2008/0089892; WO 94/29351; and WO 99/58572). Additional, useful amino acid positions and specific substitutions are exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8-10, 13 and 14 of WO 09/058492.

In a specific embodiment, the present invention provides an Fc variant, wherein the Fc region includes at least one substitution selected from 221K, 221Y, 225E, 225K, 225W, 228P, 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241L, 241Y, 241E, 241R. 243W, 243L 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264 I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F, 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330 I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 424F, 434W, 434Y, 436H, 440Y and 443W as numbered by the EU index as set forth in Kabat. Optionally, the Fc region may include additional and/or alternative amino acid substitutions known to one skilled in the art including but not limited to those exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8, 9 and 10 of WO 09/058492.

In a specific embodiment, the present invention provides an Fc variant antibody, wherein the Fc region includes at least one modification (e.g., amino acid substitutions, amino acid insertions, amino acid deletions) at one or more positions selected from 228, 234, 235 and 331 as numbered by the EU index as set forth in Kabat. In one embodiment, the modification is at least one substitution selected from 228P, 234F, 235E, 235F, 235Y, and 331S as numbered by the EU index as set forth in Kabat.

In another specific embodiment, the present invention provides an Fc variant antibody, wherein the Fc region is an IgG4 Fc region and includes at least one modification at one or more positions selected from 228 and 235 as numbered by the EU index as set forth in Kabat. In still another specific embodiment, the Fc region is an IgG4 Fc region and the non-naturally occurring amino acids are selected from 228P, 235E and 235Y as numbered by the EU index as set forth in Kabat.

In another specific embodiment, the present invention provides an Fc variant, wherein the Fc region includes at least one non-naturally occurring amino acid at one or more positions selected from 239, 330 and 332 as numbered by the EU index as set forth in Kabat. In one embodiment, the modification is at least one substitution selected from 239D, 330L, 330Y, and 332E as numbered by the EU index as set forth in Kabat.

In a specific embodiment, the present invention provides an Fc variant antibody, wherein the Fc region includes at least one non-naturally occurring amino acid at one or more positions selected from 252, 254, and 256 as numbered by the EU index as set forth in Kabat. In one embodiment, the modification is at least one substitution selected from 252Y, 254T and 256E as numbered by the EU index as set forth in Kabat. In particularly preferred antibodies of the invention, the modification is three substitutions 252Y, 254T and 256E as numbered by the EU index as set forth in Kabat (known as "YTE"), see U.S. Pat. No. 7,083,784.

In certain embodiments the effector functions elicited by IgG antibodies strongly depend on the carbohydrate moiety linked to the Fc region of the protein (Ferrara et al. (2006) Biotechnology and Bioengineering. 93:851-861). Thus, glycosylation of the Fc region can be modified to increase or decrease effector function (see for examples, Umana et al. (1999) Nat. Biotechnol. 17:176-180; Davies et al. (2001) Biotechnol Bioeng. 74:288-294; Shields et al. (2002) J Biol Chem. 277:26733-26740; Shinkawa et al. (2003) J Biol Chem. 278:3466-3473; U.S. Pat. Nos. 6,602,684; 6,946,292; 7,064,191; 7,214,775; 7,393,683; 7,425,446; 7,504,256; U.S. Publication. Nos. 2003/0157108; 2003/0003097; 2009/0010921; Potilegent™ technology (Biowa, Inc. Princeton, N.J.); GlycoMAb™ glycosylation engineering technology (GLYCART biotechnology AG, Zurich, Switzerland)). Accordingly, in one embodiment the Fc regions of antibodies of the invention include altered glycosylation of amino acid residues. In another embodiment, the altered glycosylation of the amino acid residues results in lowered effector function. In another embodiment, the altered glycosylation of the amino acid residues results in increased effector function. In a specific embodiment, the Fc region has reduced fucosylation. In another embodiment, the Fc region is afucosylated (see for examples, U.S. Patent Application Publication No. 2005/0226867). In one aspect, these antibodies with increased effector function, specifically ADCC, as generated in host cells (e.g., CHO cells, *Lemna minor*) engineered to produce highly defucosylated antibody with over 100-fold higher ADCC compared to antibody produced by the parental cells (Mori et al. (2004) Biotechnol Bioeng. 88:901-908; Cox et al. (2006) Nat Biotechnol. 24:1591-7).

Addition of sialic acid to the oligosaccharides on IgG molecules can enhance their anti-inflammatory activity and alters their cytotoxicity (Keneko et al. (2006) Science. 313:670-673; Scallon et al. (2007) Mol. Immuno. 44(7):

1524-34). The studies referenced above demonstrate that IgG molecules with increased sialylation have anti-inflammatory properties whereas IgG molecules with reduced sialylation have increased immunostimulatory properties (e.g., increase ADCC activity). Therefore, an antibody can be modified with an appropriate sialylation profile for a particular therapeutic application (US Publication No. 2009/0004179 and International Publication No. WO 2007/005786).

In one embodiment, the Fc regions of antibodies of the invention include an altered sialylation profile compared to the native Fc region. In one embodiment, the Fc regions of antibodies of the invention include an increased sialylation profile compared to the native Fc region. In another embodiment, the Fc regions of antibodies of the invention include a decreased sialylation profile compared to the native Fc region.

In one embodiment, the Fc variants of the present invention may be combined with other known Fc variants such as those disclosed in Ghetie et al. (1997) Nat Biotech. 15:637-40; Duncan et al. (1988) Nature. 332:563-564; Lund et al. (1991) J. Immunol. 147:2657-2662; Lund et al. (1992) Mol Immunol. 29:53-59; Alegre et al. (1994) Transplantation. 57:1537-1543; Hutchins et al. (1995) Proc Natl. Acad. Sci. USA. 92:11980-11984; Jefferis et al. (1995) Immunol Lett. 44:111-117; Lund et al. (1995) Faseb. J. 9:115-119; Jefferis et al. (1996) Immunol. Lett. 54:101-104; Lund et al. (1996) J. Immunol. 157:4963-4969; Armour et al. (1999) Eur. J. Immunol. 29:2613-2624; Idusogie et al. (2000) J. Immunol. 164:4178-4184; Reddy et al. (2000) J. Immunol. 164:1925-1933; Xu et al. (2000) Cell. Immunol. 200:16-26; Idusogie et al. (2001) J. Immunol. 166:2571-2575; Shields et al. (2001) J. Biol. Chem. 276:6591-6604; Jefferis et al. (2002) Immunol. Lett. 82:57-65; Presta et al. (2002) Biochem. Soc. Trans. 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008; 2004/0002587; and WO 99/58572. Other modifications and/or substitutions and/or additions and/or deletions of the Fc domain will be readily apparent to one skilled in the art.

Glycosylation

In addition to the ability of glycosylation to alter the effector function of antibodies, modified glycosylation in the variable region can alter the affinity of the antibody for antigen. In one embodiment, the glycosylation pattern in the variable region of the present antibodies is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861. One or more amino acid substitutions can also be made that result in elimination of a glycosylation site present in the Fc region (e.g., Asparagine 297 of IgG). Furthermore, aglycosylated antibodies may be produced in bacterial cells which lack the necessary glycosylation machinery.

Antibody Conjugates

In certain embodiments, the antibodies of the invention are conjugated or covalently attached to a substance using methods well known in the art. In one embodiment, the attached substance is a therapeutic agent, a detectable label (also referred to herein as a reporter molecule) or a solid support. Suitable substances for attachment to antibodies include, but are not limited to, an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a virus, a fluorophore, a chromophore, a dye, a toxin, a hapten, an enzyme, an antibody, an antibody fragment, a radioisotope, solid matrixes, semi-solid matrixes and combinations thereof. Methods for conjugation or covalently attaching another substance to an antibody are well known in the art.

In certain embodiments, the antibodies of the invention are conjugated to a solid support. Antibodies may be conjugated to a solid support as part of the screening and/or purification and/or manufacturing process. Alternatively antibodies of the invention may be conjugated to a solid support as part of a diagnostic method or composition. A solid support suitable for use in the present invention is typically substantially insoluble in liquid phases. A large number of supports are available and are known to one of ordinary skill in the art. Thus, solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and non-conducting metals, glass (including microscope slides) and magnetic supports. More specific examples of solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the antibodies of the invention.

A suitable solid phase support can be selected on the basis of desired end use and suitability for various synthetic protocols. For example, where amide bond formation is desirable to attach the antibodies of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (Tenta-Gel™, Rapp Polymere, Tubingen, Germany), polydimethylacrylamide resin (available from Milligen/Biosearch, California), or PEGA beads (obtained from Polymer Laboratories).

In certain embodiments, the antibodies of the invention are conjugated to labels for purposes of diagnostics and other assays wherein the antibody and/or its associated ligand may be detected. A label conjugated to an antibody and used in the present methods and compositions described herein, is any chemical moiety, organic or inorganic, that exhibits an absorption maximum at wavelengths greater than 280 nm, and retains its spectral properties when covalently attached to an antibody. Labels include, without limitation, a chromophore, a fluorophore, a fluorescent protein, a phosphorescent dye, a tandem dye, a particle, a hapten, an enzyme and a radioisotope.

In certain embodiments, the antibodies are conjugated to a fluorophore. As such, fluorophores used to label antibodies of the invention include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1, 3-diazole (NBD), a cyanine (including any corresponding compounds in U.S. Pat. Nos. 6,977,305 and 6,974,873), a carbocyanine (including any corresponding compounds in U.S. Ser. No. 09/557,275; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343; 5,227,487; 5,442,045; 5,798,276; 5,846,737; 4,945,171; U.S. Ser. Nos. 09/129,015 and 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in 5,242,805), aminooxazinones, diaminooxazines, and their benzo-substituted analogs.

In a specific embodiment, the fluorophores conjugated to the antibodies described herein include xanthene (rhodol, rhodamine, fluorescein and derivatives thereof) coumarin, cyanine, pyrene, oxazine and borapolyazaindacene. In other embodiments, such fluorophores are sulfonated xanthenes, fluorinated xanthenes, sulfonated coumarins, fluorinated coumarins and sulfonated cyanines. Also included are dyes sold under the tradenames, and generally known as, ALEXA FLUOR®, DyLight, CY® Dyes, BODIPY®, OREGON GREEN®, PACIFIC BLUE™, IRDYE®, FAM, FITC, and ROX™.

The choice of the fluorophore attached to the antibody will determine the absorption and fluorescence emission properties of the conjugated antibody. Physical properties of a fluorophore label that can be used for antibody and antibody bound ligands include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain embodiments, the fluorophore has an absorption maximum at wavelengths greater than 480 nm. In other embodiments, the fluorophore absorbs at or near 488 nm to 514 nm (particularly suitable for excitation by the output of the argon-ion laser excitation source) or near 546 nm (particularly suitable for excitation by a mercury arc lamp). In other embodiment a fluorophore can emit in the NIR (near infrared region) for tissue or whole organism applications. Other desirable properties of the fluorescent label may include cell permeability and low toxicity, for example if labeling of the antibody is to be performed in a cell or an organism (e.g., a living animal).

In certain embodiments, an enzyme is a label and is conjugated to an antibody described herein. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the preferred measurable product, e.g. colorimetric, fluorescent or chemiluminescence. Such substrates are extensively used in the art and are well known by one skilled in the art.

In one embodiment, colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042) and reduced dihydroxanthenes, including dihydrofluoresceins (U.S. Pat. No. 6,162,931) and dihydrorhodamines including dihydrorhodamine 123. Peroxidase substrates that are tyramides (U.S. Pat. Nos. 5,196,306; 5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label antigen in samples that are cells, tissues or arrays for their subsequent detection by microscopy, flow cytometry, optical scanning and fluorometry.

In another embodiment, a colorimetric (and in some cases fluorogenic) substrate and enzyme combination uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912) fluorescein diphosphate, 3-O-methylfluorescein phosphate, resorufin phosphate, 9H-(1,3-dichloro-9,9-dimethylacridin-2-one-7- yl) phosphate (DDAO phosphate), or ELF 97, ELF 39 or related phosphates (U.S. Pat. Nos. 5,316,906 and 5,443, 986).

Glycosidases, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. In one embodiment, fluorogenic substrates include resorufin beta-D-galactopyranoside, fluorescein digalactoside (FDG), fluorescein digalacuronide and their structural variants (U.S. Pat. Nos. 5,208,148; 5,242,805; 5,362,628; 5,576,424 and 5,773,236), 4-methylumbelliferyl beta-D-galactopyranoside, carboxyumbelliferyl beta-D-galactopyranoside and fluorinated coumarin beta-D-galactopyranosides (U.S. Pat. No. 5,830,912).

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In another embodiment, haptens such as biotin, are also utilized as labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, effector molecules, growth factors, chemokines, cytokines, lymphokines, amino acids, peptides, chemical intermediates, nucleotides and the like.

In certain embodiments, fluorescent proteins may be conjugated to the antibodies as a label. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes include a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of antigen in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorphore then emits at a wavelength farther from the fluorescent proteins than could have been obtained with only the fluorescent protein. A particularly useful combination is the phycobiliproteins disclosed in U.S. Pat. Nos. 4,520,110; 4,859,582; 5,055,556 and the sulforhodamine fluorophores disclosed in U.S. Pat. No. 5,798,276, or the sulfonated cyanine fluorophores disclosed in U.S. Pat. Nos. 6,977,305 and 6,974,873; or the sulfonated xanthene derivatives disclosed in U.S. Pat. No. 6,130,101 and those combinations disclosed in U.S. Pat. No. 4,542,104. Alternatively, the fluorophore functions as the energy donor and the fluorescent protein is the energy acceptor.

In certain embodiments, the label is a radioactive isotope. Examples of suitable radioactive materials include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18F}$), $^{153}$Sm, $^{177}$Lu, $^{159}$Gd, $^{149}$Pm, $^{140}$La, $^{175}$Yb, $^{166}$Ho, $^{99}$Y, $^{47}$Sd, $^{186}$Re, $^{188}$Re, $^{142}$Pr, $^{105}$Rh, and $^{97}$Ru.

Medical Treatments and Uses

The antibodies and antigen binding fragments thereof of the invention and variants thereof may be used for the treatment of influenza B virus infection, for the prevention of influenza B virus infection; for the detection, diagnosis and/or prognosis of influenza B virus infection; or combinations thereof. In one embodiment, the antibodies and antigen binding fragments thereof of the inventions and variants thereof may be used for the treatment of influenza A and influenza B infection, for the prevention of influenza A and influenza B; for the detection, diagnosis and/or prognosis of influenza A and influenza B infection; or combinations thereof.

Methods of diagnosis may include contacting an antibody or an antibody fragment with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of detection, diagnosis, and/or prognosis may also include the detection of an antigen/antibody complex.

In one embodiment, the invention provides a method of treating a subject by administering to the subject an effective amount of an antibody or an antigen binding fragment thereof, according to the invention, or a pharmaceutical composition that includes the antibody or antigen binding fragment thereof. In one embodiment, the antibody or antigen binding fragment thereof is substantially purified (i.e., substantially free from substances that limit its effect or produce undesired side-effects). In one embodiment, the antibody or antigen binding fragment thereof of the invention is administered post-exposure, or after the subject has been exposed to influenza B virus or is infected with influenza B virus. In one embodiment, the antibody or antigen binding fragment thereof of the invention is administered post-exposure, or after the subject has been exposed to influenza B virus of Yamagata and/or Victoria lineage or is infected with influenza B virus of Yamagata and/or Victoria lineage. In one embodiment, the antibody or antigen binding fragment thereof of the invention is administered post-exposure, or after the subject has been exposed to at least one influenza A virus subtype; influenza B virus of Yamagata lineage; influenza B virus of Victoria lineage, or combinations thereof; or is infected with at least one influenza A virus subtype and/or influenza B virus of Yamagata and/or Victoria lineage.

In another embodiment, the antibody or antigen binding fragment thereof of the invention is administered pre-exposure, or to a subject that has not yet been exposed to influenza B virus or is not yet infected with influenza B virus. In another embodiment, the antibody or antigen binding fragment thereof of the invention is administered pre-exposure, or to a subject that has not yet been exposed to influenza B virus of Yamagata and/or Victoria lineage or is not yet infected with influenza B virus of Yamagata and/or Victoria lineage. In another embodiment, the antibody or antigen binding fragment thereof of the invention is administered pre-exposure, or to a subject that has not yet been exposed to influenza A virus; influenza B virus of Yamagata lineage; influenza B virus of Victoria lineage; or combinations thereof, or is not yet infected with influenza A virus; influenza B virus of Yamagata lineage; influenza of Victoria lineage; or combinations thereof.

In one embodiment, the antibody or antigen binding fragment thereof of the invention is administered to a subject that is sero-negative for one or more influenza B viruses. In one embodiment, the antibody or antigen binding fragment thereof of the invention is administered to a subject that is sero-negative for one or more influenza B virus lineages. In one embodiment, the antibody or antigen binding fragment thereof of the invention is administered to a subject that is sero-negative for one or more influenza A subtypes and/or one or more influenza B viruses.

In another embodiment, the antibody or antigen binding fragment thereof of the invention is administered to a subject that is sero-positive for one or more one or more influenza B viruses. In another embodiment, the antibody or antigen binding fragment thereof of the invention is administered to a subject that is sero-positive for one or more one or more influenza B virus lineages. In another embodiment, the antibody or antigen binding fragment thereof of the invention is administered to a subject that is sero-positive for one or more one or more influenza A virus subtypes and/or one or more influenza B viruses. In one embodiment, the antibody or antigen binding fragment thereof of the invention is administered to a subject within 1, 2, 3, 4, 5 days of infection or symptom onset. In another embodiment, the antibody or antigen binding fragment thereof of the invention can be administered to a subject after 1, 2, 3, 4, 5, 6, or 7 days, and within 2, 3, 4, 5, 6, 7, 8, 9 or 10 days after infection or symptom onset.

In one embodiment, the method reduces influenza B virus infection in a subject. In another embodiment, the method reduces influenza A virus infection and/or influenza B virus infection in a subject. In another embodiment, the method prevents, reduces the risk or delays influenza B virus infection in a subject. In another embodiment, the method prevents, reduces the risk or delays influenza A and/or influenza B virus infection in a subject. In one embodiment, the subject is an animal. In one embodiment, the subject is a mammal. In a more particular embodiment, the subject is human. In one embodiment, the subject includes, but is not limited to, one who is particularly at risk of or susceptible to influenza A and/or influenza B virus infection, including, for example, an immunocompromised subject.

Treatment can be a single dose schedule or a multiple dose schedule and the antibody or antigen binding fragment thereof of the invention can be used in passive immunization or active vaccination.

In one embodiment, the antibody or antigen binding fragment thereof of the invention is administered to a subject in combination with one or more antiviral medications. In one embodiment, the antibody or antigen binding fragment thereof of the invention is administered to a subject in combination with one or more small molecule antiviral medications. Small molecule antiviral medications include neuraminidase inhibitors such as oseltamivir (TAMIFLU®), zanamivir (RELENZA®) and adamantanes such as Amantadine and rimantadine.

In another embodiment, the invention provides a composition for use as a medicament for the prevention or treatment of an influenza A and/or influenza B virus infection. In another embodiment, the invention provides the use of an antibody or antigen binding fragment thereof of the invention and/or a protein having an epitope to which an antibody or antigen binding fragment thereof of the invention binds in the manufacture of a medicament for treatment of a subject and/or diagnosis in a subject.

Antibodies and fragments thereof as described in the present invention may also be used in a kit for the diagnosis of influenza A virus infection; influenza B virus infection; or combinations thereof. Further, epitopes capable of binding an antibody of the invention may be used in a kit for monitoring the efficacy of vaccination procedures by detecting the presence of protective anti-influenza A and/or influenza B virus antibodies. Antibodies, antibody fragment, or variants and derivatives thereof, as described in the present invention may also be used in a kit for monitoring vaccine manufacture with the desired immunogenicity.

The invention also provides a method of preparing a pharmaceutical composition, which includes the step of admixing a monoclonal antibody with one or more pharmaceutically-acceptable carriers, wherein the antibody is a monoclonal antibody according to the invention described herein.

Various delivery systems are known and can be used to administer the antibody or antigen binding fragment thereof of the invention, including, but not limited to, encapsulation in liposomes, microparticles, microcapsules, recombinant cells capable of expressing the antibody or antibody fragment, receptor-mediated endocytosis, construction of a nucleic acid as part of a retroviral or other vector, etc. Methods of introduction include, but are not limited to, intradermal, intramuscular, intraperitoneal, intravenous, subcutaneous, intranasal, epidural, and oral routes. In another embodiment, the vaccine can be administered as a DNA vaccine, for example using electroporation technology, including, but not limited to, in vivo electroporation. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents, including, but not limited to small molecule antiviral compositions. Administration can be systemic or local. Pulmonary administration can also be employed, e.g., by use of an inhaler or nebulizer, and formulation with an aerosolizing agent. In yet another embodiment, the composition can be delivered in a controlled release system.

The present invention also provides pharmaceutical compositions. Such compositions include a therapeutically effective amount of an antibody or antigen binding fragment thereof of the invention, and a pharmaceutically acceptable carrier. The term "pharmaceutically acceptable" as used herein, means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. In one embodiment, the pharmaceutical composition contains a therapeutically effective amount of the antibody or antigen binding fragment thereof, preferably in purified form, together with a suitable amount of carrier so as to provide the form for proper administration to the patient. The formulation should suit the mode of administration.

Typically, for antibody therapeutics, the dosage administered to a patient is between about 0.1 mg/kg to 100 mg/kg of the patient's body weight.

EXAMPLES

Example 1. Construction and Optimization of Human Monoclonal Antibodies Isolated from Memory B Cells CD22+ IgG+ B cells were sorted from cryopreserved peripheral blood mononuclear cells (PBMCs) of a donor selected for high neutralizing titers against both B/Florida/4/2006 Yamagata lineage (B/FLA/06) and B/Brisbane/60/2008 Victoria Lineage (B/BNE/08) and immortalized at 3 cells/well using Epstein Barr Virus (EBV), CpG oligodeoxynucleotide 2006 and feeder cells. Culture supernatants containing antibodies were harvested after 14 days and screened by microneutralization assay (MNA) that was modified from a previously described accelerated viral inhibition assay using neuraminidase activity (NA) as a read-out (Hassantoufighi et al. (2010) Vaccine. 28:790-7) to identify antibody clones that could neutralize viruses from both Yamagata and Victoria influenza B lineages.

In brief 10 µl of culture supernatant was incubated with 400 TCID50 of influenza B/BNE/08 (Victoria lineage) or B/FLA/06 (Yamagata lineage) for one hour at 37° C. Madin-Darby canine kidney (MDCK) cells were added to the plates (20'000 cells per well), incubated for 4 hours, washed twice with TPCK-trypsin containing medium and then incubated for 2 days at 37° C. After incubation, NA activity was measured by adding a fluorescently-labelled substrate, methylumbelliferyl-N-acetyl neuraminic acid (MU-NANA) (Sigma) at 25 µl/well (10 µM) and plates were read with a fluorometer.

Three B cell clones (FBC-39, FBD-56, and FBD-94) were found to have neutralization activity against both influenza B Victoria and Yamagata lineages. The VH and VL genes of these clones were sequenced, and cloned into IgG1 expression vectors. Recombinant antibodies were produced by transient transfection of mammalian cell lines derived from Human Embryonic Kidney (HEK) or Chinese Hamster Ovary (CHO) cells. Supernatants from transfected cells were collected after 7-10 days of culture, and antibodies (IgG) were affinity purified by Protein A chromatography, and dialyzed into Phosphate Buffered Saline (PBS).

An Ig BLAST algorithm was used to align the mAb sequences to a database of human antibody germline sequences. The closest germline templates were identified for each of the gene regions of the VH and VL (Table 6). Non-germlined amino acids were identified by aligning to these reference sequences.

TABLE 6

Identification of the closest human genes comprising the VH and VL

| | VH V gene | VH J gene | VH D gene | VL V gene | VL J gene |
|---|---|---|---|---|---|
| FBD-56 | IGHV3-9*01 | IGHJ6*02 | IGHD5-12*01 | IGKV3-11*01 | IGKJ5*01 |
| FBD-94 | IGHV3-9*01 | IGHJ6*02 | IGHD6-13*01 | IGKV3-11*01 | IGKJ5*01 |
| FBC-39 | IGHV3-15*01 | IGHJ6*02 | IGHD3-3*01 | IGKV1-12*01 | IGKJ2*01 |

FBC-39 Variant Construction:

In the FBC-39 antibody VL, there was only one non-germline framework residue: F at position 87 in the light chain, wherein the germlined amino acid is Y (or L87F(Y)), as numbered by Kabat (position 103 for IMGT numbering). The germlined sequence is referred to herein as FBC-39-L87Y. The non-germlined sequence is referred to as FBC-39-L87F.

In the FBC-39 antibody VH, there are 11 non-germlined Kabat defined framework residues: H6V(E), H27L(F), H28S(T), H30L(S), H68S(T), H77M(T), H79F(Y), H81H(Q), H82aS(N), H83R(K), and H93A(T), as numbered by Kabat. If using the IMGT definition of framework residues, there are 7 non-germlined residues: H6V(E), H77S(T), H86M(T), H88F(Y), H90H(Q), H92S(N), and H95R(K).

A variant was constructed in which all 12 of the non-germlined Kabat defined framework residues were reverted to the germline amino acid. This antibody construct demonstrated a significant reduction in the neutralizing activity and breadth of coverage for the Victoria lineage influenza B viruses, implying that one or more of the non-germline residue(s) are important for activity.

Three of the non-germlined framework residues, located at positions H27, H28, and H30, are in an area defined as the VH framework 1 by the Kabat system although they are considered part of the HCDR-1 by the IMGT system. Antibody variants were generated by reverting all non-germlined Kabat defined framework amino acids to their respective germline residues, except for these three positions: H27L(F), H28S(T), H30L(S), which were "wobbled" between germline residue and non-germline residue to generate seven heavy chain variants: FBC-39 LSL, FBC-39 FSL; FBC-39 LTL; FBC-39 FTL; FBC-39-FSS; FBC-39-LTS; FBC-39-FTS, in which the germline residues are underlined, such that FBC-39 FTS contains the three germlined amino acids, and FBC-39 LSL contains the three wildtype residues at positions H27, H28, and H30.

Additionally, the germline residue N at H82 (H92 IMGT) created a potential deamidation site (NS) in the VH. Consequently, this was substituted with the wildtype S of FBC-39 in all seven variants, FBC-39 LSL, FBC-39 FSL, FBC-39 LTL, FBC-39 FTL, FBC-39-FSS, FBC-39-LTS, and FBC-39-FTS. Additionally, all seven of the FBC-39 variants share the same light chain sequence (FBC-39-L87Y), which differs from the FBC-39 light chain by one amino acid.

The resulting antibody variants were expressed and purified as described above and further characterized.

Example 2. The Isolated Anti-HA Antibodies Bind to Both Influenza B HA Lineages An HA ELISA binding assay was performed to determine the binding and cross-reactivity of the isolated antibodies. A 384-well Maxisorb ELISA plate (Nunc) was coated overnight at 4° C. with 0.5 µg/ml of recombinant HA derived from a Yamagata lineage strain B/FLA/06, or a Victoria lineage strain B/BNE/08 in PBS. The plate was washed with PBS containing 0.1% v/v Tween-20 to remove uncoated protein, and blocking solution containing 1% (w/v) casein (Thermo Scientific) was added for 1 hour at room temperature. The blocking solution was discarded and a 3-fold serial dilution in PBS of each of the anti-HA antibodies (FBC-39, FBD-56, and FBD-94) was added and incubated for 1 hour at room temperature. The plate was washed three times and bound antibodies were detected using a peroxidase-conjugated mouse anti-human IgG antibody (Jackson). Antibody binding activity was calculated by either measuring the chemiluminescent signal after addition of Supersignal Pico substrate (Thermo Scientific) or by measuring the color change at 450 nm after incubation with Tetramethylbenzidine (TMB) one component substrate (available from Kirkegaard and Perry Laboratories, Inc. (KPL), Gaithersburg, Md.) followed by the addition of 2N sulfuric acid to stop the reaction.

TABLE 7

| | Binding to rHA by ELISA (Ave $EC_{50}$, ng/ml) | |
| --- | --- | --- |
| | B/FL/06 (yam) | B/BNE/08 (vic) |
| FBC-39 | 20 | 48 |
| FBD-56 | 24 | 30 |
| FBD-94 | 13 | 16 |

Table 7 shows the average $EC_{50}$ from three independent experiments. All three anti-HA IgGs (FBC-39, FBD-56 and FBD-94) bound recombinant HA from both influenza B lineages. Similar $EC_{50}$ values were observed with between all three antibodies against the Yamagata (B/FL/06) HA. A lower $EC_{50}$ was observed with the Victoria (B/BNE/08) for FBD-94 than for either FBD-56 or FBC-39.

The seven FBC-39 antibody germlined variants were tested for binding activity by ELISA. Table 8 shows the binding results of the unpurified anti-HA FBC-39 IgG variants, where the FBC-39 FTS contains the Kabat defined framework germlined amino acids, and the FBC-39 LSL contains the Kabat defined framework germined amino acids except wildtype residues at positions H27, H28, and H30 (Kabat numbering). These results show that all variants bound to the Yamagata lineage (B/FL/06) HA protein, but variants containing an S residue at position H30 lost binding affinity for the Victoria lineage (B/BNE/08) HA protein. Four of the variants, FBC-39 LSL, FSL, LTL, and FTL, showed equivalent or better binding affinity than FBC-39 to HA proteins from both lineages.

TABLE 8

| | Binding to rHA by ELISA ($EC_{50}$, ng/ml) | |
| --- | --- | --- |
| | B/FL/06 (yam) | B/BNE/08 (vic) |
| FBC-39 | 22 | 186 |
| FBC-39 LSL | 21 | 152 |
| FBC-39 FSL | 14 | 273 |
| FBC-39 LTL | 17 | 114 |
| FBC-39 FTL | 17 | 118 |
| FBC-39 FSS | 19 | >1000 |
| FBC-39 LTS | 13 | >1000 |
| FBC-39 FTS | 26 | >1000 |

Example 3. In Vitro Cross-Reactive Neutralizing Activity of Anti-Flu B HA IgGs Against Virus from Two Different Lineages A similar microneutralization assay was used as described in Example 1 to test for purified mAb activity. In brief, MDCK cells that were cultured in MEM medium (Invitrogen) supplemented with antibiotics, glutamine (complete MEM medium) and 10% (v/v) fetal bovine serum. 60 $TCID_{50}$ (50% tissue culture infectious doses) of virus was added to three-fold dilutions of antibody in a 384-well plate in complete MEM medium containing 0.75 ug/ml TPCK treated trypsin (Worthington) in duplicate wells, after 30 minutes incubation at room temperature, $2 \times 10^4$ cells/well were added to the plate. After incubation at 33° C. 5% $CO_2$ incubator for approximately 40 hours, the NA activity was measured by adding a fluorescently-labelled substrate, methylumbelliferyl-N-acetyl neuraminic acid (MU-NANA) (Sigma) to each well and incubated at 37° C. for 1 hr. Virus replication represented by NA activity was quantified by reading fluorescence using an Envision Fluorometer (PerkinElmer) using the following settings: excitation 355 nm, emission 460 nm; 10 flashes per well. The neutralization titer (50% inhibitory concentration [$IC_{50}$]) is expressed as the final antibody concentration that reduced the fluorescence signal by 50% compared to cell control wells. Influenza B virus strains used in Table 9 are as listed below: B/Lee/40 (B/Lee/40); B/AA/66 (ca B/Ann Arbor/1/66); B/HK/72 (B/Hong Kong/5/72); B/BJ/97 (ca B/Beijing/243/97 (victoria)), B/HK/01 (B/Hong Kong/330/2001 (victoria)); B/MY/04 (B/Malaysia/2506/2004 (victoria)); B/BNE/08 (ca B/Brisbane/60/2008 (victoria)); B/AA/94 (ca B/Ann Arbor/2/94 (yamagata)); B/YSI/98 (ca B/Yamanashi/166/98 (yamagata)); B/JHB/99 (ca B/Johannesburg/5/99 (yamagata)); B/SC/99 (B/Sichuan/379/99 (yamagata)); B/FL/06 (B/Florida/4/2006 (yamagata)).

TABLE 9

| | | Neutralization (Ave $IC_{50}$ ug/ml) | | | | | | |
| --- | --- | --- | --- | --- | --- | --- | --- | --- |
| lineage | virus strain | FBD-56 | FBD-94 | FBC39 | FBC-39 LSL | FBC-39 FSL | FBC-39 LTL | FBC-39 FTL |
| untyped | B/Lee/40 | 0.004 | 0.009 | 0.021 | 0.014 | 0.011 | 0.010 | 0.013 |
| | B/AA/66 | 0.035 | 0.014 | 0.061 | 0.027 | 0.034 | 0.023 | 0.026 |
| | B/HK/72 | 0.051 | 0.017 | 0.026 | 0.019 | 0.019 | 0.018 | 0.022 |

TABLE 9-continued

| lineage | virus strain | Neutralization (Ave IC$_{50}$ ug/ml) | | | | | | |
|---|---|---|---|---|---|---|---|---|
| | | FBD-56 | FBD-94 | FBC39 | FBC-39 LSL | FBC-39 FSL | FBC-39 LTL | FBC-39 FTL |
| Victoria lineage | B/BJ/97 | 0.016 | 0.005 | 0.218 | 0.182 | 0.195 | 0.152 | 0.134 |
| | B/HK/01 | 0.038 | 0.021 | 0.142 | 0.172 | 0.132 | 0.084 | 0.121 |
| | B/MY/04 | 0.058 | 0.023 | 0.079 | 0.094 | 0.076 | 0.076 | 0.074 |
| | B/BNE/08 | 0.010 | 0.006 | 0.238 | 0.100 | 0.080 | 0.151 | 0.098 |
| Yammagata lineage | B/AA/94 | 1.251 | 0.891 | 0.027 | 0.033 | 0.023 | 0.023 | 0.023 |
| | B/YSI/98 | 0.133 | 0.012 | 0.039 | 0.014 | 0.009 | 0.010 | 0.007 |
| | B/JHB/99 | 0.021 | 0.012 | 0.304 | nd | nd | nd | nd |
| | B/SC/99 | nd* | nd | 0.034 | 0.026 | 0.022 | 0.023 | 0.023 |
| | B/FL/06 | 0.013 | 0.016 | 0.046 | 0.016 | 0.017 | 0.023 | 0.014 |

*nd = not determined

Table 9 shows the average IC$_{50}$ from two independent experiments. The anti-HA antibodies neutralized all the influenza B viruses tested. FBD-56 and FBD-94 were more potent than the FBC-39, but showed some reduced activity against the B/AA/94 strain. The FBC-39 variants, LSL, FSL, LTL, and FTL neutralized all viruses to a similar or lower IC$_{50}$ than FBC-39.

Example 4. Binding and Neutralization of Influenza a H9 Virus Strains

HA binding ELISAs were performed with similar methodology as in Example 2, with the exception that the 384-well plates were coated for 2 hours at room temperature with 3 µg/ml of recombinant HA derived from influenza A subtype H9 (A/chicken/HK/G9/97(H9N2)) in PBS. The results showed that the FBC-39, and germlined variants LTL bound H9 HA with similar EC$_{50}$ values of 6.2 and 6.3 µg/ml respectively, and FBC-39 LSL and FTL bound with higher ECK of 41.7 and 46.1 µg/ml respectively (Table 10). In contrast the FBC-39 FSL bound only weakly at the highest dose tested 50 µg/ml, and no binding was seen with FBD-56 and FBD-94.

TABLE 10

| | Activity against influenza A/chicken/HK/G9/97(H9N2) | |
|---|---|---|
| | Binding EC$_{50}$ (µg/ml) | Neutralization IC$_{50}$ (µg/ml) |
| FBD-56 | nb* | >50 |
| FBD-94 | nb | >50 |
| FBC-39 | 6.2 | 0.17 |
| FBC-39 LSL | 41.7 | 0.59 |
| FBC-39 FSL | weak | 1.70 |
| FBC-39 LTL | 6.3 | 0.09 |
| FBC-39 FTL | 46.1 | 0.43 |
| Ctl mAb | nb | >50 |

*nb = no binding

To confirm the binding of the influenza A H9 HA protein was functionally relevant, a microneutralization assay was performed using similar methodology as described in Example 3. For this assay, cold-adapted (ca) live attenuated influenza vaccine virus was generated by reverse genetics, containing the viral HA and NA genes from the A/chicken/Hong Kong/G9/97 (H9N2) virus in the context of the six internal protein genes of the ca A/Ann Arbor/6/60 (H2N2) virus with similar methodology as described by Jin et al. (2003) Virology. 306:18-24). Results of the microneutralization assay are shown in Table 10. Consistent with binding profile, FBC-39 and the variants potentially neutralized the H9N2 virus with biologically relevant IC$_{50}$ values. FBC-39 and FBC-39 LTL had the most potent activity with IC$_{50}$ values of 0.17 and 0.09 µg/ml, respectively. As expected, the FBD-56, FBD-94, and the control antibodies showed no neutralization activity at the highest concentration tested (50 µg/ml).

Example 5. Epitope Identification by Selection of Monoclonal Antibody Resistant Mutants (MARMs)

Yamagata lineage influenza B virus (B/Florida/4/2006; B/FLA/06) and Victoria lineage influenza B virus (B/Malyasia/2506/2004; B/MY/04) were incubated with high concentrations of FBC-39, FBD-56, and FBD-94 (125×IC$_{50}$) for 1 hour before the mixture of virus and antibody was adsorbed to MDCK cells at 30,000 TCID50 per well in 10×96-well plates and cultured in the presence of FBC-39, FBD-56, and FBD-94 (10×IC$_{50}$). Putative MARMs exhibiting the cytopathic effect (CPE) on the infected cells up to 3 days after infection were isolated. The HA gene were amplified by RT-PCR and subsequently sequenced, and then the isolated virus was confirmed for resistance by microneutralization assay. No MARMS were isolated from B/FLA/09 virus when cultured in the presence of FBC-39, FBD-56, or FBD-94. When the Victoria lineage (B/MY/04) virus was used, MARMS were isolated in the presence of FBD-56 and FBD-94, but not in the presence of FBC-39. Sequence analysis revealed that two FBD-56 MARMs contained single amino acid substitution at position 128 from glutamic acid (E) to lysine (K) or valine (V) (Table 11). The FBD-94 MARM harboured a single amino acid substitution at position 128 from E to K (Table 11). A variant of the Yamagata lineage B/Florida/4/2006 containing a single amino acid substitution at position 141 from glycine (G) to E (B/FLA/06 G141E) conferred an 8-fold reduction in FBC-39 neutralization compared to the wildtype virus (B/FLA/06). Using this B/FLA/09 G141E variant and Yamagata lineage virus B/Jiangsu/10/2003 (B/JIN/03), a naturally circulating virus that contains an R at position 141 (G141R), MARM isolation was repeated with only the FBC-39 mAb. One MARM virus was isolated using the B/FLA/09 G141E virus with a single amino acid change from G to arginine (R) at position 235 (Table 11). Two B/JIN/03 escape mutant viruses were identified with single amino acid substitutions from serine (S) to isoleucine (I) at position 150, or from E to leucine (L) at position 235 (Table 11), respectively. The amino acid substitution identified in these influenza B MARMs are located in the head region of HA (Wang et al. (2008) J. Virol. 82(6):3011-20), suggesting that FBC-39, FBD-56, and FBD-94 recognize epitopes on the HA head of the influenza B virus, with FBD-56 and FBD-94 having a key contact at position 128 and sharing a overlapping epitope, and FBC-39 having a conformational epitope with important contact residues at positions 141, 150, and 235.

TABLE 11

Amino Acid Substitutions Identified Through MARM Selection

| | B/FLA/06 | B/MY/04 | B/FLA/06 G141E | B/JIN/03 |
|---|---|---|---|---|
| FBC-39 | *NF | NF | G235R | S150I or E235L |
| FBD-56 | NF | E128K or E128V | ^NA | NA |
| FBD-94 | NF | E128K | NA | NA |

*NF = No MARM Found
^NA = Not Assayed

Example 6. Influenza B Anti-HA Antibodies Exhibit Fc-Effector Function

Antibodies have the potential to clear virus infected cells through Fc-effector function such as antibody dependent cellular cytotoxicity (ADCC), antibody dependent cellular phagocytosis, and complement dependent killing. To confirm the anti-HA antibodies exhibited ADCC activity; we tested their ability to activate NK cells in the presence of influenza B virus with an ADCC bioassay. This assay uses a human NK cell line (NK92) that has been stably transfected with the human FcgIIIA high affinity receptor and a luciferase transgene under the control of the NFAT promoter, in order to measure Fc effector activation. 96-well plates were coated with $5.0\times10^4$ TCID50/well of B/Hong Kong/330/2001 (Victoria) virus stock. A serial dilution of FBD-94, FBC-39 as well as Fc-effector null variants that contain two substitutions in the Fc region, L234A and L235A (FBD-94 LALA and FBC-39 LALA) (Hezareh et al. (2001) J. Virol. 75(24):12161) were applied to the virus, and then NK cells were added at $5.0\times10^4$ cells/well and incubated at 37° C. for 4 hours. Luciferase was detected by the addition of Steady-Glo Reagent (Promega) and measured by envision plate reader. FIG. 1 shows that both FBD-94 and FBC-39 exhibit a dose dependent influenza B ADCC activity, whereas the LALA variants showed no activity at the same concentrations.

Example 7. In Vivo Prophylactic and Therapeutic Effect of Anti-Influenza B IgGs in an Lethal Murine Model of Influenza Infection The protective efficacy of influenza B neutralizing monoclonal antibodies was evaluated in a lethal influenza B murine model.

Prophylactic activity (FIG. 2 A-D): To test prophylactic efficacy, six-to-eight week old BALB/c (Harlan Laboratories) mice were administered a single intraperitoneal (IP) injection of either FBC-39 or FBD-94 antibody at doses of 3, 1, 0.3, or 0.1 mg/kg in 100 μl volumes in groups of eight. For each study, a group of control animals were treated IP with a human isotype non-relevant control IgG at 3 mg/kg in 100 μl volumes. Four hours after dosing, mice were inoculated intranasally with 15 times the fifty percent mouse lethal dose (15 $MLD_{50}$) of B/Sichuan/379/99 (Yamagata) (B/Sic/99) or 10 $MLD_{50}$ of the B/Hong Kong/330/2001 (Victoria) (B/HK/01) in a 50 μl volume. Mice were weighed on the day of virus challenge and monitored daily for weight loss and survival for 14 days (mice with body weight loss ≥25% were euthanized). Both FBC-39 and FBD-94 mAbs conferred protection in a dose-dependent manner. FBC-39 and FBD-94 at 0.3 mg/kg or greater provided 90%-100% protection to the animals challenged with B/Sic/99 (FIGS. 2 A and B) and B/HK/01 (FIGS. 2 C and D). FBC-39 and FBD94 at lower dose of 0.1 mg/kg were also highly protective against B/HK/01 with 90% and 80% survival rate, respectively. As expected, none of the mice that received the isotype control mAb at 3 or 30 mg/kg survived the challenge of B/Sic/99 or B/HK/01, respectively.

Therapeutic activity (FIG. 3 A-D and FIGS. 4 A and B): To assess the therapeutic efficacy of the antibodies, mice were inoculated with 10 $MLD_{50}$ of B/Sic/99 (Yamagata) or 5 $MLD_{50}$ of B/HK/01 (Victoria) and injected with 10, 3, 1, or 0.3 mg/kg of FBC-39 or FBD-94 two days post infection (pi). FBC-39 and FBD-94 provided complete protection to animals challenged with B/Sic/99 when administered at 1 mg/kg or greater (FIGS. 3 A and B). For the B/HK/01 infection, FBC-39 and FBD-94 at doses of 0.3 mg/kg and greater provided complete protection (FIGS. 3 C and D). As expected, the isotype control mAb given at 10 or 30 mg/kg failed to protect mice with a survival rate of 10% or 20% for B/Sic/99 and B/HK/01 infections, respectively.

To test the ability of the Flu B antibodies to protect over time, mice were inoculated with 5 $MLD_{50}$ of B/HK/01 and IP injected with 3 mg/kg of FBC-39 or FBD-94 initiated at 1, 2, 3, or 4 days pi. FBC-39 protected 100% of mice when administered on day 1 pi, and 80% and 70% on day 2 and 3 pi respectively (FIG. 4 A). FBD-94 protected 100% of mice when administered on day 1 and day 2 pi, and 80% and 60% on day 3 and day 4 pi, respectively (FIG. 4 B). As expected, mice treated with same dose of non-relevant isotype control antibody failed to protect mice with a survival rate of 10%.

Example 8. Hemaglutination Inhibition Activity

To determine a possible mechanism of action for the influenza B antibody functionality of the antibodies of the invention, hemagglutination inhibition (HAI) assays were performed using a diverse group of influenza B virus strains. The HAI assay detects antibodies that block the viral receptor engagement of the cellular surface expressed sialic acid by measuring the inhibition of virus-mediated agglutination of erythrocytes. Influenza B viruses (abbreviations as described below Table 12) were adjusted to 4 HA units determined by incubation with 0.05% turkey red blood cells (Lampire Biological Laboratories) in the absence of antibody. In a 96-well U-bottom plate FBD-94 and FBC-39 IgG was serially diluted in two-fold increments and diluted virus was added to the wells. After 30 to 60 min incubation, 50 ul of 0.05% turkey red blood cells was added. Plates were incubated an additional 30 to 60 minutes and observed for agglutination. The HAI titer was determined to be the minimum effective concentration (nM) of antibody that completely inhibited agglutination. Table 12 shows that FBD-94 and FBC39 had HAI activity against all influenza B strains tested, providing evidence of binding to the globular head of the influenza B HA. Other antibodies of the invention show similar activity using HAI assays.

TABLE 12

| Hemagglutination Inhibition Titer (nM) | | |
|---|---|---|
| Viral Strain | FBD-94 | FBC-39 |
| B/Lee/40 (un) | 1 | 5 |
| B/AA/66 (un) | 10 | 6 |

TABLE 12-continued

Hemagglutination Inhibition Titer (nM)

| Viral Strain | FBD-94 | FBC-39 |
|---|---|---|
| B/HK/72(Un) | 3 | 8 |
| B/BJ/97 (Vic) | 10 | 14 |
| B/HK/01(Vic) | 10 | 16 |
| B/Mal/04 (Vic) | 10 | 20 |
| B/OH/05 (Vic) | 10 | 24 |
| B/Bne/08 (Vic) | 4 | 20 |
| B/Yam/88 (Yam) | 250 | 11 |
| B/AA/94 (Yam) | 5 | 6 |
| B/Geo/98 (Yam) | 8 | 16 |
| B/Ysh/98 (Yam) | 10 | 13 |
| B/Joh/99 (Yam) | 10 | 18 |
| B/Sic/99 (Yam) | 5 | 10 |
| B/Vic/2000 (Yam) | 8 | 16 |
| B/Shg/02 (Yam) | 0 | 16 |
| B/Fla/4/06 (Yam) | 5 | 7 |

B/Lee/40 (B/Lee/40); B/AA/66 (ca B/Ann Arbor/1/66); B/HK/72 (B/Hong Kong/5/72); B/BJ/97 (ca B/Beijing/243/97 (victoria)), B/HK/01 (B/Hong Kong/330/2001 (victoria)); B/Mal/04 (B/Malaysia/2506/2004 (victoria)); B/OH/05 (B/Ohio/1/2005 (victoria)); B/BNE/08 (ca B/Brisbane/60/2008 (victoria)); B/Yam/88 (B/Yamagata/16/88 (yamagata)); B/AA/94 (ca B/Ann Arbor/2/94 (yamagata)); B/geo/98 (ca B/Georgia/02/98 (yamagata)); B/Ysh/98 (ca B/Yamanashi/166/98 (yamagata)); B/Joh/99 (ca B/Johannesburg/5/99 (yamagata)); B/Sic/99 (B/Sichuan/379/99 (yamagata)); B/Vic/00 (ca B/Victoria/504/2000 (yamagata)); B/Shg/02 (B/Shanghai/361/02 (yamagata)); and B/FL/06 (B/Florida/4/06 (yamagata)).

All publications, patents and patent applications mentioned in this specification are herein incorporated by reference into the specification to the same extent as if each individual publication, patent or patent application was specifically and individually indicated to be incorporated herein by reference.

```
Sequence Information

SEQ ID NO: 1 (FBD-56 VH DNA)
GAAGTGCAGCTGGTGGAGTCTGGGGGACACTTGGTGCAGCCTGGCAGG
TCCCTGAGACTCTCCTGTGCAGCCTCTGGATTCACCTTTGAGGATTATGC
CATGAATTGGGTCCGGCAAGCTCCAGGGAAGGGCCTGGAGTGGGTCTC
AGTCATTAGTTGGGACAGTGGTAGGATAGGCTATGCGGACTCTGTGAAG
GGCCGATTCACCATCTCCAGAGACAACGCCAAGAACTCCTCGTATCTGC
AAATGAACAGTCTGAGACCTGAGGACACTGCCTTGTATTATTGTGTAAGA
GATATGTTGGCTTATTATTCTGACAATAGTGGCAAAAAATACAACGTCTAC
GGTATGGACGTCTGGGGCCAAGGGACCACGGTCACCGTCTCCTCAG

SEQ ID NO: 2 (FBD-56 VH protein)
EVQLVESGGHLVQPGRSLRLSCAASGFTFEDYAMNWVRQAPGKGLEWVS
VISWDSGRIGYADSVKGRFTISRDNAKNSSYLQMNSLRPEDTALYYCVRDM
LAYYSDNSGKKYNVYGMDVWGQGTTVTVSS SEQ ID NO: 3 (FBD-56 HCDR-1-Kabat):
DYAMN SEQ ID NO: 4 (FBD-56 HCDR-2-Kabat):
VISWDSGRIGYADSVKG SEQ ID NO: 5 (FBD-56 HCDR-3-Kabat):
DMLAYYSDNSGKKYNVYGMDV SEQ ID NO: 6 (FBD-56 VL DNA)
GAAATTGTGTTGACACAGTCTCCAGCCACCCTGTCTTTGTCTCCAGGGG
AAAGAGCCACCCTCTCCTGCAGGGCCAGTCAGAGTGTTTCCACCTTCTT
AGCCTGGTACCAACAGAAACCTGGCCAGGCTCCCAGGCTCCTCATGTAT
GATGCATCCAACAGGGCCACTGGCATCCCAGCCAGGTTCAGTGGCAGT
GGGTCTGGGACAGACTTCACTCTCACCATCAGCAGCCTAGAACCTGAAG
ATTTTGCAATTTACTACTGTCAGCAGCGTAGCCACTGGCCTCCTATCTTC
GGCCAAGGGACACGACTGGAGATTAAAC SEQ ID NO: 7 (FBD-56 VL protein)
EIVLTQSPATLSLSPGERATLSCRASQSVSTFLAWYQQKPGQAPRLLMYDA
SNRATGIPARFSGSGSGTDFTLTISSLEPEDFAIYYCQQRSHWPPIFGQGTR
LEIK SEQ ID NO: 8 (FBD-56 LCDR-1-Kabat):
ASQSVSTFLA SEQ ID NO: 9 (FBD-56 LCDR-2-Kabat):
DASNRAT SEQ ID NO: 10 (FBD-56 LCDR-3-Kabat):
QQRSHWPPI SEQ ID NO: 11 (FBD-94 VH DNA)
GAAGTGCAGCTGGTGGAGTCTGGGGGAGGCTTGGTGCAACCTGGCAGG
TCCCTGAGACTCTCCTGTGCAGTTTCTGGATTCATCTTTGAAGATTATGC
CATAAACTGGGTCCGGCAAGCTCCAGGGAAGGGCCTGGAGTGGGTCTC
AATTATTAGTTGGGACAGTGGTAGGATAGGCTACGCGGACTCTGTGAGG
GGCCGATTCACCATCTCCAGAGACAACGCCAAGAACTCCTCGTTTCTGC
```

| Sequence Information |
|---|
| AAATGAACAGTCTGAGACCCGAAGACACGGCCGTGTATTATTGTGTAAAA<br>GATATGTTGGCGTATTATTATGATGGTAGCGGCATCAGGTACAACCTCTA<br>CGGTATGGACGTCTGGGGCCAAGGGACCACGGTCACCGTCTCCTCAG<br><br>SEQ ID NO: 12 (FBD-94 VH protein)<br>EVQLVESGGGLVQPGRSLRLSCAVSGFIFEDYAINWVRQAPGKGLEWVSIIS<br>WDSGRIGYADSVRGRFTISRDNAKNSSFLQMNSLRPEDTAVYYCVKDMLAY<br>YYDGSGIRYNLYGMDVWGQGTTVTVSS<br><br>SEQ ID NO: 13 (FBD-94 HCDR-1-Kabat):<br>DYAIN<br><br>SEQ ID NO: 14 (FBD-94 HCDR-2-Kabat):<br>IISWDSGRIGYADSVRG<br><br>SEQ ID NO: 15 (FBD-94 HCDR-3-Kabat):<br>DMLAYYYDGSGIRYNLYGMDV<br><br>SEQ ID NO: 16 (FBD-94 VL DNA)<br>GAAATTGTGTTGACACAGTCTCCAGCCACTCTGTCTTTGTCTCCAGGGGA<br>AAGAGCCACCCTCTCCTGCAGGGCCAGTCGGAGTATTACCACCTTCTTA<br>GCCTGGTACCAACAAAAACCTGGCAGGCTCCCAGGCTCCTCATCTACG<br>ATGCATCCAACAGGGCCACTGGCGTCCCAGCCAGGTTCAGTGGCAGTG<br>GGTCTGGGACAGACTTCACTCTCACCATCAACAGCCTAGAGCCTGACGA<br>TTTTGCAATTTATTACTGTCAGCAGCGTGACCACTGGCCTCCGATCTTCG<br>GCCAAGGGACACGACTGGAGATTAAAC<br><br>SEQ ID NO: 17 (FBD-94 VL protein)<br>EIVLTQSPATLSLSPGERATLSCRASRSITTFLAWYQQKPGQAPRLLIYDASN<br>RATGVPARFSGSGSGTDFTLTINSLEPDDFAIYYCQQRDHWPPIFGQGTRLE<br>IK<br><br>SEQ ID NO: 18 (FBD-94 LCDR-1-Kabat):<br>RASRSITTFLA<br><br>SEQ ID NO: 19 (FBD-94 LCDR-2-Kabat):<br>DASNRAT<br><br>SEQ ID NO: 20 (FBD-94 LCDR-3-Kabat):<br>QQRDHWPPI<br><br>SEQ ID NO: 21 (FBC-39 VH DNA)<br>GAGGTGCAGCTGGTGGTGTCTGGGGGAGGCTTGGTAAAGCCTGGGGG<br>GTCCCTTAGACTCTCCTGTGCAGCCTCTGGACTCAGTTTCCTTAACGCCT<br>GGATGAGCTGGGTCCGCCAGGCTCCAGGGAAGGGGCTGGAGTGGGTT<br>GGCCGTATTAAAAGTAATACTGATGGTGGGACAACAGACTACGCCGCAC<br>CCGTGAAAGGCAGATTCAGCATCTCAAGAGACGATTCAAAGAACATGCT<br>GTTTCTGCATATGAGCAGCCTGAGAACCGAGGACACAGCCGTCTATTAC<br>TGCGCCACAGATGGACCTTACTCTGACGATTTTAGAAGTGGTTATGCCG<br>CACGCTACCGTTATTTCGGAATGGACGTCTGGGGCCAAGGGACCACGG<br>TCACCGTCTCCTCAG<br><br>SEQ ID NO: 22 (FBC-39 VH protein)<br>EVQLVVSGGGLVKPGGSLRLSCAASGLSFLNAWMSWVRQAPGKGLEWVG<br>RIKSNTDGGTTDYAAPVKGRFSISRDDSKNMLFLHMSSLRTEDTAVYYCATD<br>GPYSDDFRSGYAARYRYFGMDVWGQGTTVTVSS<br><br>SEQ ID NO: 23 (FBC-39 HCDR-1-Kabat):<br>NAWMS<br><br>SEQ ID NO: 24 (FBC-39 HCDR-2-Kabat):<br>RIKSNTDGGTTDYAAPVKG<br><br>SEQ ID NO: 25 (FBC-39 HCDR-3-Kabat):<br>DGPYSDDFRSGYAARYRYFGMDV<br><br>SEQ ID NO: 26 (FBC-39 VL DNA)<br>GACATCCAGATGACCCAGTCTCCATCTTCCGTGTCTGCATCTGTGGGAG<br>ACAGAGTCACCATCACTTGTCGGGCGAGTCAGGATATTAGCACCTGGTT<br>AGCCTGGTATCAGCAGAAACCAGGGAAAGCCCCTAAGCTCCTGATCTAT<br>GCTGCATCCAGTTTGCAAAGTGGGGTCCCATCAAGATTCAGCGGCAGTG<br>GATCTGGGACAGATTTCACTCTCACCATCAGCAGCCTGCAGCCTGAAGA<br>TTTTGCAACTTACTTTTGTCAGCAGGCTAACAGTTTCCCTCCGACTTTTG<br>GCCAGGGGACCAAGCTGGAGATCAAAC |

Sequence Information

SEQ ID NO: 27 (FBC-39 VL protein)
DIQMTQSPSSVSASVGDRVTITCRASQDISTWLAWYQQKPGKAPKLLIYAAS
SLQSGVPSRFSGSGSGTDFTLTISSLQPEDFATYFCQQANSFPPTFGQGTK
LEIK SEQ ID NO: 28 (FBC-39 LCDR-1-Kabat):
RASQDISTWLA SEQ ID NO: 29 (FBC-39 LCDR-2-Kabat):
AASSLQS SEQ ID NO: 30 (FBC-39 LCDR-3-Kabat):
QQANSFPPT SEQ ID NO: 31 (FBC-39 LSL VH DNA)
GAGGTGCAGCTGGTGGAGTCTGGGGGAGGCTTGGTAAAGCCTGGGGG
GTCCCTTAGACTCTCCTGTGCAGCCTCTGGACTCTCTTTCCTTAACGCCT
GGATGAGCTGGGTCCGCCAGGCTCCAGGGAAGGGCCTGGAGTGGGTT
GGCCGTATTAAAAGTAATACTGATGGTGGGACAACAGACTACGCCGCAC
CCGTGAAAGGCAGATTCACCATCTCAAGAGACGATTCAAAGAACACGCT
GTATCTGCAAATGAGCAGCCTGAAAACCGAGGACACAGCCGTCTATTAC
TGCACCACAGATGGACCTTACTCTGACGATTTTAGAAGTGGTTATGCCGC
ACGCTACCGTTATTTCGGAATGGACGTCTGGGGCCAAGGGACCACGGT
CACCGTCTCCTCA SEQ ID NO: 32 (FBC-39 LSL VH protein)
EVQLVESGGGLVKPGGSLRLSCAASGLSFLNAWMSWVRQAPGKGLEWVG
RIKSNTDGGTTDYAAPVKGRFTISRDDSKNTLYLQMSSLKTEDTAVYYCTTD
GPYSDDFRSGYAARYRYFGMDVWGQGTTVTVSS SEQ ID NO: 33 (FBC-39 LSL HCDR-1-Kabat):
NAWMS SEQ ID NO: 34 (FBC-39 LSL HCDR-2-Kabat):

SEQ ID NO: 35 (FBC-39 LSL HCDR-3-Kabat):
DGPYSDDFRSGYAARYRYFGMDV

SEQ ID NO: 36 (FBC-39 LSL VL DNA)
GACATCCAGATGACCCAGTCTCCATCTTCCGTGTCTGCATCTGTGGGAG
ACAGAGTCACCATCACTTGTCGGGCGAGTCAGGATATTAGCACCTGGTT
AGCCTGGTATCAGCAGAAACCAGGGAAAGCCCCTAAGCTCCTGATCTAT
GCTGCATCCAGTTTGCAAAGTGGGGTCCCATCAAGATTCAGCGGCAGTG
GATCTGGGACAGATTTCACTCTCACCATCAGCAGCCTGCAGCCTGAAGA
TTTTGCAACTTACTATTGTCAGCAGGCTAACAGTTTCCCTCCGACTTTTG
GCCAGGGGACCAAGCTGGAGATCAAAC

SEQ ID NO: 37 (FBC-39 LSL VL protein)
DIQMTQSPSSVSASVGDRVTITCRASQDISTWLAWYQQKPGKAPKLLIYAAS
SLQSGVPSRFSGSGSGTDFTLTISSLQPEDFATYYCQQANSFPPTFGQGTK
LEIK SEQ ID NO: 38 (FBC-39 LSL LCDR-1-Kabat):
RASQDISTWLA SEQ ID NO: 39 (FBC-39 LSL LCDR-2-Kabat):
AASSLQS SEQ ID NO: 40 (FBC-39 LSL LCDR-3-Kabat):
QQANSFPPT SEQ ID NO: 41 (FBC-39 FSL VH DNA)
GAGGTGCAGCTGGTGGAGTCTGGGGGAGGCTTGGTAAAGCCTGGGGG
GTCCCTTAGACTCTCCTGTGCAGCCTCTGGATTCTCTTTCCTTAACGCCT
GGATGAGCTGGGTCCGCCAGGCTCCAGGGAAGGGCCTGGAGTGGGTT
GGCCGTATTAAAAGTAATACTGATGGTGGGACAACAGACTACGCCGCAC
CCGTGAAAGGCAGATTCACCATCTCAAGAGACGATTCAAAGAACACGCT
GTATCTGCAAATGAGCAGCCTGAAAACCGAGGACACAGCCGTCTATTAC
TGCACCACAGATGGACCTTACTCTGACGATTTTAGAAGTGGTTATGCCGC
ACGCTACCGTTATTTCGGAATGGACGTCTGGGGCCAAGGGACCACGGT
CACCGTCTCCTCA -continued Sequence Information SEQ ID NO: 42 (FBC-39 FSL VH protein)
EVQLVESGGGLVKPGGSLRLSCAASGFSFLNAWMSWVRQAPGKGLEWVG
RIKSNTDGGTTDYAAPVKGRFTISRDDSKNTLYLQMSSLKTEDTAVYYCTTD
GPYSDDFRSGYAARYRYFGMDVWGQGTTVTVSS SEQ ID NO: 43 (FBC-39 FSL HCDR-1-Kabat):
NAWMS SEQ ID NO: 44 (FBC-39 FSL HCDR-2-Kabat):
RIKSNTDGGTTDYAAPVKG SEQ ID NO: 45 (FBC-39 FSL HCDR-3-Kabat):
DGPYSDDFRSGYAARYRYFGMDV SEQ ID NO: 46 (FBC-39 FSL VL DNA)
GACATCCAGATGACCCAGTCTCCATCTTCCGTGTCTGCATCTGTGGGAG
ACAGAGTCACCATCACTTGTCGGGCGAGTCAGGATATTAGCACCTGGTT
AGCCTGGTATCAGCAGAAACCAGGGAAAGCCCCTAAGCTCCTGATCTAT
GCTGCATCCAGTTTGCAAAGTGGGGTCCCATCAAGATTCAGCGGCAGTG
GATCTGGGACAGATTTCACTCTCACCATCAGCAGCCTGCAGCCTGAAGA
TTTTGCAACTTACTATTGTCAGCAGGCTAACAGTTTCCCTCCGACTTTTG
GCCAGGGGACCAAGCTGGAGATCAAAC SEQ ID NO: 47 (FBC-39 FSL VL protein)
DIQMTQSPSSVSASVGDRVTITCRASQDISTWLAWYQQKPGKAPKLLIYAAS
SLQSGVPSRFSGSGSGTDFTLTISSLQPEDFATYYCQQANSFPPTFGQGTK
LEIK SEQ ID NO: 48 (FBC-39 FSL LCDR-1-Kabat):
RASQDISTWLA SEQ ID NO: 49 (FBC-39 FSL LCDR-2-Kabat):
AASSLQS SEQ ID NO: 50 (FBC-39 FSL LCDR-3-Kabat):
QQANSFPPT SEQ ID NO: 51 (FBC-39 LTL VH DNA)
GAGGTGCAGCTGGTGGAGTCTGGGGGAGGCTTGGTAAAGCCTGGGGG
GTCCCTTAGACTCTCCTGTGCAGCCTCTGGACTCACTTTCCTTAACGCCT
GGATGAGCTGGGTCCGCCAGGCTCCAGGGAAGGGCCTGGAGTGGGTT
GGCCGTATTAAAAGTAATACTGATGGTGGGACAACAGACTACGCCGCAC
CCGTGAAAGGCAGATTCACCATCTCAAGAGACGATTCAAAGAACACGCT
GTATCTGCAAATGAGCAGCCTGAAAACCGAGGACACAGCCGTCTATTAC
TGCACCACAGATGGACCTTACTCTGACGATTTTAGAAGTGGTTATGCCGC
ACGCTACCGTTATTTCGGAATGGACGTCTGGGGCCAAGGGACCACGGT
CACCGTCTCCTCA SEQ ID NO: 52 (FBC-39 LTL VH protein)
EVQLVESGGGLVKPGGSLRLSCAASGLTFLNAWMSWVRQAPGKGLEWVG
RIKSNTDGGTTDYAAPVKGRFTISRDDSKNTLYLQMSSLKTEDTAVYYCTTD
GPYSDDFRSGYAARYRYFGMDVWGQGTTVTVSS SEQ ID NO: 53 (FBC-39 LTL HCDR-1-Kabat):
NAWMS SEQ ID NO: 54 (FBC-39 LTL HCDR-2-Kabat):
RIKSNTDGGTTDYAAPVKG SEQ ID NO: 55 (FBC-39 LTL HCDR-3-Kabat):
DGPYSDDFRSGYAARYRYFGMDV SEQ ID NO: 56 (FBC-39 LTL VL DNA)
GACATCCAGATGACCCAGTCTCCATCTTCCGTGTCTGCATCTGTGGGAG
ACAGAGTCACCATCACTTGTCGGGCGAGTCAGGATATTAGCACCTGGTT
AGCCTGGTATCAGCAGAAACCAGGGAAAGCCCCTAAGCTCCTGATCTAT
GCTGCATCCAGTTTGCAAAGTGGGGTCCCATCAAGATTCAGCGGCAGTG
GATCTGGGACAGATTTCACTCTCACCATCAGCAGCCTGCAGCCTGAAGA
TTTTGCAACTTACTATTGTCAGCAGGCTAACAGTTTCCCTCCGACTTTTG
GCCAGGGGACCAAGCTGGAGATCAAAC SEQ ID NO: 57 (FBC-39 LTL VL protein)
DIQMTQSPSSVSASVGDRVTITCRASQDISTWLAWYQQKPGKAPKLLIYAAS
SLQSGVPSRFSGSGSGTDFTLTISSLQPEDFATYYCQQANSFPPTFGQGTK
LEIK

| Sequence Information |
|---|
| SEQ ID NO: 58 (FBC-39 LTL LCDR-1-Kabat):<br>RASQDISTWLA<br><br>SEQ ID NO: 59 (FBC-39 LTL LCDR-2-Kabat):<br>AASSLQS<br><br>SEQ ID NO: 60 (FBC-39 LTL LCDR-3-Kabat):<br>QQANSFPPT<br><br>SEQ ID NO: 61 (FBC-39 FTL VH DNA)<br>GAGGTGCAGCTGGTGGAGTCTGGGGGAGGCTTGGTAAAGCCTGGGGG<br>GTCCCTTAGACTCTCCTGTGCAGCCTCTGGATTCACTTTCCTTAACGCCT<br>GGATGAGCTGGGTCCGCCAGGCTCCAGGGAAGGGCCTGGAGTGGGTT<br>GGCCGTATTAAAAGTAATACTGATGGTGGGACAACAGACTACGCCGCAC<br>CCGTGAAAGGCAGATTCACCATCTCAAGAGACGATTCAAAGAACACGCT<br>GTATCTGCAAATGAGCAGCCTGAAAACCGAGGACACAGCCGTCTATTAC<br>TGCACCACAGATGGACCTTACTCTGACGATTTTAGAAGTGGTTATGCCGC<br>ACGCTACCGTTATTTCGGAATGGACGTCTGGGGCCAAGGGACCACGGT<br>CACCGTCTCCTCA<br><br>SEQ ID NO: 62 (FBC-39 FTL VH protein)<br>EVQLVESGGGLVKPGGSLRLSCAASGFTFLNAWMSWVRQAPGKGLEWVG<br>RIKSNTDGGTTDYAAPVKGRFTISRDDSKNTLYLQMSSLKTEDTAVYYCTTD<br>GPYSDDFRSGYAARYRYFGMDVWGQGTTVTVSS<br><br>SEQ ID NO: 63 (FBC-39 FTL HCDR-1-Kabat):<br>NAWMS<br><br>SEQ ID NO: 64 (FBC-39 FTL HCDR-2-Kabat):<br>RIKSNTDGGTTDYAAPVKG<br><br>SEQ ID NO: 65 (FBC-39 FTL HCDR-3-Kabat):<br>DGPYSDDFRSGYAARYRYFGMDV<br><br>SEQ ID NO: 66 (FBC-39 FTL VL DNA)<br>GACATCCAGATGACCCAGTCTCCATCTTCCGTGTCTGCATCTGTGGGAG<br>ACAGAGTCACCATCACTTGTCGGGCGAGTCAGGATATTAGCACCTGGTT<br>AGCCTGGTATCAGCAGAAACCAGGGAAAGCCCCTAAGCTCCTGATCTAT<br>GCTGCATCCAGTTTGCAAAGTGGGGTCCCATCAAGATTCAGCGGCAGTG<br>GATCTGGGACAGATTTCACTCTCACCATCAGCAGCCTGCAGCCTGAAGA<br>TTTTGCAACTTACTATTGTCAGCAGGCTAACAGTTTCCCTCCGACTTTTG<br>GCCAGGGGACCAAGCTGGAGATCAAAC<br><br>SEQ ID NO: 67 (FBC-39 FTL VL protein)<br>DIQMTQSPSSVSASVGDRVTITCRASQDISTWLAWYQQKPGKAPKLLIYAAS<br>SLQSGVPSRFSGSGSGTDFTLTISSLQPEDFATYYCQQANSFPPTFGQGTK<br>LEIK<br><br>SEQ ID NO: 68 (FBC-39 FTL LCDR-1-Kabat):<br>RASQDISTWLA<br><br>SEQ ID NO: 69 (FBC-39 FTL LCDR-2-Kabat):<br>AASSLQS<br><br>SEQ ID NO: 70 (FBC-39 FTL LCDR-3-Kabat):<br>QQANSFPPT<br><br>SEQ ID NO: 71 (FBC-39 VH protein-with variable amino acids)<br>(See FIG. 6)<br><br>SEQ ID NO: 72 (FBC-39 VL protein-with variable amino acids)<br>(See FIG. 7)<br><br>SEQ ID NO: 73 (FBC-39 FSS VH DNA)<br>GAGGTGCAGCTGGTGGAGTCTGGGGGAGGCTTGGTAAAGCCTGGGGG<br>GTCCCTTAGACTCTCCTGTGCAGCCTCTGGATTCTCTTTCAGTAACGCCT<br>GGATGAGCTGGGTCCGCCAGGCTCCAGGGAAGGGCCTGGAGTGGGTT<br>GGCCGTATTAAAAGTAATACTGATGGTGGGACAACAGACTACGCCGCAC<br>CCGTGAAAGGCAGATTCACCATCTCAAGAGACGATTCAAAGAACACGCT<br>GTATCTGCAAATGAGCAGCCTGAAAACCGAGGACACAGCCGTCTATTAC<br>TGCACCACAGATGGACCTTACTCTGACGATTTTAGAAGTGGTTATGCCGC<br>ACGCTACCGTTATTTCGGAATGGACGTCTGGGGCCAAGGGACCACGGT<br>CACCGTCTCCTCA |

-continued

Sequence Information

SEQ ID NO: 74 (FBC-39 FSS VH protein)
EVQLVESGGGLVKPGGSLRLSCAASGFSFSNAWMSWVRQAPGKGLEWVG
RIKSNTDGGTTDYAAPVKGRFTISRDDSKNTLYLQMSSLKTEDTAVYYCTTD
GPYSDDFRSGYAARYRYFGMDVWGQGTTVTVSS SEQ ID NO: 75 (FBC-39 FSS HCDR-1-Kabat):
RASQDISTWLA SEQ ID NO: 76 (FBC-39 FSS HCDR-2-Kabat):
RIKSNTDGGTTDYAAPVKG SEQ ID NO: 77 (FBC-39 FSS HCDR-3-Kabat):
DGPYSDDFRSGYAARYRYFGMDV

SEQ ID NO: 78 (FBC-39 FSS HCDR-1-IMGT):
GFSFSNAW

SEQ ID NO: 79 (FBC-39 FSS HCDR-2-IMGT):

IKSNTDGGTT
SEQ ID NO: 80 (FBC-39 FSS HCDR-3-IMGT):
TTDGPYSDDFRSGYAARYRYFGMDV

SEQ ID NO: 81 (FBC-39 FSS VL DNA)
GACATCCAGATGACCCAGTCTCCATCTTCCGTGTCTGCATCTGTGGGAG
ACAGAGTCACCATCACTTGTCGGGCGAGTCAGGATATTAGCACCTGGTT
AGCCTGGTATCAGCAGAAACCAGGGAAAGCCCCTAAGCTCCTGATCTAT
GCTGCATCCAGTTTGCAAAGTGGGGTCCCATCAAGATTCAGCGGCAGTG
GATCTGGGACAGATTTCACTCTCACCATCAGCAGCCTGCAGCCTGAAGA
TTTTGCAACTTACTATTGTCAGCAGGCTAACAGTTTCCCTCCGACTTTTG
GCCAGGGGACCAAGCTGGAGATCAAAC

SEQ ID NO: 82 (FBC-39 FSS VL protein)
DIQMTQSPSSVSASVGDRVTITCRASQDISTWLAWYQQKPGKAPKLLIYAAS
SLQSGVPSRFSGSGSGTDFTLTISSLQPEDFATYYCQQANSFPPTFGQGTK
LEIK SEQ ID NO: 83 (FBC-39 FSS LCDR-1-Kabat):
RASQDISTWLA SEQ ID NO: 84 (FBC-39 FSS LCDR-2-Kabat):
AASSLQS SEQ ID NO: 85 (FBC-39 FSS LCDR-3-Kabat):
QQANSFPPT

SEQ ID NO: 86 (FBC-39 FSS LCDR-1-IMGT):
QDISTW

SEQ ID NO: 87 (FBC-39 FSS LCDR-2-IMGT):
AAS

SEQ ID NO: 88 (FBC-39 FSS LCDR-3-IMGT):
QQANSFPPT

SEQ ID NO: 89 (FBC-39 LTS VH DNA):
GAGGTGCAGCTGGTGGAGTCTGGGGGAGGCTTGGTAAAGCCTGGGGG
GTCCCTTAGACTCTCCTGTGCAGCCTCTGGACTCACTTTCAGTAACGCCT
GGATGAGCTGGGTCCGCCAGGCTCCAGGGAAGGGCCTGGAGTGGGTT
GGCCGTATTAAAAGTAATACTGATGGTGGGACAACAGACTACGCCGCAC
CCGTGAAAGGCAGATTCACCATCTCAAGAGACGATTCAAAGAACACGCT
GTATCTGCAAATGAGCAGCCTGAAAACCGAGGACACAGCCGTCTATTAC
TGCACCACAGATGGACCTTACTCTGACGATTTTAGAAGTGGTTATGCCGC
ACGCTACCGTTATTTCGGAATGGACGTCTGGGGCCAAGGGACCACGGT
CACCGTCTCCTCA

SEQ ID NO: 90 (FBC-39 LTS VH protein):
EVQLVESGGGLVKPGGSLRLSCAASGLTFSNAWMSWVRQAPGKGLEWVG
RIKSNTDGGTTDYAAPVKGRFTISRDDSKNTLYLQMSSLKTEDTAVYYCTTD
GPYSDDFRSGYAARYRYFGMDVWGQGTTVTVSS SEQ ID NO: 91 (FBC-39 LTS HCDR-1-Kabat):
RASQDISTWLA SEQ ID NO: 92 (FBC-39 LTS HCDR-2-Kabat):
RIKSNTDGGTTDYAAPVKG SEQ ID NO: 93 (FBC-39 LTS HCDR-3-Kabat):
DGPYSDDFRSGYAARYRYFGMDV

SEQ ID NO: 94 (FBC-39 LTS HCDR-1-IMGT):
GLTFSNAW

SEQ ID NO: 95 (FBC-39 LTS HCDR-2-IMGT):
IKSNTDGGTT

SEQ ID NO: 96 (FBC-39 LTS HCDR-3-IMGT):
TTDGPYSDDFRSGYAARYRYFGMDV

SEQ ID NO: 97 (FBC-39 LTS VL DNA)
GACATCCAGATGACCCAGTCTCCATCTTCCGTGTCTGCATCTGTGGGAG
ACAGAGTCACCATCACTTGTCGGGCGAGTCAGGATATTAGCACCTGGTT
AGCCTGGTATCAGCAGAAACCAGGGAAAGCCCCTAAGCTCCTGATCTAT
GCTGCATCCAGTTTGCAAAGTGGGGTCCCATCAAGATTCAGCGGCAGTG
GATCTGGGACAGATTTCACTCTCACCATCAGCAGCCTGCAGCCTGAAGA
TTTTGCAACTTACTATTGTCAGCAGGCTAACAGTTTCCCTCCGACTTTTG
GCCAGGGGACCAAGCTGGAGATCAAAC

SEQ ID NO: 98 (FBC-39 LTS VL protein)
DIQMTQSPSSVSASVGDRVTITCRASQDISTWLAWYQQKPGKAPKLLIYAAS
SLQSGVPSRFSGSGSGTDFTLTISSLQPEDFATYYCQQANSFPPTFGQGTK
LEIK SEQ ID NO: 99 (FBC-39 LTS LCDR-1-Kabat):
RASQDISTWLA SEQ ID NO: 100 (FBC-39 LTS LCDR-2-Kabat):
AASSLQS SEQ ID NO: 101 (FBC-39 LTS LCDR-3-Kabat):
QQANSFPPT

SEQ ID NO: 102 (FBC-39 LTS LCDR-1-IMGT):
QDISTW

SEQ ID NO: 103 (FBC-39 LTS LCDR-2-IMGT):
AAS

SEQ ID NO: 104 (FBC-39 LTS LCDR-3-IMGT):
QQANSFPPT

SEQ ID NO: 105 (FBC-39 FTS VH DNA):
GAGGTGCAGCTGGTGGAGTCTGGGGGAGGCTTGGTAAAGCCTGGGGG
GTCCCTTAGACTCTCCTGTGCAGCCTCTGGATTCACTTTCAGTAACGCCT
GGATGAGCTGGGTCCGCCAGGCTCCAGGGAAGGGCCTGGAGTGGGTT
GGCCGTATTAAAAGTAATACTGATGGTGGGACAACAGACTACGCCGCAC
CCGTGAAAGGCAGATTCACCATCTCAAGAGACGATTCAAAGAACACGCT
GTATCTGCAAATGAGCAGCCTGAAAACCGAGGACACAGCCGTCTATTAC
TGCACCACAGATGGACCTTACTCTGACGATTTTAGAAGTGGTTATGCCGC
ACGCTACCGTTATTTCGGAATGGACGTCTGGGGCCAAGGGACCACGGT
CACCGTCTCCTCA

SEQ ID NO: 106 (FBC-39 FTS VH protein):
EVQLVESGGGLVKPGGSLRLSCAASGFTFSNAWMSWVRQAPGKGLEWVG
RIKSNTDGGTTDYAAPVKGRFTISRDDSKNTLYLQMSSLKTEDTAVYYCTTD
GPYSDDFRSGYAARYRYFGMDVWGQGTTVTVSS SEQ ID NO: 107 (FBC-39 FTS HCDR-1-Kabat):
RASQDISTWLA SEQ ID NO: 108 (FBC-39 FTS HCDR-2-Kabat):
RIKSNTDGGTTDYAAPVKG SEQ ID NO: 109 (FBC-39 FTS HCDR-3-Kabat):
DGPYSDDFRSGYAARYRYFGMDV

SEQ ID NO: 110 (FBC-39 FTS HCDR-1-IMGT):
GFTFSNAW

SEQ ID NO: 111 (FBC-39 FTS HCDR-2 IMGT):
IKSNTDGGTT

-continued

Sequence Information

SEQ ID NO: 112 (FBC-39 FTS HCDR-3-IMGT):
TDGPYSDDFRSGYAARYRYFGMDV

SEQ ID NO: 113 (FBC-39 FTS VL DNA)
GACATCCAGATGACCCAGTCTCCATCTTCCGTGTCTGCATCTGTGGGAG
ACAGAGTCACCATCACTTGTCGGGCGAGTCAGGATATTAGCACCTGGTT
AGCCTGGTATCAGCAGAAACCAGGGAAAGCCCCTAAGCTCCTGATCTAT
GCTGCATCCAGTTTGCAAAGTGGGGTCCCATCAAGATTCAGCGGCAGTG
GATCTGGGACAGATTTCACTCTCACCATCAGCAGCCTGCAGCCTGAAGA
TTTTGCAACTTACTATTGTCAGCAGGCTAACAGTTTCCCTCCGACTTTTG
GCCAGGGGACCAAGCTGGAGATCAAAC

SEQ ID NO: 114 (FBC-39 FTS VL protein)
DIQMTQSPSSVSASVGDRVTITCRASQDISTWLAWYQQKPGKAPKLLIYAAS
SLQSGVPSRFSGSGSGTDFTLTISSLQPEDFATYYCQQANSFPPTFGQGTK
LEIK SEQ ID NO: 115 (FBC-39 FTS LCDR-1-Kabat):
RASQDISTWLA SEQ ID NO: 116 (FBC-39 FTS LCDR-2-Kabat):
AASSLQS SEQ ID NO: 117 (FBC-39 FTS LCDR-3-Kabat):
QQANSFPPT

SEQ ID NO: 118 (FBC-39 FTS LCDR-1-IMGT)
QDISTW

SEQ ID NO: 119 (FBC-39 FTS LCDR-2-IMGT):
AAS

SEQ ID NO: 120 (FBC-39 FTS LCDR-3-IMGT):
QQANSFPPT

SEQ ID NO: 121 (FBC-39 HCDR-1-IMGT):
GLSFLNAW

SEQ ID NO: 122 (FBC-39 HCDR-2-IMGT):
IKSNTDGGTT

SEQ ID NO: 123 (FBC-39 HCDR-3-IMGT):
TDGPYSDDFRSGYAARYRYFGMDVW

SEQ ID NO: 124 (FBC-39 LCDR-1-IMGT):
QDISTW

SEQ ID NO: 125 (FBC-39 LCDR-2-IMGT):
AAS

SEQ ID NO: 126 (FBC-39 LCDR-3-IMGT):
QQANSFPPT

SEQ ID NO: 127 (FBC-39 LSL HCDR-1-IMGT):
GLSFLNAW

SEQ ID NO: 128 (FBC-39 LSL HCDR-2-IMGT):
IKSNTDGGTT

SEQ ID NO: 129 (FBC-39 LSL HCDR-3-IMGT):
TTDGPYSDDFRSGYAARYRYFGMDV

SEQ ID NO: 130 (FBC-39 LSL LCDR-1-IMGT):
QDISTW

SEQ ID NO: 131 (FBC-39 LSL LCDR-2-IMGT):
AAS

SEQ ID NO: 132 (FBC-39 LSL LCDR-3-IMGT):
QQANSFPPT

SEQ ID NO: 133 (FBC-39 FSL HCDR-1-IMGT):
GFSFLNAW

SEQ ID NO: 134 (FBC-39 FSL HCDR-2-IMGT):
IKSNTDGGTT

Sequence Information

SEQ ID NO: 135 (FBC-39 LSL HCDR-3-IMGT):
TTDGPYSDDFRSGYAARYRYFGMDV

SEQ ID NO: 136 (FBC-39 FSL LCDR-1-IMGT):
QDISTW

SEQ ID NO: 137 (FBC-39 FSL LCDR-2-IMGT):
AAS

SEQ ID NO: 138 (FBC-39 FSL LCDR-3-IMGT):
QQANSFPPT

SEQ ID NO: 139 (FBC-39 LTL HCDR-1-IMGT):
GLTFLNAW

SEQ ID NO: 140 (FBC-39 LTL HCDR-2-IMGT):
IKSNTDGGTT

SEQ ID NO: 141 (FBC-39 LTL HCDR-3-IMGT):
TTDGPYSDDFRSGYAARYRYFGMDV

SEQ ID NO: 142 (FBC-39 LTL LCDR-1-IMGT):
QDISTW

SEQ ID NO: 143 (FBC-39 LTL LCDR-2-IMGT):
AAS

SEQ ID NO: 144 (FBC-39 LTL LCDR-3-IMGT):
QQANSFPPT

SEQ ID NO: 145 (FBC-39 FTL HCDR-1-IMGT):
GFTFLNAW

SEQ ID NO: 146 (FBC-39 FTL HCDR-2-IMGT):
IKSNTDGGTT

SEQ ID NO: 147 (FBC-39 FTL HCDR-3-IMGT):
TTDGPYSDDFRSGYAARYRYFGMDV

SEQ ID NO: 148 (FBC-39 FTL LCDR-1-IMGT):
QDISTW

SEQ ID NO: 149 (FBC-39 FTL LCDR-2-IMGT):
AAS

SEQ ID NO: 150 (FBC-39 FTL LCDR-3-IMGT):
QQANSFPPT

The invention claimed is:

1. An isolated antibody or an antigen binding fragment thereof comprising a variant Fc region, wherein the antibody or antigen binding fragment thereof is capable of binding to influenza B virus hemagglutinin (HA) and neutralizing influenza B virus in two phylogenetically distinct lineages, and wherein the antibody or antigen binding fragment thereof includes a set of six CDRs: HCDR-1, HCDR-2, HCDR-3, LCDR-1, LCDR-2, LCDR-3, in which the set of six CDRs is selected from:

(a) HCDR-1 of SEQ ID NO.: 3, HCDR-2 of SEQ ID NO.: 4, HCDR-3 of SEQ ID NO.: 5, LCDR-1 of SEQ ID NO.: 8, LCDR-2 of SEQ ID NO.: 9 and LCDR-3 of SEQ ID NO.: 10;

(b) HCDR-1 of SEQ ID NO.: 13, HCDR-2 of SEQ ID NO.: 14, HCDR-3 of SEQ ID NO.: 15, LCDR-1 of SEQ ID NO.: 18, LCDR-2 of SEQ ID NO.: 19, LCDR-3 of SEQ ID NO.: 20;

(c) HCDR-1 of SEQ ID NO.: 23, HCDR-2 of SEQ ID NO.: 24, HCDR-3 of SEQ ID NO.: 25, LCDR-1 of SEQ ID NO.: 28, LCDR-2 of SEQ ID NO.: 29 and LCDR-3 of SEQ ID NO.: 30;

(d) HCDR-1 of SEQ ID NO.: 33, HCDR-2 of SEQ ID NO.: 34, HCDR-3 of SEQ ID NO.: 35, LCDR-1 of SEQ ID NO.: 38, LCDR-2 of SEQ ID NO.: 39 and LCDR-3 of SEQ ID NO.: 40;

(e) HCDR-1 of SEQ ID NO.: 43, HCDR-2 of SEQ ID NO.: 44, HCDR-3 of SEQ ID NO.: 45, LCDR-1 of SEQ ID NO.: 48, LCDR-2 of SEQ ID NO.: 49 and LCDR-3 of SEQ ID NO.: 50;

(f) HCDR-1 of SEQ ID NO.: 53, HCDR-2 of SEQ ID NO.: 54, HCDR-3 of SEQ ID NO.: 55, LCDR-1 of

SEQ ID NO.: 58, LCDR-2 of SEQ ID NO.: 59 and LCDR-3 of SEQ ID NO.: 60;

(g) HCDR-1 of SEQ ID NO.: 63, HCDR-2 of SEQ ID NO.: 64, HCDR-3 of SEQ ID NO.: 65, LCDR-1 of SEQ ID NO.: 68, LCDR-2 of SEQ ID NO.: 69 and LCDR-3 of SEQ ID NO.: 70;

(h) HCDR-1 of SEQ ID NO.: 75, HCDR-2 of SEQ ID NO.: 76, HCDR-3 of SEQ ID NO.: 77, LCDR-1 of SEQ ID NO.: 83, LCDR-2 of SEQ ID NO.: 84 and LCDR-3 of SEQ ID NO.: 85;

(i) HCDR-1 of SEQ ID NO.: 91, HCDR-2 of SEQ ID NO.: 92, HCDR-3 of SEQ ID NO.: 93, LCDR-1 of SEQ ID NO.: 99, LCDR-2 of SEQ ID NO.: 100 and LCDR-3 of SEQ ID NO.: 101;

(j) HCDR-1 of SEQ ID NO.: 107, HCDR-2 of SEQ ID NO.: 108, HCDR-3 of SEQ ID NO.: 109, LCDR-1 of SEQ ID NO.: 115, LCDR-2 of SEQ ID NO.: 116 and LCDR-3 of SEQ ID NO.: 117;

(k) HCDR-1 of SEQ ID NO.: 127, HCDR-2 of SEQ ID NO.: 128, HCDR-3 of SEQ ID NO.: 129, LCDR-1 of SEQ ID NO.: 130, LCDR-2 of SEQ ID NO.: 131 and LCDR-3 of SEQ ID NO.: 132;

(l) HCDR-1 of SEQ ID NO.: 133, HCDR-2 of SEQ ID NO.: 134, HCDR-3 of SEQ ID NO.: 135, LCDR-1 of SEQ ID NO.: 136, LCDR-2 of SEQ ID NO.: 137 and LCDR-3 of SEQ ID NO.: 138;

(m) HCDR-1 of SEQ ID NO.: 139, HCDR-2 of SEQ ID NO.: 140, HCDR-3 of SEQ ID NO.: 141, LCDR-1 of SEQ ID NO.: 142, LCDR-2 of SEQ ID NO.: 143 and LCDR-3 of SEQ ID NO.: 144;

(n) HCDR-1 of SEQ ID NO.: 78, HCDR-2 of SEQ ID NO.: 79, HCDR-3 of SEQ ID NO.: 80, LCDR-1 of SEQ ID NO.: 86, LCDR-2 of SEQ ID NO.: 87 and LCDR-3 of SEQ ID NO.: 88;

(o) HCDR-1 of SEQ ID NO.: 94, HCDR-2 of SEQ ID NO.: 95, HCDR-3 of SEQ ID NO.: 96, LCDR-1 of SEQ ID NO.: 102, LCDR-2 of SEQ ID NO.: 103 and LCDR-3 of SEQ ID NO.: 104; and (p) HCDR-1 of SEQ ID NO.: 110, HCDR-2 of SEQ ID NO.: 111, HCDR-3 of SEQ ID NO.: 112, LCDR-1 of SEQ ID NO.: 118, LCDR-2 of SEQ ID NO.: 119 and LCDR-3 of SEQ ID NO.: 120.

2. The isolated antibody or antigen binding fragment thereof according to claim 1, wherein the antibody or antigen binding fragment thereof is capable of binding to Yamagata lineage influenza B virus selected from: B/AA/94 (ca B/Ann Arbor/2/94 (yamagata)); B/YSI/98 (ca B/Yamanashi/166/98 (yamagata)); B/JHB/99 (ca B/Johannesburg/5/99 (yamagata)); B/SC/99 (B/Sichuan/379/99 (yamagata)); B/FL/06 (B/Florida/4/2006 (yamagata)); Victoria lineage influenza B virus selected from: B/BJ/97 (ca B/Beijing/243/97 (victoria)), B/HK/01 (B/Hong Kong/330/2001 (victoria)); B/MY/04 (B/Malaysia/2506/2004 (victoria)); B/BNE/08 (ca B/Brisbane/60/2008 (victoria)); pre-divergent influenza B strains selected from: B/Lee/40 (B/Lee/40); B/AA/66 (ca B/Ann Arbor/1/66); B/HK/72 (B/Hong Kong/5/72); and combinations thereof.

3. The isolated antibody or antigen binding fragment thereof according to claim 1, wherein the antibody is capable of binding to influenza A virus hemagglutinin.

4. The isolated antibody or antigen binding fragment thereof according to claim 3, wherein the antibody is capable of binding to influenza A virus subtype 1 or subtype 2 hemagglutinin.

5. The isolated antibody or antigen binding fragment thereof according to claim 4, wherein the antibody is capable of binding to influenza A virus group 1 subtype selected from: H8, H9, H11, H12, H13, H16 and variants thereof.

6. The isolated antibody or antigen binding fragment thereof according claim 1 comprising a VH having at least 75% identity and/or a VL having at least 75% identity to a VH and/or VL selected from:

(a) VH of SEQ ID NO.: 2 and VL of SEQ ID NO.: 7,
(b) VH of SEQ ID NO.: 12 and VL of SEQ ID NO.: 17,
(c) VH of SEQ ID NO.: 32 and VL of SEQ ID NO.: 37,
(d) VH of SEQ ID NO.: 42 and VL of SEQ ID NO.: 47,
(e) VH of SEQ ID NO.: 52 and VL of SEQ ID NO.: 57,
(f) VH of SEQ ID NO.: 74 and VL of SEQ ID NO.: 82,
(g) VH of SEQ ID NO.: 90 and VL of SEQ ID NO.: 98, and
(h) VH of SEQ ID NO.: 106 and VL of SEQ ID NO.: 114.

7. The isolated antibody or antigen binding fragment thereof according to claim 1 comprising a VH and a VL selected from:

(a) VH of SEQ ID NO.: 2 and VL of SEQ ID NO.: 7,
b) VH of SEQ ID NO.: 12 and VL of SEQ ID NO.: 17,
(c) VH of SEQ ID NO.: 32 and VL of SEQ ID NO.: 37,
(d) VH of SEQ ID NO.: 42 and VL of SEQ ID NO.: 47,
(e) VH of SEQ ID NO.: 52 and VL of SEQ ID NO.: 57,
(f) VH of SEQ ID NO.: 74 and VL of SEQ ID NO.: 82,
(g) VH of SEQ ID NO.: 90 and VL of SEQ ID NO.: 98, and
(h) VH of SEQ ID NO.: 106 and VL of SEQ ID NO.: 114.

8. An isolated nucleic acid encoding an antibody or antigen binding fragment thereof according to claim 1.

9. A vector comprising an isolated nucleic acid according to claim 8.

10. A host cell comprising a nucleic acid according to claim 9.

11. A method for manufacturing an antibody or antigen binding fragment thereof that is capable of binding to influenza B virus hemagglutinin (HA) and neutralizing influenza B virus in two phylogenetically distinct lineages, the method comprising culturing a host cell comprising a nucleic acid according to claim 8 under conditions suitable for expression of the antibody or fragment thereof.

12. A composition comprising an antibody or antigen binding fragment thereof according to claim 1 and 25 mM His and 0.15M NaCl at pH 6.0.

13. A method for prophylaxis or treatment of influenza B infection in a subject comprising administering an effective amount of an antibody or antigen binding fragment thereof according to claim 1 to the subject.

14. A method for prophylaxis or treatment of influenza A and influenza B infection in a subject comprising administering an effective amount of an antibody or antigen binding fragment thereof according to claim 1 to the subject.

15. The use of an antibody or fragment thereof according to claim 1 for in vitro diagnosis of influenza B infection in a subject.

16. The isolated antibody or antigen binding fragment thereof according to claim 1, wherein the isolated antibody or antigen binding fragment thereof has an enhanced serum half-life relative to a native Fc antibody.

17. The isolated antibody or antigen binding fragment thereof according to claim 16, wherein the variant Fc region comprises a modification at one or more positions selected from 221, 225, 228, 234, 235, 236, 237, 238, 239, 240, 241, 243, 244, 245, 247, 250, 251, 252, 254, 255, 256, 257, 262, 263, 264, 265, 266, 267, 268, 269, 279, 280, 284, 292, 296, 297, 298, 299, 305, 308, 313, 316, 318, 320, 322, 325, 326, 327, 328, 329, 330, 331, 332, 333, 334, 339, 341, 343, 370, 373, 378, 392, 416, 419, 421, 428, 433, 434, 435, 436, 440, and 443 as numbered by the EU index as set forth in Kabat.

18. The isolated antibody or antigen binding fragment thereof according to claim 17, wherein the modification is selected from a substitution, insertion and a deletion.

19. The isolated antibody or antigen binding fragment thereof according to claim 16, wherein the variant Fc region includes at least one substitution selected from 221K, 221Y, 225E, 225K, 225W, 228P, 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241L, 241Y, 241E, 241R, 243W, 243L 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F, 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 434W, 434Y, 436H, 440Y and 443W as numbered by the EU index as set forth in Kabat.

20. The isolated antibody or antigen binding fragment thereof according to claim 16, wherein the variant Fc region comprises:
(a) at least one modification at one or more positions selected from 228, 234, 235 and 331 as numbered by the EU index as set forth in Kabat;
(b) at least one modification at one or more positions selected from 228 and 235 as numbered by the EU index as set forth in Kabat;
(c) at least one modification at one or more positions selected from 239, 330 and 332 as numbered by the EU index as set forth in Kabat; or
(d) at least one modification at one or more positions selected from 252, 254, and 256 as numbered by the EU index as set forth in Kabat.

21. The isolated antibody or antigen binding fragment thereof according to claim 16, wherein the variant Fc region comprises:
(a) one or more substitutions selected from 228P, 235E and 235Y as numbered by the EU index as set forth in Kabat;
(b) one or more substitutions selected from 239D, 330L, 330Y, and 332E as numbered by the EU index as set forth in Kabat;
(c) one or more substitutions selected from 252Y, 254T and 256E as numbered by the EU index as set forth in Kabat; or
(d) one or more substitutions selected from 228P, 234F, 235E, 235F, 235Y, and 331S as numbered by the EU index as set forth in Kabat.

22. The isolated antibody or antigen binding fragment thereof according to claim 16, wherein the variant Fc region comprises an IgG4 Fc region.

23. The isolated antibody or antigen binding fragment thereof according to claim 16, wherein the variant Fc region comprises three substitutions: 252Y, 254T and 256E as numbered by the EU index as set forth in Kabat.

24. The isolated antibody or antigen binding fragment thereof according to claim 1, wherein the set of six CDRs is: HCDR-1 of SEQ ID NO.: 53, HCDR-2 of SEQ ID NO.: 54, HCDR-3 of SEQ ID NO.: 55, LCDR-1 of SEQ ID NO.: 58, LCDR-2 of SEQ ID NO.: 59 and LCDR-3 of SEQ ID NO.: 60.

25. The isolated antibody or antigen binding fragment thereof according to claim 1, wherein the set of six CDRs is: HCDR-1 of SEQ ID NO.: 139, HCDR-2 of SEQ ID NO.: 140, HCDR-3 of SEQ ID NO.: 141, LCDR-1 of SEQ ID NO.: 142, LCDR-2 of SEQ ID NO.: 143 and LCDR-3 of SEQ ID NO.: 144.

26. The isolated antibody or antigen binding fragment thereof according to claim 1, comprising a VH of SEQ ID NO.: 52 and a VL of SEQ ID NO.: 57.

* * * * *

SEQUENCE LISTING

<160> NUMBER OF SEQ ID NOS: 158

<210> SEQ ID NO 1
<211> LENGTH: 391
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gaagtgcagc tggtggagtc tgggggacac ttggtgcagc ctggcaggtc cctgagactc      60
tcctgtgcag cctctggatt cacctttgag gattatgcca tgaattgggt ccggcaagct     120
ccagggaagg gcctggagtg gtctcagtc attagttggg acagtggtag gataggctat     180
gcggactctg tgaagggccg attcaccatc tccagagaca acgccaagaa ctcctcgtat     240
ctgcaaatga acagtctgag acctgaggac actgccttgt attattgtgt aagagatatg     300
```

```
ttggcttatt attctgacaa tagtggcaaa aaatacaacg tctacggtat ggacgtctgg    360
ggccaaggga ccacggtcac cgtctcctca g                                  391
```

<210> SEQ ID NO 2
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Glu Val Gln Leu Val Glu Ser Gly Gly His Leu Val Gln Pro Gly Arg
1               5                   10                  15

Ser Leu Arg Leu Ser Cys Ala Ala Ser Gly Phe Thr Phe Glu Asp Tyr
            20                  25                  30

Ala Met Asn Trp Val Arg Gln Ala Pro Gly Lys Gly Leu Glu Trp Val
        35                  40                  45

Ser Val Ile Ser Trp Asp Ser Gly Arg Ile Gly Tyr Ala Asp Ser Val
    50                  55                  60

Lys Gly Arg Phe Thr Ile Ser Arg Asp Asn Ala Lys Asn Ser Ser Tyr
65                  70                  75                  80

Leu Gln Met Asn Ser Leu Arg Pro Glu Asp Thr Ala Leu Tyr Tyr Cys
                85                  90                  95

Val Arg Asp Met Leu Ala Tyr Tyr Ser Asp Asn Ser Gly Lys Lys Tyr
            100                 105                 110

Asn Val Tyr Gly Met Asp Val Trp Gly Gln Gly Thr Thr Val Thr Val
        115                 120                 125

Ser Ser
    130
```

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Asp Tyr Ala Met Asn
1               5
```

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Val Ile Ser Trp Asp Ser Gly Arg Ile Gly Tyr Ala Asp Ser Val Lys
1               5                   10                  15

Gly
```

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Asp Met Leu Ala Tyr Tyr Ser Asp Asn Ser Gly Lys Lys Tyr Asn Val
1               5                   10                  15

Tyr Gly Met Asp Val
            20

<210> SEQ ID NO 6
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaaattgtgt tgacacagtc tccagccacc ctgtctttgt ctccagggga aagagccacc      60
ctctcctgca gggccagtca gagtgtttcc accttcttag cctggtacca acagaaacct    120
ggccaggctc ccaggctcct catgtatgat gcatccaaca gggccactgg catcccagcc    180
aggttcagtg gcagtgggtc tgggacagac ttcactctca ccatcagcag cctagaacct    240
gaagattttg caatttacta ctgtcagcag cgtagccact ggcctcctat cttcggccaa    300
gggacacgac tggagattaa ac                                             322

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Phe
            20                  25                  30

Leu Ala Trp Tyr Gln Gln Lys Pro Gly Gln Ala Pro Arg Leu Leu Met
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Arg Ser His Trp Pro Pro
                85                  90                  95

Ile Phe Gly Gln Gly Thr Arg Leu Glu Ile Lys
            100                 105

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ser Gln Ser Val Ser Thr Phe Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ala Ser Asn Arg Ala Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Arg Ser His Trp Pro Pro Ile
1               5

<210> SEQ ID NO 11
<211> LENGTH: 391
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaagtgcagc tggtggagtc tgggggaggc ttggtgcaac ctggcaggtc cctgagactc      60
tcctgtgcag tttctggatt catctttgaa gattatgcca taaactgggt ccggcaagct     120
ccagggaagg gcctggagtg gtctcaatt attagttggg acagtggtag gataggctac      180
gcggactctg tgaggggccg attcaccatc tccagagaca acgccaagaa ctcctcgttt     240
ctgcaaatga acagtctgag acccgaagac acggccgtgt attattgtgt aaaagatatg     300
ttggcgtatt attatgatgg tagcggcatc aggtacaacc tctacggtat ggacgtctgg     360
ggccaaggga ccacggtcac cgtctcctca g                                    391

<210> SEQ ID NO 12
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Val Ser Gly Phe Ile Phe Glu Asp Tyr
            20                  25                  30

Ala Ile Asn Trp Val Arg Gln Ala Pro Gly Lys Gly Leu Glu Trp Val
        35                  40                  45

Ser Ile Ile Ser Trp Asp Ser Gly Arg Ile Gly Tyr Ala Asp Ser Val
    50                  55                  60

Arg Gly Arg Phe Thr Ile Ser Arg Asp Asn Ala Lys Asn Ser Ser Phe
65                  70                  75                  80

```
Leu Gln Met Asn Ser Leu Arg Pro Glu Asp Thr Ala Val Tyr Tyr Cys
                 85                  90                  95

Val Lys Asp Met Leu Ala Tyr Tyr Tyr Asp Gly Ser Gly Ile Arg Tyr
            100                 105                 110

Asn Leu Tyr Gly Met Asp Val Trp Gly Gln Gly Thr Thr Val Thr Val
        115                 120                 125

Ser Ser
    130

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Tyr Ala Ile Asn
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Ile Ser Trp Asp Ser Gly Arg Ile Gly Tyr Ala Asp Ser Val Arg
1               5                   10                  15

Gly

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Met Leu Ala Tyr Tyr Tyr Asp Gly Ser Gly Ile Arg Tyr Asn Leu
1               5                   10                  15

Tyr Gly Met Asp Val
            20

<210> SEQ ID NO 16
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gaaattgtgt tgacacagtc tccagccact ctgtctttgt ctccagggga aagagccacc    60
ctctcctgca gggccagtcg agtattacc  accttcttag cctggtacca acaaaaacct   120
ggccaggctc ccaggctcct catctacgat gcatccaaca gggccactgg cgtcccagcc   180
aggttcagtg gcagtgggtc tgggacagac ttcactctca ccatcaacag cctagagcct   240
gacgattttg caattttatta ctgtcagcag cgtgaccact ggcctccgat cttcggccaa   300
```
gggacacgac tggagattaa ac                                            322

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Arg Ser Ile Thr Thr Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Val Pro Ala Arg Phe Ser Gly
    50                  55                  60

Ser Gly Ser Gly Thr Asp Phe Thr Leu Thr Ile Asn Ser Leu Glu Pro
65                  70                  75                  80

Asp Asp Phe Ala Ile Tyr Tyr Cys Gln Gln Arg Asp His Trp Pro Pro
                85                  90                  95

Ile Phe Gly Gln Gly Thr Arg Leu Glu Ile Lys
            100                 105

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Arg Ser Ile Thr Thr Phe Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Ala Ser Asn Arg Ala Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Arg Asp His Trp Pro Pro Ile
1               5

<210> SEQ ID NO 21

-continued

<210> SEQ ID NO 21
<211> LENGTH: 403
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gaggtgcagc tggtggtgtc tggggggaggc ttggtaaagc ctggggggtc ccttagactc     60
tcctgtgcag cctctggact cagtttcctt aacgcctgga tgagctgggt ccgccaggct    120
ccagggaagg ggctggagtg ggttggccgt attaaaagta atactgatgg tgggacaaca    180
gactacgccg cacccgtgaa aggcagattc agcatctcaa gagacgattc aaagaacatg    240
ctgtttctgc atatgagcag cctgagaacc gaggacacag ccgtctatta ctgcgccaca    300
gatggacctt actctgacga ttttagaagt ggttatgccg cacgctaccg ttatttcgga    360
atggacgtct ggggccaagg gaccacggtc accgtctcct cag                      403

<210> SEQ ID NO 22
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Val Ser Gly Gly Gly Leu Val Lys Pro Gly Gly
1               5                   10                  15

Ser Leu Arg Leu Ser Cys Ala Ala Ser Gly Leu Ser Phe Leu Asn Ala
            20                  25                  30

Trp Met Ser Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Ser Ile Ser Arg Asp Asp Ser Lys Asn Met
65                  70                  75                  80

Leu Phe Leu His Met Ser Ser Leu Arg Thr Glu Asp Thr Ala Val Tyr
                85                  90                  95

Tyr Cys Ala Thr Asp Gly Pro Tyr Ser Asp Asp Phe Arg Ser Gly Tyr
            100                 105                 110

Ala Ala Arg Tyr Arg Tyr Phe Gly Met Asp Val Trp Gly Gln Gly Thr
        115                 120                 125

Thr Val Thr Val Ser Ser
    130

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Ala Trp Met Ser
1               5

<210> SEQ ID NO 24
<211> LENGTH: 19
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 24

Arg Ile Lys Ser Asn Thr Asp Gly Gly Thr Thr Asp Tyr Ala Ala Pro
1               5                   10                  15

Val Lys Gly

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Gly Pro Tyr Ser Asp Asp Phe Arg Ser Gly Tyr Ala Ala Arg Tyr
1               5                   10                  15

Arg Tyr Phe Gly Met Asp Val
            20

<210> SEQ ID NO 26
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gacatccaga tgacccagtc tccatcttcc gtgtctgcat ctgtgggaga cagagtcacc      60
atcacttgtc gggcgagtca ggatattagc acctggttag cctggtatca gcagaaacca     120
gggaaagccc ctaagctcct gatctatgct gcatccagtt tgcaaagtgg ggtcccatca     180
agattcagcg gcagtggatc tgggacagat ttcactctca ccatcagcag cctgcagcct     240
gaagattttg caacttactt ttgtcagcag gctaacagtt tccctccgac ttttggccag     300
gggaccaagc tggagatcaa ac                                              322

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Pro

```
                85                  90                  95

Thr Phe Gly Gln Gly Thr Lys Leu Glu Ile Lys
            100                 105

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ala Ser Gln Asp Ile Ser Thr Trp Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Ser Ser Leu Gln Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Ala Asn Ser Phe Pro Pro Thr
1               5

<210> SEQ ID NO 31
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaggtgcagc tggtggagtc tgggggaggc ttggtaaagc ctggggggtc ccttagactc      60
tcctgtgcag cctctggact ctctttcctt aacgcctgga tgagctgggt ccgccaggct     120
ccagggaagg gcctggagtg ggttggccgt attaaaagta atactgatgg tgggacaaca     180
gactacgccg cacccgtgaa aggcagattc accatctcaa gagacgattc aaagaacacg     240
ctgtatctgc aaatgagcag cctgaaaacc gaggacacag ccgtctatta ctgcaccaca     300
gatggacctt actctgacga tttagaagt ggttatgccg cacgctaccg ttatttcgga     360
atggacgtct ggggccaagg gaccacggtc accgtctcct ca                        402

<210> SEQ ID NO 32
<211> LENGTH: 134
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Leu Ser Phe Leu Asn Ala
            20                  25                  30

Trp Met Ser Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Ser Ser Leu Lys Thr Glu Asp Thr Ala Val Tyr
                85                  90                  95

Tyr Cys Thr Thr Asp Gly Pro Tyr Ser Asp Asp Phe Arg Ser Gly Tyr
            100                 105                 110

Ala Ala Arg Tyr Arg Tyr Phe Gly Met Asp Val Trp Gly Gln Gly Thr
        115                 120                 125

Thr Val Thr Val Ser Ser
    130

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Ala Trp Met Ser
1               5

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ile Lys Ser Asn Thr Asp Gly Gly Thr Thr Asp Tyr Ala Ala Pro
1               5                   10                  15

Val Lys Gly

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Gly Pro Tyr Ser Asp Asp Phe Arg Ser Gly Tyr Ala Ala Arg Tyr
1               5                   10                  15

Arg Tyr Phe Gly Met Asp Val
            20

<210> SEQ ID NO 36
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gacatccaga tgacccagtc tccatcttcc gtgtctgcat ctgtgggaga cagagtcacc    60
atcacttgtc gggcgagtca ggatattagc acctggttag cctggtatca gcagaaacca   120
gggaaagccc ctaagctcct gatctatgct gcatccagtt tgcaaagtgg ggtcccatca   180
agattcagcg gcagtggatc tgggacagat ttcactctca ccatcagcag cctgcagcct   240
gaagattttg caacttacta ttgtcagcag gctaacagtt tccctccgac ttttggccag   300
gggaccaagc tggagatcaa ac                                            322
```

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105
```

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Arg Ala Ser Gln Asp Ile Ser Thr Trp Leu Ala
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ala Ser Ser Leu Gln Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Ala Asn Ser Phe Pro Pro Thr
1               5

<210> SEQ ID NO 41
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaggtgcagc tggtggagtc tgggggaggc ttggtaaagc ctggggggtc ccttagactc      60
tcctgtgcag cctctggatt ctctttcctt aacgcctgga tgagctgggt ccgccaggct     120
ccagggaagg gcctggagtg ggttggccgt attaaaagta atactgatgg tgggacaaca     180
gactacgccg cacccgtgaa aggcagattc accatctcaa gagacgattc aaagaacacg     240
ctgtatctgc aaatgagcag cctgaaaacc gaggacacac ccgtctatta ctgcaccaca     300
gatggacctt actctgacga tttttagaagt ggttatgccg cacgctaccg ttatttcgga     360
atggacgtct ggggccaagg gaccacggtc accgtctcct ca                        402

<210> SEQ ID NO 42
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Leu Asn Ala
            20                  25                  30

Trp Met Ser Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Ser Ser Leu Lys Thr Glu Asp Thr Ala Val Tyr
                85                  90                  95

Tyr Cys Thr Thr Asp Gly Pro Tyr Ser Asp Asp Phe Arg Ser Gly Tyr
            100                 105                 110

Ala Ala Arg Tyr Arg Tyr Phe Gly Met Asp Val Trp Gly Gln Gly Thr
        115                 120                 125

Thr Val Thr Val Ser Ser
        130

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn Ala Trp Met Ser
1               5

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ile Lys Ser Asn Thr Asp Gly Gly Thr Thr Asp Tyr Ala Ala Pro
1               5                   10                  15

Val Lys Gly

<210> SEQ ID NO 45
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Gly Pro Tyr Ser Asp Asp Phe Arg Ser Gly Tyr Ala Ala Arg Tyr
1               5                   10                  15

Arg Tyr Phe Gly Met Asp Val
            20

<210> SEQ ID NO 46
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gacatccaga tgacccagtc tccatcttcc gtgtctgcat ctgtgggaga cagagtcacc      60
atcacttgtc gggcgagtca ggatattagc acctggttag cctggtatca gcagaaacca     120
gggaaagccc ctaagctcct gatctatgct gcatccagtt tgcaaagtgg ggtcccatca     180
agattcagcg gcagtggatc tgggacagat tcactctca ccatcagcag cctgcagcct      240
gaagattttg caacttacta ttgtcagcag gctaacagtt tccctccgac ttttggccag     300
gggaccaagc tggagatcaa ac                                              322

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Gln Asp Ile Ser Thr Trp Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ala Ser Ser Leu Gln Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Ala Asn Ser Phe Pro Pro Thr
1               5

<210> SEQ ID NO 51
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaggtgcagc tggtggagtc tgggggaggc ttggtaaagc ctggggggtc ccttagactc    60

```
tcctgtgcag cctctggact cactttcctt aacgcctgga tgagctgggt ccgccaggct    120
ccagggaagg gcctggagtg ggttggccgt attaaaagta atactgatgg tgggacaaca    180
gactacgccg cacccgtgaa aggcagattc accatctcaa gagacgattc aaagaacacg    240
ctgtatctgc aaatgagcag cctgaaaacc gaggacacag ccgtctatta ctgcaccaca    300
gatggacctt actctgacga ttttagaagt ggttatgccg cacgctaccg ttatttcgga    360
atggacgtct ggggccaagg gaccacggtc accgtctcct ca                       402
```

```
<210> SEQ ID NO 52
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Leu Thr Phe Leu Asn Ala
            20                  25                  30

Trp Met Ser Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Ser Ser Leu Lys Thr Glu Asp Thr Ala Val Tyr
                85                  90                  95

Tyr Cys Thr Thr Asp Gly Pro Tyr Ser Asp Asp Phe Arg Ser Gly Tyr
            100                 105                 110

Ala Ala Arg Tyr Arg Tyr Phe Gly Met Asp Val Trp Gly Gln Gly Thr
        115                 120                 125

Thr Val Thr Val Ser Ser
    130

```
<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

Asn Ala Trp Met Ser
1               5

```
<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

Arg Ile Lys Ser Asn Thr Asp Gly Gly Thr Thr Asp Tyr Ala Ala Pro
1               5                   10                  15

Val Lys Gly

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Gly Pro Tyr Ser Asp Asp Phe Arg Ser Gly Tyr Ala Ala Arg Tyr
1               5                   10                  15

Arg Tyr Phe Gly Met Asp Val
            20

<210> SEQ ID NO 56
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gacatccaga tgacccagtc tccatcttcc gtgtctgcat ctgtgggaga cagagtcacc    60
atcacttgtc gggcgagtca ggatattagc acctggttag cctggtatca gcagaaacca   120
gggaaagccc ctaagctcct gatctatgct gcatccagtt tgcaaagtgg ggtcccatca   180
agattcagcg gcagtggatc tgggacagat ttcactctca ccatcagcag cctgcagcct   240
gaagattttg caacttacta ttgtcagcag gctaacagtt tccctccgac ttttggccag   300
gggaccaagc tggagatcaa ac                                            322

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105

<210> SEQ ID NO 58
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 58

Arg Ala Ser Gln Asp Ile Ser Thr Trp Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Ala Ser Ser Leu Gln Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gln Ala Asn Ser Phe Pro Pro Thr
1               5

<210> SEQ ID NO 61
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gaggtgcagc tggtggagtc tgggggaggc ttggtaaagc ctggggggtc ccttagactc    60
tcctgtgcag cctctggatt cactttcctt aacgcctgga tgagctgggt ccgccaggct   120
ccagggaagg gcctggagtg ggttggccgt attaaaagta atactgatgg tgggacaaca   180
gactacgccg cacccgtgaa aggcagattc accatctcaa gagacgattc aaagaacacg   240
ctgtatctgc aaatgagcag cctgaaaacc gaggacacag ccgtctatta ctgcaccaca   300
gatggacctt actctgacga ttttagaagt ggttatgccg cacgctaccg ttatttcgga   360
atggacgtct ggggccaagg gaccacggtc accgtctcct ca                      402
```

<210> SEQ ID NO 62
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Leu Asn Ala
            20                  25                  30

Trp Met Ser Trp Val Arg Gln Ala Pro Gly Lys Gly Leu Glu Trp Val 35                  40                  45
Gly Arg Ile Lys Ser Asn Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Ser Ser Leu Lys Thr Glu Asp Thr Ala Val Tyr
                85                  90                  95

Tyr Cys Thr Thr Asp Gly Pro Tyr Ser Asp Asp Phe Arg Ser Gly Tyr
            100                 105                 110

Ala Ala Arg Tyr Arg Tyr Phe Gly Met Asp Val Trp Gly Gln Gly Thr
        115                 120                 125

Thr Val Thr Val Ser Ser
    130

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Ala Trp Met Ser
1               5

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ile Lys Ser Asn Thr Asp Gly Gly Thr Thr Asp Tyr Ala Ala Pro
1               5                   10                  15

Val Lys Gly

<210> SEQ ID NO 65
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Gly Pro Tyr Ser Asp Asp Phe Arg Ser Gly Tyr Ala Ala Arg Tyr
1               5                   10                  15

Arg Tyr Phe Gly Met Asp Val
            20

<210> SEQ ID NO 66
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gacatccaga tgacccagtc tccatcttcc gtgtctgcat ctgtgggaga cagagtcacc      60

```
atcacttgtc gggcgagtca ggatattagc acctggttag cctggtatca gcagaaacca    120
gggaaagccc ctaagctcct gatctatgct gcatccagtt tgcaaagtgg ggtcccatca    180
agattcagcg gcagtggatc tgggacagat ttcactctca ccatcagcag cctgcagcct    240
gaagattttg caacttacta ttgtcagcag gctaacagtt tccctccgac ttttggccag    300
gggaccaagc tggagatcaa ac                                              322
```

```
<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ala Ser Gln Asp Ile Ser Thr Trp Leu Ala
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ala Ser Ser Leu Gln Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 70

Gln Gln Ala Asn Ser Phe Pro Pro Thr
1               5

<210> SEQ ID NO 71
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Val or Glu
<220> FEATURE:
<221> NAME/KEY: MOD_RES
<222> LOCATION: (27)..(27)
<223> OTHER INFORMATION: Leu or Phe
<220> FEATURE:
<221> NAME/KEY: MOD_RES
<222> LOCATION: (28)..(28)
<223> OTHER INFORMATION: Thr or Ser
<220> FEATURE:
<221> NAME/KEY: MOD_RES
<222> LOCATION: (30)..(30)
<223> OTHER INFORMATION: Ser or Leu
<220> FEATURE:
<221> NAME/KEY: MOD_RES
<222> LOCATION: (71)..(71)
<223> OTHER INFORMATION: Thr or Ser
<220> FEATURE:
<221> NAME/KEY: MOD_RES
<222> LOCATION: (80)..(80)
<223> OTHER INFORMATION: Thr or Met
<220> FEATURE:
<221> NAME/KEY: MOD_RES
<222> LOCATION: (82)..(82)
<223> OTHER INFORMATION: Tyr or Phe
<220> FEATURE:
<221> NAME/KEY: MOD_RES
<222> LOCATION: (84)..(84)
<223> OTHER INFORMATION: Gln or His
<220> FEATURE:
<221> NAME/KEY: MOD_RES
<222> LOCATION: (86)..(86)
<223> OTHER INFORMATION: Asn or Ser
<220> FEATURE:
<221> NAME/KEY: MOD_RES
<222> LOCATION: (89)..(89)
<223> OTHER INFORMATION: Lys or Arg
<220> FEATURE:
<221> NAME/KEY: MOD_RES
<222> LOCATION: (99)..(99)
<223> OTHER INFORMATION: Thr or Ala

<400> SEQUENCE: 71

Glu Val Gln Leu Val Xaa Ser Gly Gly Gly Leu Val Lys Pro Gly Gly
1               5                   10                  15

Ser Leu Arg Leu Ser Cys Ala Ala Ser Gly Xaa Xaa Phe Xaa Asn Ala
            20                  25                  30

Trp Met Ser Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Xaa Ile Ser Arg Asp Asp Ser Lys Asn Xaa
65                  70                  75                  80

Leu Xaa Leu Xaa Met Xaa Ser Leu Xaa Thr Glu Asp Thr Ala Val Tyr
            85                  90                  95

Tyr Cys Xaa Thr Asp Gly Pro Tyr Ser Asp Asp Phe Arg Ser Gly Tyr
            100                 105                 110

Ala Ala Arg Tyr Arg Tyr Phe Gly Met Asp Val Trp Gly Gln Gly Thr
        115                 120                 125

Thr Val Thr Val Ser Ser
    130

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (87)..(87)
<223> OTHER INFORMATION: Phe or Tyr

<400> SEQUENCE: 72

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Xaa Cys Gln Gln Ala Asn Ser Phe Pro Pro
                85                  90                  95

Thr Phe Gly Gln Gly Thr Lys Leu Glu Ile Lys
            100                 105

<210> SEQ ID NO 73
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gaggtgcagc tggtggagtc tgggggaggc ttggtaaagc ctggggggtc ccttagactc     60
tcctgtgcag cctctggatt ctctttcagt aacgcctgga tgagctgggt ccgccaggct    120
ccagggaagg gcctggagtg ggttggccgt attaaaagta atactgatgg tgggacaaca    180
gactacgccg cacccgtgaa aggcagattc accatctcaa gagacgattc aaagaacacg    240
ctgtatctgc aaatgagcag cctgaaaacc gaggacacag ccgtctatta ctgcaccaca    300
gatggacctt actctgacga ttttagaagt ggttatgccg cacgctaccg ttatttcgga    360
atggacgtct ggggccaagg gaccacggtc accgtctcct ca                       402

<210> SEQ ID NO 74
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Ser Ser Leu Lys Thr Glu Asp Thr Ala Val Tyr
                85                  90                  95

Tyr Cys Thr Thr Asp Gly Pro Tyr Ser Asp Asp Phe Arg Ser Gly Tyr
            100                 105                 110

Ala Ala Arg Tyr Arg Tyr Phe Gly Met Asp Val Trp Gly Gln Gly Thr
            115                 120                 125

Thr Val Thr Val Ser Ser
            130

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ala Ser Gln Asp Ile Ser Thr Trp Leu Ala
1               5                   10

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ile Lys Ser Asn Thr Asp Gly Gly Thr Thr Asp Tyr Ala Ala Pro
1               5                   10                  15

Val Lys Gly

<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Gly Pro Tyr Ser Asp Asp Phe Arg Ser Gly Tyr Ala Ala Arg Tyr
1               5                   10                  15

Arg Tyr Phe Gly Met Asp Val
            20

<210> SEQ ID NO 78
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Phe Ser Phe Ser Asn Ala Trp
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Lys Ser Asn Thr Asp Gly Gly Thr Thr
1               5                   10

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Thr Asp Gly Pro Tyr Ser Asp Asp Phe Arg Ser Gly Tyr Ala Ala
1               5                   10                  15

Arg Tyr Arg Tyr Phe Gly Met Asp Val
            20                  25

<210> SEQ ID NO 81
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gacatccaga tgacccagtc tccatcttcc gtgtctgcat ctgtgggaga cagagtcacc      60
atcacttgtc gggcgagtca ggatattagc acctggttag cctggtatca gcagaaacca     120
gggaaagccc ctaagctcct gatctatgct gcatccagtt tgcaaagtgg ggtcccatca     180
agattcagcg gcagtggatc tgggacagat ttcactctca ccatcagcag cctgcagcct     240
gaagattttg caacttacta ttgtcagcag gctaacagtt tccctccgac ttttggccag     300
gggaccaagc tggagatcaa ac                                              322

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Ser Val Ser Ala Ser Val Gly
1               5                   10                  15
```

```
Asp Arg Val Thr Ile Thr Cys Arg Ala Ser Gln Asp Ile Ser Thr Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Pro
                 85                  90                  95

Thr Phe Gly Gln Gly Thr Lys Leu Glu Ile Lys
            100                 105
```

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Arg Ala Ser Gln Asp Ile Ser Thr Trp Leu Ala
 1               5                  10
```

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Ala Ala Ser Ser Leu Gln Ser
 1               5
```

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

```
Gln Gln Ala Asn Ser Phe Pro Pro Thr
 1               5
```

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Gln Asp Ile Ser Thr Trp
 1               5
```

<210> SEQ ID NO 87
<211> LENGTH: 3
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 87

Ala Ala Ser
1

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Gln Ala Asn Ser Phe Pro Pro Thr
1               5

<210> SEQ ID NO 89
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gaggtgcagc tggtggagtc tgggggaggc ttggtaaagc ctggggggtc ccttagactc    60
tcctgtgcag cctctggact cactttcagt aacgcctgga tgagctgggt ccgccaggct   120
ccagggaagg gcctggagtg ggttggccgt attaaaagta atactgatgg tgggacaaca   180
gactacgccg cacccgtgaa aggcagattc accatctcaa gagacgattc aaagaacacg   240
ctgtatctgc aaatgagcag cctgaaaacc gaggacacag ccgtctatta ctgcaccaca   300
gatggacctt actctgacga tttttagaagt ggttatgccg cacgctaccg ttatttcgga   360
atggacgtct ggggccaagg gaccacggtc accgtctcct ca                      402

<210> SEQ ID NO 90
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Leu Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Ser Ser Leu Lys Thr Glu Asp Thr Ala Val Tyr
                85                  90                  95

Tyr Cys Thr Thr Asp Gly Pro Tyr Ser Asp Asp Phe Arg Ser Gly Tyr
            100                 105                 110
```

Ala Ala Arg Tyr Arg Tyr Phe Gly Met Asp Val Trp Gly Gln Gly Thr
          115                 120                 125

Thr Val Thr Val Ser Ser
        130

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ala Ser Gln Asp Ile Ser Thr Trp Leu Ala
1               5                   10

<210> SEQ ID NO 92
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Ile Lys Ser Asn Thr Asp Gly Gly Thr Thr Asp Tyr Ala Ala Pro
1               5                   10                  15

Val Lys Gly

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Gly Pro Tyr Ser Asp Asp Phe Arg Ser Gly Tyr Ala Ala Arg Tyr
1               5                   10                  15

Arg Tyr Phe Gly Met Asp Val
              20

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Leu Thr Phe Ser Asn Ala Trp
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile Lys Ser Asn Thr Asp Gly Gly Thr Thr
1               5                   10

<210> SEQ ID NO 96
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Thr Asp Gly Pro Tyr Ser Asp Asp Phe Arg Ser Gly Tyr Ala Ala
1               5                   10                  15

Arg Tyr Arg Tyr Phe Gly Met Asp Val
            20                  25

<210> SEQ ID NO 97
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gacatccaga tgacccagtc tccatcttcc gtgtctgcat ctgtgggaga cagagtcacc    60
atcacttgtc gggcgagtca ggatattagc acctggttag cctggtatca gcagaaacca   120
gggaaagccc ctaagctcct gatctatgct gcatccagtt tgcaaagtgg ggtcccatca   180
agattcagcg gcagtggatc tgggacagat ttcactctca ccatcagcag cctgcagcct   240
gaagattttg caacttacta ttgtcagcag gctaacagtt tccctccgac ttttggccag   300
gggaccaagc tggagatcaa ac                                            322

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105

<210> SEQ ID NO 99
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 99

Arg Ala Ser Gln Asp Ile Ser Thr Trp Leu Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Ala Ser Ser Leu Gln Ser
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Ala Asn Ser Phe Pro Pro Thr
1               5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Asp Ile Ser Thr Trp
1               5

<210> SEQ ID NO 103
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Ala Ser
1

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Gln Ala Asn Ser Phe Pro Pro Thr
1               5
```

<210> SEQ ID NO 105
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
gaggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg gcctggagtg ggttggccgt attaaaagta atactgatgg tgggacaaca    180
gactacgccg cacccgtgaa aggcagattc accatctcaa gagacgattc aaagaacacg    240
ctgtatctgc aaatgagcag cctgaaaacc gaggacacag ccgtctatta ctgcaccaca    300
gatggacctt actctgacga ttttagaagt ggttatgccg cacgctaccg ttatttcgga    360
atggacgtct ggggccaagg gaccacggtc accgtctcct ca                       402
```

<210> SEQ ID NO 106
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Asn Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Ser Ser Leu Lys Thr Glu Asp Thr Ala Val Tyr
                85                  90                  95

Tyr Cys Thr Thr Asp Gly Pro Tyr Ser Asp Asp Phe Arg Ser Gly Tyr
            100                 105                 110

Ala Ala Arg Tyr Arg Tyr Phe Gly Met Asp Val Trp Gly Gln Gly Thr
        115                 120                 125

Thr Val Thr Val Ser Ser
    130
```

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Arg Ala Ser Gln Asp Ile Ser Thr Trp Leu Ala
1               5                   10
```

```
<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ile Lys Ser Asn Thr Asp Gly Gly Thr Thr Asp Tyr Ala Ala Pro
1               5                   10                  15

Val Lys Gly

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Gly Pro Tyr Ser Asp Asp Phe Arg Ser Gly Tyr Ala Ala Arg Tyr
1               5                   10                  15

Arg Tyr Phe Gly Met Asp Val
            20

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Phe Thr Phe Ser Asn Ala Trp
1               5

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Lys Ser Asn Thr Asp Gly Gly Thr Thr
1               5                   10

<210> SEQ ID NO 112
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Asp Gly Pro Tyr Ser Asp Asp Phe Arg Ser Gly Tyr Ala Ala Arg
1               5                   10                  15

Tyr Arg Tyr Phe Gly Met Asp Val
            20

<210> SEQ ID NO 113
```

<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
gacatccaga tgacccagtc tccatcttcc gtgtctgcat ctgtgggaga cagagtcacc     60
atcacttgtc gggcgagtca ggatattagc acctggttag cctggtatca gcagaaacca    120
gggaaagccc ctaagctcct gatctatgct gcatccagtt tgcaaagtgg ggtcccatca    180
agattcagcg gcagtggatc tgggacagat ttcactctca ccatcagcag cctgcagcct    240
gaagattttg caacttacta ttgtcagcag gctaacagtt tccctccgac ttttggccag    300
gggaccaagc tggagatcaa ac                                             322

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Ala Ser Gln Asp Ile Ser Thr Trp Leu Ala
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Ala Ser Ser Leu Gln Ser

```
1               5
```

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Gln Gln Ala Asn Ser Phe Pro Pro Thr
1               5
```

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Gln Asp Ile Ser Thr Trp
1               5
```

<210> SEQ ID NO 119
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Ala Ala Ser
1
```

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Gln Gln Ala Asn Ser Phe Pro Pro Thr
1               5
```

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Gly Leu Ser Phe Leu Asn Ala Trp
1               5
```

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Ile Lys Ser Asn Thr Asp Gly Gly Thr Thr
1               5                   10

<210> SEQ ID NO 123
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Thr Asp Gly Pro Tyr Ser Asp Asp Phe Arg Ser Gly Tyr Ala Ala Arg
1               5                   10                  15

Tyr Arg Tyr Phe Gly Met Asp Val Trp
            20                  25

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Asp Ile Ser Thr Trp
1               5

<210> SEQ ID NO 125
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ala Ser
1

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Gln Ala Asn Ser Phe Pro Pro Thr
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Leu Ser Phe Leu Asn Ala Trp
1               5

```
<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Lys Ser Asn Thr Asp Gly Gly Thr Thr
1               5                   10

<210> SEQ ID NO 129
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Thr Asp Gly Pro Tyr Ser Asp Asp Phe Arg Ser Gly Tyr Ala Ala
1               5                   10                  15

Arg Tyr Arg Tyr Phe Gly Met Asp Val
            20                  25

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Asp Ile Ser Thr Trp
1               5

<210> SEQ ID NO 131
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ala Ser
1

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Gln Ala Asn Ser Phe Pro Pro Thr
1               5

<210> SEQ ID NO 133
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 133

Gly Phe Ser Phe Leu Asn Ala Trp
1               5

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Lys Ser Asn Thr Asp Gly Gly Thr Thr
1               5                   10

<210> SEQ ID NO 135
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Thr Asp Gly Pro Tyr Ser Asp Asp Phe Arg Ser Gly Tyr Ala Ala
1               5                   10                  15

Arg Tyr Arg Tyr Phe Gly Met Asp Val
            20                  25

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Asp Ile Ser Thr Trp
1               5

<210> SEQ ID NO 137
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ala Ser
1

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138
```

Gln Gln Ala Asn Ser Phe Pro Pro Thr
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Leu Thr Phe Leu Asn Ala Trp
1               5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Lys Ser Asn Thr Asp Gly Gly Thr Thr
1               5                   10

<210> SEQ ID NO 141
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Thr Asp Gly Pro Tyr Ser Asp Asp Phe Arg Ser Gly Tyr Ala Ala
1               5                   10                  15

Arg Tyr Arg Tyr Phe Gly Met Asp Val
            20                  25

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Asp Ile Ser Thr Trp
1               5

<210> SEQ ID NO 143
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Ala Ser
1

<210> SEQ ID NO 144
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Gln Ala Asn Ser Phe Pro Pro Thr
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Phe Thr Phe Leu Asn Ala Trp
1               5

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Lys Ser Asn Thr Asp Gly Gly Thr Thr
1               5                   10

<210> SEQ ID NO 147
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Thr Thr Asp Gly Pro Tyr Ser Asp Asp Phe Arg Ser Gly Tyr Ala Ala
1               5                   10                  15

Arg Tyr Arg Tyr Phe Gly Met Asp Val
            20                  25

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Asp Ile Ser Thr Trp
1               5

<210> SEQ ID NO 149
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 149

Ala Ala Ser
1

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Gln Ala Asn Ser Phe Pro Pro Thr
1               5

<210> SEQ ID NO 151
<211> LENGTH: 347
<212> TYPE: PRT
<213> ORGANISM: Influenza B virus

<400> SEQUENCE: 151

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Asn Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu His Ile Arg Leu Ser Thr His Asn Val Ile Asn Ala Glu
        115                 120                 125

Asn Ala Pro Gly Gly Pro Tyr Lys Ile Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asn Asp Asn Asn Lys Thr Ala Thr Asn Ser Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Asn Glu Ile Gln Met Ala Lys Leu Tyr Gly Asp Ser
        195                 200                 205

Lys Pro Gln Lys Phe Thr Ser Ser Ala Asn Gly Val Thr Thr His Tyr
    210                 215                 220

Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
```

```
            275                 280                 285
Leu Ile Gly Glu Ala Asp Cys Leu His Glu Lys Tyr Gly Gly Leu Asn
    290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg
                340                 345

<210> SEQ ID NO 152
<211> LENGTH: 346
<212> TYPE: PRT
<213> ORGANISM: Influenza B virus

<400> SEQUENCE: 152

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Gly Ser Cys Pro
    130                 135                 140

Asn Ala Thr Ser Lys Ser Gly Phe Phe Ala Thr Met Ala Trp Ala Val
145                 150                 155                 160

Pro Lys Asp Asn Lys Asn Ala Thr Asn Pro Leu Thr Val Glu Val
                165                 170                 175

Pro Tyr Ile Cys Thr Glu Gly Glu Asp Gln Ile Thr Val Trp Gly Phe
            180                 185                 190

His Ser Asp Asp Lys Thr Gln Met Lys Asn Leu Tyr Gly Asp Ser Asn
        195                 200                 205

Pro Gln Lys Phe Thr Ser Ser Ala Asn Gly Val Thr Thr His Tyr Val
    210                 215                 220

Ser Gln Ile Gly Ser Phe Pro Asp Gln Thr Glu Asp Gly Gly Leu Pro
225                 230                 235                 240

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
    290                 295                 300
```

```
Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg
            340                 345

<210> SEQ ID NO 153
<211> LENGTH: 346
<212> TYPE: PRT
<213> ORGANISM: Influenza B virus

<400> SEQUENCE: 153

Asp Arg Ile Cys Thr Gly Ile Thr Ser Ser

Arg Pro Pro Ala Lys Leu Leu Lys Glu Arg
            340                 345

<210> SEQ ID NO 154
<211> LENGTH: 346
<212> TYPE: PRT
<213> ORGANISM: Influenza B virus

<400> SEQUENCE: 154

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Asn Ala Pro Gly Gly Pro Tyr Arg Leu Gly Thr Ser Arg Ser Cys Pro
    130                 135                 140

Asn Ala Thr Ser Lys Ser Gly Phe Phe Ala Thr Met Ala Trp Ala Val
145                 150                 155                 160

Pro Lys Asp Asn Asn Lys Asn Ala Thr Asn Pro Leu Thr Val Glu Val
                165                 170                 175

Pro Tyr Val Cys Thr Glu Gly Glu Asp Gln Ile Thr Val Trp Gly Phe
            180                 185                 190

His Ser Asp Asn Lys Thr Gln Met Lys Asn Leu Tyr Gly Asp Ser Asn
        195                 200                 205

Pro Gln Lys Phe Thr Ser Ser Ala Asn Gly Val Thr Thr His Tyr Val
    210                 215                 220

Ser Gln Ile Gly Gly Phe Pro Ala Gln Thr Glu Asp Glu Gly Leu Pro
225                 230                 235                 240

Gln Ser Gly Arg Ile Val Val Asp Tyr Met Val Gln Lys Pro Arg Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
    290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg
            340                 345

-continued

```
<210> SEQ ID NO 155
<211> LENGTH: 347
<212> TYPE: PRT
<213> ORGANISM: Influenza B virus

<400> SEQUENCE: 155

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Asn Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu His Ile Arg Leu Ser Thr His Asn Val Ile Asn Ala Glu
        115                 120                 125

Asn Ala Pro Gly Gly Pro Tyr Lys Ile Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asn Asp Asn Asn Lys Thr Ala Thr Asn Ser Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Asn Glu Ile Gln Met Ala Lys Leu Tyr Gly Asp Ser
        195                 200                 205

Lys Pro Gln Lys Phe Thr Ser Ser Ala Asn Gly Val Thr Thr His Tyr
    210                 215                 220

Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
        275                 280                 285

Leu Ile Gly Glu Ala Asp Cys Leu His Glu Lys Tyr Gly Gly Leu Asn
    290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg
            340                 345

<210> SEQ ID NO 156
<211> LENGTH: 346
<212> TYPE: PRT
<213> ORGANISM: Influenza B virus
```

<400> SEQUENCE: 156

```
Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Gly Ser Cys Pro
    130                 135                 140

Asn Ala Thr Ser Lys Ser Gly Phe Phe Ala Thr Met Ala Trp Ala Val
145                 150                 155                 160

Pro Lys Asp Asn Lys Asn Ala Thr Asn Pro Leu Thr Val Glu Val
                165                 170                 175

Pro Tyr Ile Cys Thr Glu Gly Glu Asp Gln Ile Thr Val Trp Gly Phe
            180                 185                 190

His Ser Asp Asp Lys Thr Gln Met Lys Asn Leu Tyr Gly Asp Ser Asn
        195                 200                 205

Pro Gln Lys Phe Thr Ser Ala Asn Gly Val Thr Thr His Tyr Val
    210                 215                 220

Ser Gln Ile Gly Ser Phe Pro Asp Gln Thr Glu Asp Gly Gly Leu Pro
225                 230                 235                 240

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
    290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg
            340                 345
```

<210> SEQ ID NO 157
<211> LENGTH: 346
<212> TYPE: PRT
<213> ORGANISM: Influenza B virus

<400> SEQUENCE: 157

```
Asp Arg Ile Cys Thr Gly Ile Thr Ser Ser Asn Ser Pro His Val Val
1               5                   10                  15
```

```
Lys Thr Ala Thr Gln Gly Glu Val Asn Val Thr Gly Val Ile Pro Leu
                20                  25                  30

Thr Thr Thr Pro Thr Lys Ser Tyr Phe Ala Asn Leu Lys Gly Thr Arg
            35                  40                  45

Thr Arg Gly Lys Leu Cys Pro Asp Cys Leu Asn Cys Thr Asp Leu Asp
        50                  55                  60

Val Ala Leu Gly Arg Pro Met Cys Val Gly Thr Thr Pro Ser Ala Lys
 65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Glu Ser Cys Pro
130                 135                 140

Asn Ala Thr Ser Lys Ser Gly Phe Phe Ala Thr Met Ala Trp Ala Val
145                 150                 155                 160

Pro Lys Asp Asn Lys Asn Ala Thr Asn Pro Leu Thr Val Glu Val
                165                 170                 175

Pro Tyr Ile Cys Thr Glu Gly Glu Asp Gln Ile Thr Val Trp Gly Phe
            180                 185                 190

His Ser Asp Asp Lys Thr Gln Met Lys Asn Leu Tyr Gly Asp Ser Asn
        195                 200                 205

Pro Gln Lys Phe Thr Ser Ser Ala Asn Gly Val Thr Thr His Tyr Val
    210                 215                 220

Ser Gln Ile Gly Ser Phe Pro Asp Gln Thr Glu Asp Gly Gly Leu Pro
225                 230                 235                 240

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
    290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg
            340                 345

<210> SEQ ID NO 158
<211> LENGTH: 346
<212> TYPE: PRT
<213> ORGANISM: Influenza B virus

<400> SEQUENCE: 158

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
                20                  25                  30

Thr Thr Thr Pro Thr Lys Ser Tyr Phe Ala Asn Leu Lys Gly Thr Arg
            35                  40                  45
```

```
Thr Arg Gly Lys Leu Cys Pro Asp Cys Leu Asn Cys Thr Asp Leu Asp
    50                  55                  60
Val Ala Leu Gly Arg Pro Met Cys Val Gly Thr Thr Pro Ser Ala Lys
65                  70                  75                  80
Ala Ser Ile Leu His Glu Val Arg Pro Val Thr Ser Gly Cys Phe Pro
                85                  90                  95
Ile Met His Asp Arg Thr Lys Ile Arg Gln Leu Pro Asn Leu Leu Arg
            100                 105                 110
Gly Tyr Glu Asn Ile Arg Leu Ser Thr Gln Asn Val Ile Asp Ala Glu
        115                 120                 125
Asn Ala Pro Gly Gly Pro Tyr Arg Leu Gly Thr Ser Arg Ser Cys Pro
    130                 135                 140
Asn Ala Thr Ser Lys Ser Gly Phe Phe Ala Thr Met Ala Trp Ala Val
145                 150                 155                 160
Pro Lys Asp Asn Asn Lys Asn Ala Thr Asn Pro Leu Thr Val Glu Val
                165                 170                 175
Pro Tyr Val Cys Thr Glu Gly Glu Asp Gln Ile Thr Val Trp Gly Phe
            180                 185                 190
His Ser Asp Asn Lys Thr Gln Met Lys Asn Leu Tyr Gly Asp Ser Asn
        195                 200                 205
Pro Gln Lys Phe Thr Ser Ser Ala Asn Gly Val Thr Thr His Tyr Val
    210                 215                 220
Ser Gln Ile Gly Gly Phe Pro Ala Gln Thr Glu Asp Glu Gly Leu Pro
225                 230                 235                 240
Gln Ser Gly Arg Ile Val Val Asp Tyr Met Val Gln Lys Pro Arg Lys
                245                 250                 255
Thr Gly Thr Ile Val Tyr Gln Arg Gly Val Leu Leu Pro Gln Lys Val
            260                 265                 270
Trp Cys Ala Ser Gly Arg Ser Lys Val Ile Lys Gly Ser Leu Pro Leu
        275                 280                 285
Ile Gly Glu Ala Asp Cys Leu His Glu Lys Tyr Gly Gly Leu Asn Lys
    290                 295                 300
Ser Lys Pro Tyr Tyr Thr Gly Glu His Ala Lys Ala Ile Gly Asn Cys
305                 310                 315                 320
Pro Ile Trp Val Lys Thr Pro Leu Lys Leu Ala Asn Gly Thr Lys Tyr
                325                 330                 335
Arg Pro Pro Ala Lys Leu Leu Lys Glu Arg
            340                 345
```